US009987352B2

(12) United States Patent
King et al.

(10) Patent No.: US 9,987,352 B2
(45) Date of Patent: Jun. 5, 2018

(54) YEAST-BASED COMPOSITIONS AND METHODS FOR THE TREATMENT OR PREVENTION OF HEPATITIS DELTA VIRUS INFECTION

(71) Applicant: GLOBEIMMUNE, INC., Louisville, CO (US)

(72) Inventors: Thomas H. King, Denver, CO (US); David Apelian, Boonton Township, NJ (US)

(73) Assignee: GlobeImmune, Inc., Louisville, CO (US)

(*) Notice: Subject to any disclaimer, the term of this patent is extended or adjusted under 35 U.S.C. 154(b) by 0 days. days.

(21) Appl. No.: 15/408,087

(22) Filed: Jan. 17, 2017

(65) Prior Publication Data
US 2017/0182153 A1 Jun. 29, 2017

Related U.S. Application Data

(62) Division of application No. 14/125,779, filed as application No. PCT/US2012/042426 on Jun. 14, 2012, now Pat. No. 9,579,377.

(60) Provisional application No. 61/497,039, filed on Jun. 14, 2011.

(51) Int. Cl.
A61K 39/00 (2006.01)
A61K 39/29 (2006.01)
C07K 14/005 (2006.01)
A61K 38/21 (2006.01)
A61K 45/06 (2006.01)

(52) U.S. Cl.
CPC .............. A61K 39/29 (2013.01); A61K 38/21 (2013.01); A61K 38/212 (2013.01); A61K 45/06 (2013.01); C07K 14/005 (2013.01); A61K 2039/523 (2013.01); A61K 2039/645 (2013.01); C07K 2319/09 (2013.01); C07K 2319/40 (2013.01); C12N 2760/10134 (2013.01)

(58) Field of Classification Search
None
See application file for complete search history.

(56) References Cited

U.S. PATENT DOCUMENTS

| 4,775,622 A | 10/1988 | Hitzeman et al. |
| 5,234,830 A | 8/1993 | Oshima et al. |
| 5,310,654 A | 5/1994 | Isberg et al. |
| 5,413,914 A | 5/1995 | Franzusoff |
| 5,830,463 A | 11/1998 | Duke et al. |
| 5,858,378 A | 1/1999 | Bostwick |
| 5,919,651 A | 7/1999 | Hitzeman et al. |
| 6,599,508 B1* | 7/2003 | Gissmann .............. A61K 39/12 424/184.1 |
| 6,844,171 B1 | 1/2005 | Hogle et al. |
| 7,083,787 B2 | 8/2006 | Duke et al. |
| 7,351,570 B2 | 4/2008 | Deny et al. |
| 7,439,042 B2 | 10/2008 | Duke et al. |
| 7,465,454 B2 | 12/2008 | Franzusoff et al. |
| 7,595,060 B2 | 9/2009 | Duke et al. |
| 7,736,642 B2* | 6/2010 | Duke ................... A61K 39/145 424/184.1 |
| 9,579,377 B2 | 2/2017 | King et al. |
| 2002/0044948 A1 | 4/2002 | Khleif et al. |
| 2003/0035810 A1 | 2/2003 | Caplan |
| 2007/0172503 A1 | 7/2007 | Selitrennikoff et al. |
| 2007/0224208 A1 | 9/2007 | Guo et al. |
| 2008/0003239 A1 | 1/2008 | Duke et al. |
| 2008/0187933 A1 | 8/2008 | Deny et al. |
| 2010/0034840 A1 | 2/2010 | Apelian et al. |
| 2010/0111912 A1 | 5/2010 | Apelian et al. |
| 2010/0189749 A1 | 7/2010 | Franzusoff et al. |
| 2011/0256098 A1 | 10/2011 | Apelian et al. |
| 2012/0107347 A1 | 5/2012 | Hodge et al. |
| 2012/0321664 A1 | 12/2012 | Bellgrau et al. |

FOREIGN PATENT DOCUMENTS

| EP | 0414404 | 2/1991 |
| FR | 2486400 | 1/1982 |
| WO | WO 1998/028004 | 7/1998 |
| WO | WO 03/051912 | 6/2003 |
| WO | WO 2010/033841 | 3/2010 |
| WO | WO 2010/065626 | 6/2010 |
| WO | WO 2010/073204 | 7/2010 |
| WO | WO 2010/121180 | 10/2010 |
| WO | WO 2011/015656 | 2/2011 |
| WO | WO 2011/115914 | 9/2011 |
| WO | WO 2012/019127 | 2/2012 |
| WO | WO 2012/083302 | 6/2012 |
| WO | WO 2012/109404 | 8/2012 |
| WO | WO 2012/125998 | 9/2012 |

(Continued)

OTHER PUBLICATIONS

Wu et al. Assembly of Hepatitis Delta Virus-like Empty Particles in Yeast. VIROLOGY 236, 374-381 (1997).*
Wedemeyer et al. Treatment of Hepatitis Delta. Clinical Liver Disease. vol. 2, Issue 6, Version of Record online: Dec. 20, 2013.*
UniProtKB/Swiss-Prot: Q9E927. Large delta antigen. Oct. 31, 2006.*
GenBank: CAC51366.1. hepatitis delta antigen, partial [Hepatitis delta virus] 2001.*
Baker et al., Protein Structure Predication and Structural Genomics, Science (2001) vol. 294, No. 5540, pp. 93-96. (Year: 2001).*
Attwood, T. The Babel of Bioinformatics, Science (2000) vol. 290, No. 5491, pp. 471-473 (Year: 2000).*
"Large delta antigen" UniProtKB/Swiss-Prot: Q9E927, 2006, 1 page.
Abbas et al. "Hepatitis D: Scenario in the Asia-Pacific region," World Journal of Gastroenterology, Feb. 2010, vol. 16, No. 5, pp. 554-562.
Alves et al., "Characterization of the nuclear localization signal of the hepatitis delta virus antigen," Virology, 2008, vol. 370, Iss. 1, pp. 12-21.
Bizzini et al. "Use of live *Saccharomyces cerevisiae* cells as a biological response modifier in experimental infections," FEMS Microbiology Immunology, 1990, vol. 64, pp. 155-168.

(Continued)

Primary Examiner — Michelle S Horning
(74) Attorney, Agent, or Firm — Sheridan Ross P.C.

(57) ABSTRACT

Disclosed are immunotherapeutic compositions and methods for preventing and/or treating hepatitis delta virus (HDV) infection, including yeast-based HDV immunotherapeutic compositions and methods of use of such compositions to prevent and/or treat HDV infection and symptoms and sequela thereof.

20 Claims, 6 Drawing Sheets

(56) References Cited

FOREIGN PATENT DOCUMENTS

WO    WO 2013/025972    2/2013

OTHER PUBLICATIONS

Brake et al. "alpha-Factor-directed synthesis and secretion of mature foreign proteins in *Saccharomyces cerevisiae*," Proceedings of the National Academy of Sciences USA, Aug. 1984, vol. 81, pp. 4642-4646.

Chou et al., "Hepatitis Delta Antigen Mediates the Nuclear Import of Hepatitis Delta Virus RNA" Journal of Virology, 1998, vol. 72, No. 5, pp. 3684-3690.

Celik et al. "Complete genome sequences and phylogenetic analysis of hepatitis delta viruses isolated from nine Turkish patients," Archives of Virology, Dec. 2011, vol. 156, No. 12, pp. 2215-2220.

Eto et al., "Immunization with recombinant *Escherichia coli* expressing retinal S-antigen-induced experimental autoimmune uveitis (EAU) in Lewis rats", Cellular Immunology, vol. 147, No. 1 Mar. 1993, pp. 203-214.

Franzusoff, A. et al. "Yeasts Encoding Tumour Antigens in Cancer Immunotherapy," Expert Opinion on Biological Therapy, Apr. 2005, vol. 5, No. 4, pp. 565-575.

Franzusoff et al. "Biochemical and Genetic Definition of the Cellular Protease Required for HIV-1 gp160 Processing," The Journal of Biological Chemistry, Feb. 1995, vol. 270, No. 7, pp. 3154-3159.

Fujita et al. "Studies in the development of Japanese encephalitis vaccine: expression of virus envelope glycoprotein V3 (E) gene in yeast," Bulletin of the World Health Organization, Feb. 1987, vol. 65, No. 3, pp. 303-308.

Grabowski et al. "Hepatitis Delta: Immunopathogenesis and Clinical Challenges," Digestive Diseases, May 2010, vol. 28, No. 1, pp. 133-138.

Huang et al. "Generation of cytotoxicity against hepatitis delta virus genotypes and quasispecies by epitope modification," Journal of Hepatology, Apr. 2009, vol. 50, No. 4, pp. 779-788.

Huang et al. "Identification of novel HLA-A*0201-restricted CD8+ T-cell epitopes on hepatitis delta virus," Journal of General Virology, Oct. 2004, vol. 85, No. 10, pp. 3089-3098.

Huang, Y-H et al. "Varied Immunity Generated in Mice by DNA Vaccines with Large and Small Hepatitis Delta Antigens", Journal of Virology. 2003. 77(24): 12980-12985, p. 12981.

Ivaniushina et al., UniProtKB/Swiss-Prot Accession No. Q912D8, 2006, 1 page.

Klepfer et al. "Characterization of rabies glycoprotein expressed in yeast," Archives of Virology, 1993, vol. 128, pp. 269-286.

Le Gal, et al., "Eighth Major Clade for Hepatitis Delta Virus," Emerging Infections Diseases, 2006, vol. 12, No. 9, pp. 1447-1450.

Li et al. "Hepatitis Delta Virus Antigen is Methylated at Arginine Residues, and Methylation Regulates Subcellular Localization and RNA Replication," Journal of Virology, Dec. 2004, vol. 78, No. 23, pp. 13325-13334.

Li et al., "The Molecular Biology of Hepatitis delta virus," Virologica Siniga, 2003, Iss. 3, pp. 298-302. (English translation).

Lu, et al., "Mutation-Selective Tumor Remission with Ras-Targeted, Whole Yeast-Based Immunotherapy," Cancer Research, 2004, vol. 64, pp. 5084-5088.

Moore et al., "Novel yeast-based vaccine 1-40, against HIV-SF2 gp160 promotes a cytotoxic 43-62 cell response," FASEB Journal (online), vol. 10. No. 6. 1996, p. A1473, ZP002186594, Joint Meeting of the American Society for Biochemistry and Molecular Biology, the American Society for Investigative Pathology and the American Association of Immunologists; New Orleans, LA, USA; Jun. 2-6, 1996.

Netter et al. "Nucleotide Sequence Stability of the Genome of Hepatitis Delta Virus," Journal of Virology, Mar. 1995, vol. 69, No. 3, pp. 1687-1692.

Nisini et al. "Human CD4+ T-cell response to hepatitis delta virus: identification of multiple epitopes and characterization of T-helper cytokine profiles." Journal of Virology, May 1997, vol. 71, No. 3, pp. 2241-2251.

Pascarella et al. "Hepatitis D virus: an update," Liver International, Jan. 2011, vol. 31, No. 1, pp. 7-21.

Saldanha et al. "Cloning and sequencing of RNA of hepatitis delta virus isolated from human serum," Journal of General Virology, Jul. 1990, vol. 71, No. 7, pp. 1603-1606.

Schreuder et al. "Yeast expressing hepatitis B virus surface antigen determinants on its surface: implications for a possible oral vaccine," Vaccine, Apr. 1996, vol. 14, No. 5, pp. 383-388.

Sinai et al. "Enhancement of Resistance to Infectious Diseases by Oral Administration of Brewer's Yeast," Infection and Immunity, May 1974, vol. 9, No. 5, pp. 781-787.

Stubbs, et al., "Whole Recombinant Yeast Vaccine Activates Dendritic Cells and Elicits Protective Cell-Mediated Immunity," National Medicine, May 2001, vol. 7, No. 5, pp. 1-5.

Valenzuela et al. "Antigen engineering in yeast: Synthesis and assembly of hybrid hepatitis B surface antigen-Herpes simplex 1 gD particles", Bio/Technology, Apr. 1985, vol. 3, 323-326.

Wedemeyer et al. "Peginterferon plus Adefovir versus Either Drug Alone for Hepatitis Delta," The New England Journal of Medicine, Jan. 2011, vol. 364, No. 4, pp. 322-331.

Wu et al. "Characterization and phylogenetic analysis of a novel hepatitis D virus strain discovered by restriction fragment length polymorphism analysis," Journal of General Virology, May 1998, vol. 79, No. 5, pp. 1105-1113.

International Search Report prepared by the Australian Patent Office dated Jul. 24, 2012, for International Application No. PCT/US2012/042426.

Written Opinion prepared by the Australian Patent Office dated Jul. 24, 2012, for International Application No. PCT/US2012/042426.

International Preliminary Report on Patentability for International (PCT) Patent Application No. PCT/US2012/042426, dated Jan. 3, 2014 6 pages.

Official Action for Australian Patent Application No. 2012271625 dated May 5, 2016, 2 pages.

Official Action (English translation) for Chinese Patent Application No. 201280039821.5 dated Dec. 25, 2014, 7 pages.

Official Action (English translation) for Chinese Patent Application No. 201280039821.5 dated Sep. 15, 2015, 9 pages.

Official Action (English translation) for Chinese Patent Application No. 201280039821.5 dated Jun. 7, 2016, 5 pages.

Official Action (with English translation) for Eurasian Patent Application No. 201490015/28, dated Feb. 25, 2016, 4 pages.

Official Action (with English translation) for Eurasian Patent Application No. 201490015/28, dated Aug. 3, 2016, 8 pages.

Extended European Search Report for European Patent Application No. 12800096.5 dated Feb. 6, 2015, 9 pages.

Official Action for European Patent Application No. 12800096.5 dated Jun. 13, 2016, 4 pages.

Official Action (with English translation) for Japanese Patent Application No. 2014-515985 dated Apr. 26, 2016, 5 pages.

Official Action for New Zealand Patent Application No. 619761 dated Oct. 8, 2014, 2 pages.

Notice of Acceptance for New Zealand Patent Application No. 619761 dated Aug. 7, 2015, 1 page.

Official Action for U.S. Appl. No. 14/125,779 dated Sep. 1, 2015, 9 pages.

Official Action for U.S. Appl. No. 14/125,779 dated Nov. 30, 2015, 9 pages.

Official Action for U.S. Appl. No. 14/125,779 dated May 12, 2016, 11 pages.

Notice of Allowance for U.S. Appl. No. 14/125,779 dated Dec. 2, 2016, 5 pages.

Notice of Acceptance for Australian Patent Application No. 2012271625 dated May 9, 2017, 3 pages.

Official Action (with English translation) for Eurasian Patent Application No. 201490015/28, dated Jul. 10, 2017, 4 pages.

Official Action for European Patent Application No. 12800096.5 dated Apr. 11, 2017, 6 pages.

(56) References Cited

OTHER PUBLICATIONS

Official Action (with English translation) for Israeli Patent Application No. 229902 dated Jul. 27, 2017, 6 pages.
Notice of Allowance (with English translation) for Eurasian Patent Application No. 201490015/28, dated Jul. 10, 2017, 4 pages.
Notice of Intention to Grant for European Patent Application No. 12800096.5 dated Oct. 11, 2017, 7 pages.

* cited by examiner

FIG. 1

```
_genotype1   -MGRKKLEDLERDLRKIKKKIKKLEDENPWLGMNIKGILGKKDKDGEGAPPAKRARTDQME  59
_genotype2   VSTRKKAEELERDLRKIKKARKTIKRLEDDNPWLGMILGIIRK-GKDGEGAPPAKRARTDQME  59
_genotype3   VEERKMRRKLEKDLRRAMKKIKKLEDENPWLGMNVVGLLRR-KKDEDGAPPAKRPRQETME  59
              .* ..:*:.:***. .*:.*:.****:*:********. *  :.********:..*

_genotype1   IDSGPGKRPLRGGFSDKERQDHRRRKALEMKRKQLAAGGKHLSKEEEELKRLTEEDERR  119
_genotype2   VDSGPRKKPHKSGFTDKERQDHRRRKALQMKKMQLSAGGKSLSKEEEELRRLTIEDDER  119
_genotype3   VDSGPGRKPKARGFTDQERRDHRRRKALEMKKKQLAGGGKHLSQEEEELRRLARDDDER  119
              :****  :*    **:**:********:**::**:.***.**:*****:**:  :*

_genotype1   ERRTAGPSVGGVMPLEGGSRG  140
_genotype2   QRRVAGPRVGDVMPPGGSPRG  140
_genotype3   ERRTAGPRPGGVMPMDGPPRG  140
              :**.***  .*:**  **  **
```

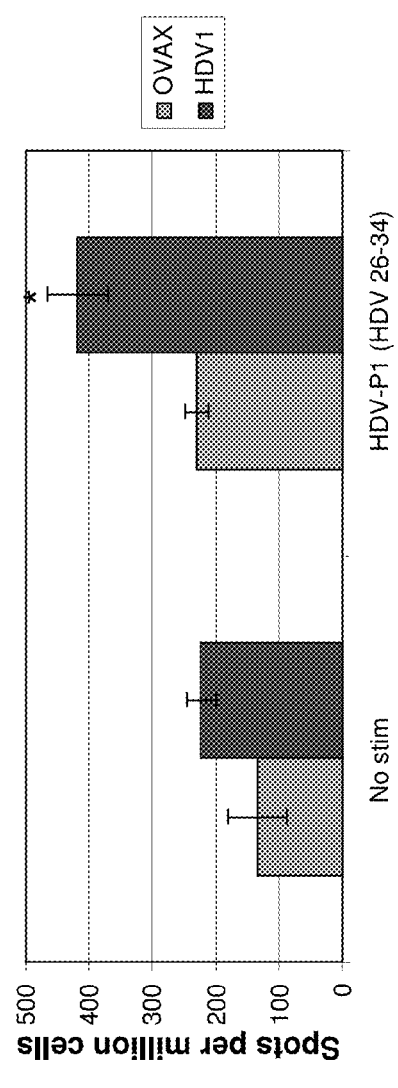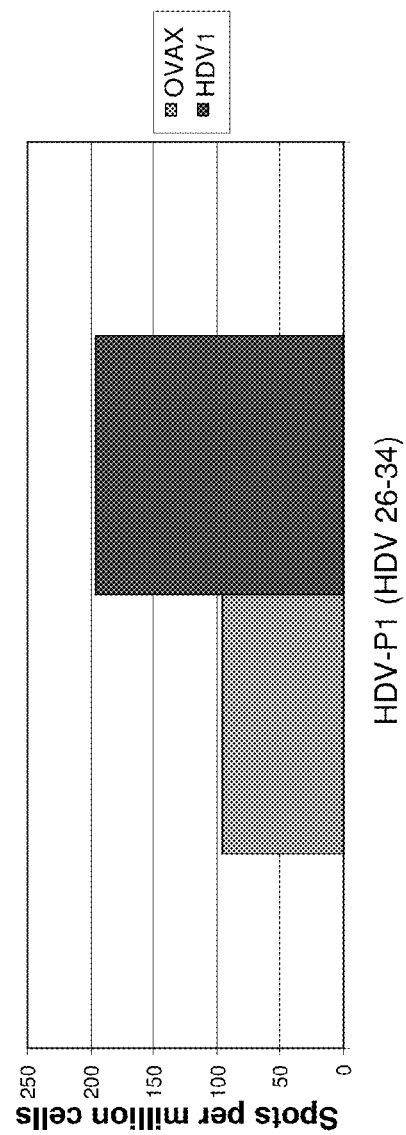

SEQUENCE LISTING

<160> NUMBER OF SEQ ID NOS: 36

<210> SEQ ID NO 1
<211> LENGTH: 1676
<212> TYPE: DNA
<213> ORGANISM: Hepatitis D virus

<400> SEQUENCE: 1
catgggccat ctccgagcga aggggcgcg ctggaagggt cggctcccga gagggataaa    60

```
acggtaaaga gcgttggatc tctgagggta gaacccccaa gaagaaaaaa agagaaagca    120
agagacggac gatttcccca tgactctgga catcctggg aaggggaaag aaggaaggtg    180
gaaaagaagg agctgggcct cccgatccga ggggcccaac tgccaagttt ggagagcact    240
ccggccgaaa ggtcgaggta cccagaagga ggaatctcac ggagaaaagc agacaaatca    300
cctccagagg accccttcag cgaacagaga gctctgacgc gcgaggagta agcccatagc    360
gatagggaga gatgctagga gttagaggag accgaagcga ggaggaaagc aaagagagca    420
acggggctag tcggtgggtg ttccgccccc cgagagggga cgagtgaggc ttatcccggg    480
gaactcggcg aatcgtcccc acatagcagc tcccggagcc ccttccaaaa tgaccgaggg    540
gggtggctag aacgcgggg accagtgga gccatgggat gcccttcccg atgtccgatc    600
atctccctcc cccccgagtg tcgcccagga atggcgggac cccactcaac tggggtccgc    660
gttccatcct ttcttacctg atggccggca tggtcccagc ctccccggtg gcgccggctg    720
ggcaacattc gaaggggac cgtccctcgg taatggcgaa tgggaccag aagtctctct    780 agattcccag agagaatcga gagaaactg gctctccctt agccatccga gtggacgctc    840
gtcctccttc ggatgcccag gtcggaccgc gaggaggtgg agatgccatg ccgacccgaa    900
gaggaaagaa ggacgcgaga cacgaacccg tgagtggaaa cccgctttat tcactggggt    960
cgacaactct ggggagaaaa gggaggatcg gctgggaaga gtatatccta tgggaatccc    1020
tggtttcccc tcacgtccag cccctccccg gtcctggaga agggggactc cgggacgctt    1080
agcatgttgg ggacgaagcc gccccggggc gctcccctcg atccaccttc gaggggttc    1140 acaccccaa ccgacgggcc ggctgttctt ctttcccttc tctcgtcttc ctcggtcaac    1200
ctcttaagtt cctcttcttc ttccttgctg aggtgcttcc ctcccgcggc cagctgcttt    1260
ctcttgttct cgagggcctt ccttcgtcgg tgatcctgcc tctccttgtc ggagaacct    1320 cccctgagag gcctcttccc aggcccggag tctatctcca tctggtccgt cgggccctc    1380 ttcgccgggg gagcccctc tccatcctta tctttctttc cgagaattcc tttgatgttt    1440
cccagccagg gattttcgtc ctcaagtttc ttgattttct tcttaatctt ccggaggtcc    1500
ctctcgagat cctctaactt cttcttccg tttacccact gctcgaggat cccctctctt    1560
ccgtcgcgat tcctcttcga ctcggaacgg ctcatctcga caagaggcga cggtcctcag    1620
tactcttact cttttctgta aagaggagac tgctggactc gacgcccgag ttcgag        1676
```

<210> SEQ ID NO 2
<211> LENGTH: 214
<212> TYPE: PRT
<213> ORGANISM: Hepatitis D virus

<400> SEQUENCE: 2

```
Met Ser Arg Ser Glu Ser Lys Arg Asn Arg Asp Gly Arg Glu Gly Ile
1               5                   10                  15

Leu Glu Gln Trp Val Asn Gly Arg Lys Lys Leu Glu Asp Leu Glu Arg
            20                  25                  30

Asp Leu Arg Lys Ile Lys Lys Ile Lys Lys Leu Glu Asp Glu Asn
        35                  40                  45

Pro Trp Leu Gly Asn Ile Lys Gly Ile Leu Gly Lys Lys Asp Lys Asp
    50                  55                  60

Gly Glu Gly Ala Pro Ala Lys Arg Ala Arg Thr Asp Gln Met Glu
65                  70                  75                  80

Ile Asp Ser Gly Pro Gly Lys Arg Pro Leu Arg Gly Gly Phe Ser Asp
```

```
                85                  90                  95
Lys Glu Arg Gln Asp His Arg Arg Lys Ala Leu Glu Asn Lys Arg
            100                 105                 110

Lys Gln Leu Ala Ala Gly Gly Lys His Leu Ser Lys Glu Glu Glu
            115                 120                 125

Glu Leu Lys Arg Leu Thr Glu Glu Asp Glu Arg Arg Glu Arg Thr
130                 135                 140

Ala Gly Pro Ser Val Gly Val Asn Pro Leu Glu Gly Gly Ser Arg
145                 150                 155                 160

Gly Ala Pro Gly Gly Gly Phe Val Pro Asn Met Leu Ser Val Pro Glu
            165                 170                 175

Ser Pro Phe Ser Arg Thr Gly Glu Gly Leu Asp Val Arg Gly Asn Gln
            180                 185                 190

Gly Phe Pro Trp Asp Ile Leu Phe Pro Ala Asp Pro Pro Phe Ser Pro
            195                 200                 205

Gln Ser Cys Arg Pro Gln
    210

<210> SEQ ID NO 3
<211> LENGTH: 195
<212> TYPE: PRT
<213> ORGANISM: Hepatitis D virus

<400> SEQUENCE: 3

Met Ser Arg Ser Glu Ser Lys Arg Asn Arg Asp Gly Arg Glu Gly Ile
1               5                   10                  15

Leu Glu Gln Trp Val Asn Gly Arg Lys Lys Leu Glu Asp Leu Glu Arg
            20                  25                  30

Asp Leu Arg Lys Ile Lys Lys Lys Ile Lys Lys Leu Glu Asp Glu Asn
            35                  40                  45

Pro Trp Leu Gly Asn Ile Lys Gly Ile Leu Gly Lys Lys Asp Lys Asp
50                  55                  60

Gly Glu Gly Ala Pro Pro Ala Lys Arg Ala Arg Thr Asp Gln Met Glu
65                  70                  75                  80

Ile Asp Ser Gly Pro Gly Lys Arg Pro Leu Arg Gly Gly Phe Ser Asp
            85                  90                  95

Lys Glu Arg Gln Asp His Arg Arg Lys Ala Leu Glu Asn Lys Arg
            100                 105                 110

Lys Gln Leu Ala Ala Gly Gly Lys His Leu Ser Lys Glu Glu Glu
            115                 120                 125

Glu Leu Lys Arg Leu Thr Glu Glu Asp Glu Arg Arg Glu Arg Thr
130                 135                 140

Ala Gly Pro Ser Val Gly Val Asn Pro Leu Glu Gly Gly Ser Arg
145                 150                 155                 160

Gly Ala Pro Gly Gly Gly Phe Val Pro Asn Met Leu Ser Val Pro Glu
            165                 170                 175

Ser Pro Phe Ser Arg Thr Gly Glu Gly Leu Asp Val Arg Gly Asn Gln
            180                 185                 190

Gly Phe Pro
    195

<210> SEQ ID NO 4
<211> LENGTH: 1688
<212> TYPE: DNA
<213> ORGANISM: Hepatitis D virus
```

<400> SEQUENCE: 4

```
atgggccgca agccgaacga aggattccgg taaggggaga ggaagaatcc cgaagggggtt      60
ccccactaaa gagtggaaga attctcggga agcttctccc aagaagaacc agaatccccc     120
aagagagaga atggatcccc atgacgctgg aagagactcc gggtaaccaa gtcaaggaga     180
aggaacggta gaaaagagcg agcctctcga tacgaaaggg ccgcgaccta tcaagtttgg     240
agtcatccgg gccaaagggt tgaaaaatcc cacagacggg agccaccagg agggatctag     300
gagaatccac ctccagagga ccccccctcaa tgaacagaag actctctacc tcggaggaaa     360
aagaccatag cgataggaag agatgctagg agtaggcggc gaccaaagcg aggaagaaag     420
taaagaaagc aacggggcta gcgagtggat gttccgcccc aaggggagcc gagtgaggct     480
tatcccgggg aactcggcgt atcgtcccga atgaggagc ccggatcccc ttccaaaaag     540
acggagaggg ggtgactagg aatcgggctc cggtggatcc gtgggaccag cccgctccac     600
ctccgcggca cactccttcc ccctgcgggg cccccccata agatggcagg aacccactca     660
ttggggtccg ctgttccatt ctttcttacc ttgtggccgg catggtccca gcctcctcgc     720
tggcgccggc tgggcaacat tccgagggga ccgtccctcg gtaatggcga atgggaccca     780
gaactctctc tagattccca gagagaatcg agagaaaact ggctctccct tagccatccg     840
agtaggacgt ctgtcctcct acggatgccc aggtcggacc gcgaggaggt ggagatgcca     900
tgccgacccg aagaggaaag aagaacacgg acgcgaaccc gtaagtggaa ccctgatcct     960
ttattgggggg gtacactcga ggagtggaag gcgctgcccg gggggagccg gattgaccta    1020
cgggaatccc cggtcgcctc tgatgtccag tccctccccc gtccgagaga agggagattc    1080
cggaactcca gtcatttgag ggacgaagcc gcccccgggc gctcccctcg gacttcctcc    1140
aggagggttc acatcccaa cccgcgggcc ggctactctt ctttgtcttt cgtcgtcttc    1200
aatggtcaac ctcctgagtt cctcttcttc ttccttgctg aggctctttc ccccgcgga    1260
gagttggttc ttcttgttct ggagggcctt ccttctgcgg tggtcctgcc tctccttgtc    1320
ggtgaacccg ctcttgtgag gtttcttcct aggtccggag tcgacctcca tctgatctgt    1380
tcgggccctc ttcgccgggg gagctccctc cccgtccttc cctttttctta tgattcccag    1440
gatgttcccc agccagggat tgtcatcctc gagtctcttg atggtctttc tggccttccg    1500
gaggtctctc tcgagctctt ccgccttttt tcttgtggat acccacttt cgaggatatc    1560
ttcccttcct ccccctccggc ttttcctcga ttcggattgg ctcatcctcg acgagggcga    1620
cggtcctcag ttctctctat tctttccttt tgaaagagga gactgctggt ccaaacgccc    1680
gagtcggg                                                             1688
```

<210> SEQ ID NO 5
<211> LENGTH: 214
<212> TYPE: PRT
<213> ORGANISM: Hepatitis D virus

<400> SEQUENCE: 5

```
Met Ser Gln Ser Glu Ser Arg Lys Ser Arg Arg Gly Gly Arg Glu Asp
1               5                   10                  15

Ile Leu Glu Lys Trp Val Ser Thr Arg Lys Lys Ala Glu Glu Leu Glu
            20                  25                  30

Arg Asp Leu Arg Lys Ala Arg Lys Thr Ile Lys Arg Leu Glu Asp Asp
        35                  40                  45

Asn Pro Trp Leu Gly Asn Ile Leu Gly Ile Ile Arg Lys Gly Lys Asp
    50                  55                  60
```

```
Gly Glu Gly Ala Pro Pro Ala Lys Arg Ala Arg Thr Asp Gln Met Glu
 65                  70                  75                  80

Val Asp Ser Gly Pro Arg Lys Lys Pro His Lys Ser Gly Phe Thr Asp
                 85                  90                  95

Lys Glu Arg Gln Asp His Arg Arg Lys Ala Leu Gln Asn Lys Lys
            100                 105                 110

Asn Gln Leu Ser Ala Gly Gly Lys Ser Leu Ser Lys Glu Glu Glu Glu
            115                 120                 125

Glu Leu Arg Arg Leu Thr Ile Glu Asp Asp Glu Arg Gln Arg Arg Val
130                 135                 140

Ala Gly Pro Arg Val Gly Asp Val Asn Pro Pro Gly Gly Ser Pro Arg
145                 150                 155                 160

Gly Ala Pro Gly Gly Gly Phe Val Pro Gln Met Thr Gly Val Pro Glu
                165                 170                 175

Ser Pro Phe Ser Arg Thr Gly Glu Gly Leu Asp Ile Arg Gly Asp Arg
            180                 185                 190

Gly Phe Pro Trp Val Asn Pro Ala Pro Pro Gly Gln Arg Leu Pro Leu
            195                 200                 205

Leu Glu Cys Thr Pro Gln
    210

<210> SEQ ID NO 6
<211> LENGTH: 195
<212> TYPE: PRT
<213> ORGANISM: Hepatitis D virus

<400> SEQUENCE: 6

Met Ser Gln Ser Glu Ser Arg Lys Ser Arg Gly Gly Arg Glu Asp
 1               5                  10                  15

Ile Leu Glu Lys Trp Val Ser Thr Arg Lys Ala Glu Glu Leu Glu
                 20                  25                  30

Arg Asp Leu Arg Lys Ala Arg Lys Thr Ile Lys Arg Leu Glu Asp Asp
            35                  40                  45

Asn Pro Trp Leu Gly Asn Ile Leu Gly Ile Ile Arg Lys Gly Lys Asp
 50                  55                  60

Gly Glu Gly Ala Pro Pro Ala Lys Arg Ala Arg Thr Asp Gln Met Glu
 65                  70                  75                  80

Val Asp Ser Gly Pro Arg Lys Lys Pro His Lys Ser Gly Phe Thr Asp
                 85                  90                  95

Lys Glu Arg Gln Asp His Arg Arg Lys Ala Leu Gln Asn Lys Lys
            100                 105                 110

Asn Gln Leu Ser Ala Gly Gly Lys Ser Leu Ser Lys Glu Glu Glu Glu
            115                 120                 125

Glu Leu Arg Arg Leu Thr Ile Glu Asp Asp Glu Arg Gln Arg Arg Val
130                 135                 140

Ala Gly Pro Arg Val Gly Asp Val Asn Pro Pro Gly Gly Ser Pro Arg
145                 150                 155                 160

Gly Ala Pro Gly Gly Gly Phe Val Pro Gln Met Thr Gly Val Pro Glu
                165                 170                 175

Ser Pro Phe Ser Arg Thr Gly Glu Gly Leu Asp Ile Arg Gly Asp Arg
            180                 185                 190

Gly Phe Pro
    195
```

<210> SEQ ID NO 7
<211> LENGTH: 1677
<212> TYPE: DNA
<213> ORGANISM: Hepatitis D virus

<400> SEQUENCE: 7

```
tgggccgctt ccggcaaggg ggtccgaaat cgagagcggg ggagaactcc cgagagttgg      60
gagaagaaag agggcgaaaa ttctcggacg gatcccccaa gctcccaaca gaggaagaga     120
acaagataga ggagccccca cgacgctagc aaaccgtcgc gcactgggag aggagtgggc     180
ggaagataga aacggagacc ccggtccgaa tgccaatcgg cagcaaactc ctctggagtc     240
ctccgggccg aaaggagaaa actaccggcg gagggtgatc caccccggagt tgaacggaca     300
agccacatcc agaggacccc ttcggcgaac agaagaccct ggtaccggga gggaatagcc     360
catagtacaa ggggagatgc taggagtcgg aggaagccag aacgactgag aaagcaaaga     420
gagcaacggg gctagccacc gggtgttcca tccatgggat cggtgccgag tgaggcttat     480
cccgggggtg acgcctcggc ccttccttag catcggaatc ccgggccccc tcccaggaat     540
gggaacaggg ggagatcgac cggggcccgc aggacccgat ggagttcccc caccatccct     600
tccggacgaa aactggtccc gatagggggca cccacaatag gatggcaaaa ggggactctc     660
gggtccgtcg ttccatcctt ttcttacctc gtggccggca tggccccagc ctcctcgctg     720
gcgccggctg ggcaacgatc cgagggagct actcctctcg agaatcggca aatggggccc     780
ctcgctcgta tctccgagag gagacgagaa ggaggtggat ctcccttttgc catccgaggg     840
agctacgctc tccttacgga tgcccaggtc ggaccgcgag gaggtggaga tcccatgccg     900
acccgaagag gaaaggagga cacggacgac aaaccgtgag ttctattgcc ctttattgtt     960
gggtgcaccc tgggacccag taatacccgg ggggaggcgg ggtaaaccca tactatggga    1020
actgctgggt tcctcggatg tcgatcccct ctcccgttcg ggaaaagggg gactccggaa    1080
ctccctgcag gctgggcacg aagccccac cgggcgctcc cctcggcggg ccgtccattg    1140
ggttcacacc cccaggtcgc gggccggctg ttcttcttttc tctttcgtcg tcatccctgg    1200
ccagcctccg gagttcctct tcttcctctt ggctgaggtg cttttccccct ccggccagtt    1260
gcttcttctt gttctccagg gccttccttc ttctgtggtc ccgcctctcc tggtcggtga    1320
accccctggc cttgggtttc ctcccaggtc cggaatcaac ctccatggtt cctgcctcg    1380
gcctcttcgc cggggcgct ccgtcttcgt ccttcttcct tctcaacagt ccaacgacgt    1440
tccctagcca ggggttctca tcctcaagtt tcttgatctt cttgttggct cgccggagat    1500
ccttctcgag ctttcgcctg ttcttccttt cctctaccca ctgttcgagg atctcctctc    1560
tctccttcga ggtcagcctt gcgacggttt ggctcatcct gagaccgggg agcttcgacg    1620
atctcttatc tctcctaagg aggaaggagc tctcgaacgc ccccccggct cctcgga       1677
```

<210> SEQ ID NO 8
<211> LENGTH: 214
<212> TYPE: PRT
<213> ORGANISM: Hepatitis D virus

<400> SEQUENCE: 8

Met Ser Gln Thr Val Ala Arg Leu Thr Ser Lys Glu Arg Glu Ile
1               5                   10                  15

Leu Glu Gln Trp Val Glu Glu Arg Lys Asn Arg Lys Leu Glu Lys
                20                  25                  30

Asp Leu Arg Arg Ala Asn Lys Lys Ile Lys Lys Leu Glu Asp Glu Asn
            35                  40                  45

```
Pro Trp Leu Gly Asn Val Val Gly Leu Leu Arg Arg Lys Lys Asp Glu
            50                   55                   60

Asp Gly Ala Pro Pro Ala Lys Arg Pro Arg Gln Glu Thr Met Glu Val
 65                   70                   75                   80

Asp Ser Gly Pro Gly Arg Lys Pro Lys Ala Arg Gly Phe Thr Asp Gln
                     85                   90                   95

Glu Arg Arg Asp His Arg Arg Lys Ala Leu Glu Asn Lys Lys
                100                 105                 110

Gln Leu Ala Gly Gly Lys His Leu Ser Gln Glu Glu Glu Glu
            115                 120                 125

Leu Arg Arg Leu Ala Arg Asp Asp Glu Arg Glu Arg Thr Ala
            130                 135                 140

Gly Pro Arg Pro Gly Gly Val Asn Pro Met Asp Gly Pro Pro Arg Gly
145                 150                 155                 160

Ala Pro Gly Gly Gly Phe Val Pro Ser Leu Gln Gly Val Pro Glu Ser
                    165                 170                 175

Pro Phe Ser Arg Thr Gly Glu Gly Ile Asp Ile Arg Gly Thr Gln Gln
                180                 185                 190

Phe Pro Trp Tyr Gly Phe Thr Pro Pro Pro Gly Tyr Tyr Trp Val
            195                 200                 205

Pro Gly Cys Thr Gln Gln
            210

<210> SEQ ID NO 9
<211> LENGTH: 195
<212> TYPE: PRT
<213> ORGANISM: Hepatitis D virus

<400> SEQUENCE: 9

Met Ser Gln Thr Val Ala Arg Leu Thr Ser Lys Glu Arg Glu Glu Ile
  1               5                  10                  15

Leu Glu Gln Trp Val Glu Glu Arg Lys Asn Arg Arg Lys Leu Glu Lys
                 20                  25                  30

Asp Leu Arg Arg Ala Asn Lys Lys Ile Lys Lys Leu Glu Asp Glu Asn
             35                  40                  45

Pro Trp Leu Gly Asn Val Val Gly Leu Leu Arg Arg Lys Lys Asp Glu
 50                  55                  60

Asp Gly Ala Pro Pro Ala Lys Arg Pro Arg Gln Glu Thr Met Glu Val
 65                  70                  75                  80

Asp Ser Gly Pro Gly Arg Lys Pro Lys Ala Arg Gly Phe Thr Asp Gln
                     85                  90                  95

Glu Arg Arg Asp His Arg Arg Lys Ala Leu Glu Asn Lys Lys
                100                 105                 110

Gln Leu Ala Gly Gly Lys His Leu Ser Gln Glu Glu Glu Glu
            115                 120                 125

Leu Arg Arg Leu Ala Arg Asp Asp Glu Arg Glu Arg Thr Ala
            130                 135                 140

Gly Pro Arg Pro Gly Gly Val Asn Pro Met Asp Gly Pro Pro Arg Gly
145                 150                 155                 160

Ala Pro Gly Gly Gly Phe Val Pro Ser Leu Gln Gly Val Pro Glu Ser
                    165                 170                 175

Pro Phe Ser Arg Thr Gly Glu Gly Ile Asp Ile Arg Gly Thr Gln Gln
                180                 185                 190

Phe Pro Trp
```

<210> SEQ ID NO 10
<211> LENGTH: 140
<212> TYPE: PRT
<213> ORGANISM: Artificial
<220> FEATURE:
<223> OTHER INFORMATION: Synthetic construct

<400> SEQUENCE: 10

Asn Gly Arg Lys Lys Leu Glu Asp Leu Glu Arg Asp Leu Arg Lys Ile
1               5                   10                  15

Lys Lys Lys Ile Lys Lys Leu Glu Asp Glu Asn Pro Trp Leu Gly Asn
            20                  25                  30

Ile Lys Gly Ile Leu Gly Lys Lys Asp Lys Asp Gly Glu Gly Ala Pro
        35                  40                  45

Pro Ala Lys Arg Ala Arg Thr Asp Gln Met Glu Ile Asp Ser Gly Pro
    50                  55                  60

Gly Lys Arg Pro Leu Arg Gly Gly Phe Ser Asp Lys Glu Arg Gln Asp
65              70                  75                  80

His Arg Arg Arg Lys Ala Leu Glu Asn Lys Arg Lys Gln Leu Ala Ala
                85                  90                  95

Gly Gly Lys His Leu Ser Lys Glu Glu Glu Glu Leu Lys Arg Leu
            100                 105                 110

Thr Glu Glu Asp Glu Arg Arg Glu Arg Arg Thr Ala Gly Pro Ser Val
        115                 120                 125

Gly Gly Val Asn Pro Leu Glu Gly Gly Ser Arg Gly
    130                 135                 140

<210> SEQ ID NO 11
<211> LENGTH: 6
<212> TYPE: PRT
<213> ORGANISM: Artificial
<220> FEATURE:
<223> OTHER INFORMATION: Synthetic construct

<400> SEQUENCE: 11

Met Ala Asp Glu Ala Pro
1               5

<210> SEQ ID NO 12
<211> LENGTH: 152
<212> TYPE: PRT
<213> ORGANISM: Artificial
<220> FEATURE:
<223> OTHER INFORMATION: Synthetic construct

<400> SEQUENCE: 12

Met Ala Asp Glu Ala Pro Asn Gly Arg Lys Lys Leu Glu Asp Leu Glu
1               5                   10                  15

Arg Asp Leu Arg Lys Ile Lys Lys Lys Ile Lys Lys Leu Glu Asp Glu
            20                  25                  30

Asn Pro Trp Leu Gly Asn Ile Lys Gly Ile Leu Gly Lys Lys Asp Lys
        35                  40                  45

Asp Gly Glu Gly Ala Pro Pro Ala Lys Arg Ala Arg Thr Asp Gln Met
    50                  55                  60

Glu Ile Asp Ser Gly Pro Gly Lys Arg Pro Leu Arg Gly Gly Phe Ser
65              70                  75                  80

Asp Lys Glu Arg Gln Asp His Arg Arg Arg Lys Ala Leu Glu Asn Lys
                85                  90                  95

```
Arg Lys Gln Leu Ala Gly Gly Lys His Leu Ser Lys Glu Glu Glu
            100                 105                 110

Glu Glu Leu Lys Arg Leu Thr Glu Asp Glu Arg Glu Arg Glu Arg
        115                 120                 125

Thr Ala Gly Pro Ser Val Gly Val Asn Pro Leu Glu Gly Gly Ser
    130                 135                 140

Arg Gly His His His His His His
145                 150

<210> SEQ ID NO 13
<211> LENGTH: 89
<212> TYPE: PRT
<213> ORGANISM: Saccharomyces cerevisiae

<400> SEQUENCE: 13

Met Arg Phe Pro Ser Ile Phe Thr Ala Val Leu Phe Ala Ala Ser
1               5                   10                  15

Ala Ser Ala Ala Pro Val Asn Thr Thr Thr Glu Asp Glu Thr Ala Gln
                20                  25                  30

Ile Pro Ala Glu Ala Val Ile Gly Tyr Leu Asp Leu Glu Gly Asp Phe
            35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Asp Lys Arg Glu Ala Glu Ala
                85

<210> SEQ ID NO 14
<211> LENGTH: 89
<212> TYPE: PRT
<213> ORGANISM: Saccharomyces cerevisiae

<400> SEQUENCE: 14

Met Arg Phe Pro Ser Ile Phe Thr Ala Val Leu Phe Ala Ala Ser
1               5                   10                  15

Ala Leu Ala Ala Pro Val Asn Thr Thr Thr Glu Asp Glu Thr Ala Gln
                20                  25                  30

Ile Pro Ala Glu Ala Val Ile Gly Tyr Leu Asp Leu Glu Gly Asp Phe
            35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Asp Lys Arg Glu Ala Glu Ala
                85

<210> SEQ ID NO 15
<211> LENGTH: 235
<212> TYPE: PRT
<213> ORGANISM: Artificial
<220> FEATURE:
<223> OTHER INFORMATION: Synthetic construct

<400> SEQUENCE: 15

Met Arg Phe Pro Ser Ile Phe Thr Ala Val Leu Phe Ala Ala Ser
1               5                   10                  15

Ala Ser Ala Ala Pro Val Asn Thr Thr Thr Glu Asp Glu Thr Ala Gln
```

```
            20                  25                  30
Ile Pro Ala Glu Ala Val Ile Gly Tyr Leu Asp Leu Glu Gly Asp Phe
        35                  40                  45

Asp Val Ala Val Leu Pro Phe Ser Asn Ser Thr Asn Asn Gly Leu Leu
 50                  55                  60

Phe Ile Asn Thr Thr Ile Ala Ser Ile Ala Ala Lys Glu Glu Gly Val
65                  70                  75                  80

Ser Leu Asp Lys Arg Glu Ala Glu Ala Asn Gly Arg Lys Lys Leu Glu
                85                  90                  95

Asp Leu Glu Arg Asp Leu Arg Lys Ile Lys Lys Ile Lys Lys Leu
            100                 105                 110

Glu Asp Glu Asn Pro Trp Leu Gly Asn Ile Lys Gly Ile Leu Gly Lys
            115                 120                 125

Lys Asp Lys Asp Gly Glu Gly Ala Pro Pro Ala Lys Arg Ala Arg Thr
        130                 135                 140

Asp Gln Met Glu Ile Asp Ser Gly Pro Gly Lys Arg Pro Leu Arg Gly
145                 150                 155                 160

Gly Phe Ser Asp Lys Glu Arg Gln Asp His Arg Arg Lys Ala Leu
                165                 170                 175

Glu Asn Lys Arg Lys Gln Leu Ala Ala Gly Gly Lys His Leu Ser Lys
            180                 185                 190

Glu Glu Glu Glu Leu Lys Arg Leu Thr Glu Glu Asp Glu Arg Arg
        195                 200                 205

Glu Arg Arg Thr Ala Gly Pro Ser Val Gly Gly Val Asn Pro Leu Glu
        210                 215                 220

Gly Gly Ser Arg Gly His His His His His
225                 230                 235

<210> SEQ ID NO 16
<211> LENGTH: 420
<212> TYPE: PRT
<213> ORGANISM: Artificial
<220> FEATURE:
<223> OTHER INFORMATION: Synthetic construct

<400> SEQUENCE: 16

Asn Gly Arg Lys Lys Leu Glu Asp Leu Glu Arg Asp Leu Arg Lys Ile
1               5                   10                  15

Lys Lys Ile Lys Lys Leu Glu Asp Glu Asn Pro Trp Leu Gly Asn
            20                  25                  30

Ile Lys Gly Ile Leu Gly Lys Lys Asp Lys Asp Gly Glu Gly Ala Pro
        35                  40                  45

Pro Ala Lys Arg Ala Arg Thr Asp Gln Met Glu Ile Asp Ser Gly Pro
 50                  55                  60

Gly Lys Arg Pro Leu Arg Gly Gly Phe Ser Asp Lys Glu Arg Gln Asp
65                  70                  75                  80

His Arg Arg Arg Lys Ala Leu Glu Asn Lys Arg Lys Gln Leu Ala Ala
                85                  90                  95

Gly Gly Lys His Leu Ser Lys Glu Glu Glu Glu Leu Lys Arg Leu
            100                 105                 110

Thr Glu Glu Asp Glu Arg Arg Glu Arg Arg Thr Ala Gly Pro Ser Val
        115                 120                 125

Gly Gly Val Asn Pro Leu Glu Gly Gly Ser Arg Gly Val Ser Thr Arg
        130                 135                 140

Lys Lys Ala Glu Glu Leu Glu Arg Asp Leu Arg Lys Ala Arg Lys Thr
```

```
                145                 150                 155                 160
    Ile Lys Arg Leu Glu Asp Asp Asn Pro Trp Leu Gly Asn Ile Leu Gly
                    165                 170                 175

Ile Ile Arg Lys Gly Lys Asp Gly Glu Gly Ala Pro Pro Ala Lys Arg
                    180                 185                 190

Ala Arg Thr Asp Gln Met Glu Val Asp Ser Gly Pro Arg Lys Lys Pro
                    195                 200                 205

His Lys Ser Gly Phe Thr Asp Lys Glu Arg Gln Asp His Arg Arg Arg
                    210                 215                 220

Lys Ala Leu Gln Asn Lys Lys Asn Gln Leu Ser Ala Gly Gly Lys Ser
    225                 230                 235                 240

Leu Ser Lys Glu Glu Glu Glu Leu Arg Arg Leu Thr Ile Glu Asp
                    245                 250                 255

Asp Glu Arg Gln Arg Arg Val Ala Gly Pro Arg Val Gly Asp Val Asn
                    260                 265                 270

Pro Pro Gly Gly Ser Pro Arg Gly Val Glu Glu Arg Lys Asn Arg Arg
                    275                 280                 285

Lys Leu Glu Lys Asp Leu Arg Arg Ala Asn Lys Lys Ile Lys Lys Leu
                    290                 295                 300

Glu Asp Glu Asn Pro Trp Leu Gly Asn Val Val Gly Leu Leu Arg Arg
    305                 310                 315                 320

Lys Lys Asp Glu Asp Gly Ala Pro Pro Ala Lys Arg Pro Arg Gln Glu
                    325                 330                 335

Thr Met Glu Val Asp Ser Gly Pro Gly Arg Lys Pro Lys Ala Arg Gly
                    340                 345                 350

Phe Thr Asp Gln Glu Arg Arg Asp His Arg Arg Lys Ala Leu Glu
                    355                 360                 365

Asn Lys Lys Lys Gln Leu Ala Gly Gly Lys His Leu Ser Gln Glu
                    370                 375                 380

Glu Glu Glu Leu Arg Arg Leu Ala Arg Asp Asp Asp Glu Arg Glu
    385                 390                 395                 400

Arg Arg Thr Ala Gly Pro Arg Pro Gly Gly Val Asn Pro Met Asp Gly
                    405                 410                 415

Pro Pro Arg Gly
                    420

<210> SEQ ID NO 17
<211> LENGTH: 432
<212> TYPE: PRT
<213> ORGANISM: Artificial
<220> FEATURE:
<223> OTHER INFORMATION: Synthetic construct

<400> SEQUENCE: 17

Met Ala Asp Glu Ala Pro Asn Gly Arg Lys Lys Leu Glu Asp Leu Glu
1               5                   10                  15

Arg Asp Leu Arg Lys Ile Lys Lys Lys Ile Lys Lys Leu Glu Asp Glu
                20                  25                  30

Asn Pro Trp Leu Gly Asn Ile Lys Gly Ile Leu Gly Lys Lys Asp Lys
            35                  40                  45

Asp Gly Glu Gly Ala Pro Pro Ala Lys Arg Ala Arg Thr Asp Gln Met
        50                  55                  60

Glu Ile Asp Ser Gly Pro Gly Lys Arg Pro Leu Arg Gly Gly Phe Ser
65                  70                  75                  80

Asp Lys Glu Arg Gln Asp His Arg Arg Arg Lys Ala Leu Glu Asn Lys
```

```
                        85                  90                  95
Arg Lys Gln Leu Ala Gly Gly Lys His Leu Ser Lys Glu Glu
            100                 105                 110

Glu Glu Leu Lys Arg Leu Thr Glu Glu Asp Glu Arg Glu Arg Arg
        115                 120                 125

Thr Ala Gly Pro Ser Val Gly Val Asn Pro Leu Glu Gly Gly Ser
    130                 135                 140

Arg Gly Val Ser Thr Arg Lys Lys Ala Glu Glu Leu Glu Arg Asp Leu
145                 150                 155                 160

Arg Lys Ala Arg Lys Thr Ile Lys Arg Leu Glu Asp Asp Asn Pro Trp
                165                 170                 175

Leu Gly Asn Ile Leu Gly Ile Ile Arg Lys Gly Lys Asp Gly Glu Gly
            180                 185                 190

Ala Pro Pro Ala Lys Arg Ala Arg Thr Asp Gln Met Glu Val Asp Ser
        195                 200                 205

Gly Pro Arg Lys Lys Pro His Lys Ser Gly Phe Thr Asp Lys Glu Arg
    210                 215                 220

Gln Asp His Arg Arg Lys Ala Leu Gln Asn Lys Lys Asn Gln Leu
225                 230                 235                 240

Ser Ala Gly Gly Lys Ser Leu Ser Lys Glu Glu Glu Glu Leu Arg
                245                 250                 255

Arg Leu Thr Ile Glu Asp Asp Glu Arg Gln Arg Arg Val Ala Gly Pro
            260                 265                 270

Arg Val Gly Asp Val Asn Pro Pro Gly Gly Ser Pro Arg Gly Val Glu
        275                 280                 285

Glu Arg Lys Asn Arg Arg Lys Leu Glu Lys Asp Leu Arg Arg Ala Asn
    290                 295                 300

Lys Lys Ile Lys Lys Leu Glu Asp Glu Asn Pro Trp Leu Gly Asn Val
305                 310                 315                 320

Val Gly Leu Leu Arg Arg Lys Asp Glu Asp Gly Ala Pro Pro Ala
                325                 330                 335

Lys Arg Pro Arg Gln Glu Thr Met Glu Val Asp Ser Gly Pro Gly Arg
            340                 345                 350

Lys Pro Lys Ala Arg Gly Phe Thr Asp Gln Glu Arg Arg Asp His Arg
        355                 360                 365

Arg Arg Lys Ala Leu Glu Asn Lys Lys Gln Leu Ala Gly Gly Gly
    370                 375                 380

Lys His Leu Ser Gln Glu Glu Glu Glu Leu Arg Arg Leu Ala Arg
385                 390                 395                 400

Asp Asp Asp Glu Arg Glu Arg Arg Thr Ala Gly Pro Arg Pro Gly Gly
                405                 410                 415

Val Asn Pro Met Asp Gly Pro Pro Arg Gly His His His His His
            420                 425                 430

<210> SEQ ID NO 18
<211> LENGTH: 515
<212> TYPE: PRT
<213> ORGANISM: Artificial
<220> FEATURE:
<223> OTHER INFORMATION: Synthetic construct

<400> SEQUENCE: 18

Met Arg Phe Pro Ser Ile Phe Thr Ala Val Leu Phe Ala Ala Ser Ser
1               5                   10                  15

Ala Ser Ala Ala Pro Val Asn Thr Thr Thr Glu Asp Glu Thr Ala Gln
```

```
                20                  25                  30
Ile Pro Ala Glu Ala Val Ile Gly Tyr Leu Asp Leu Glu Gly Asp Phe
            35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Asp Lys Arg Glu Ala Glu Ala Asn Gly Arg Lys Lys Leu Glu
                85                  90                  95

Asp Leu Glu Arg Asp Leu Arg Lys Ile Lys Lys Ile Lys Lys Leu
            100                 105                 110

Glu Asp Glu Asn Pro Trp Leu Gly Asn Ile Lys Gly Ile Leu Gly Lys
        115                 120                 125

Lys Asp Lys Asp Gly Glu Gly Ala Pro Ala Lys Arg Ala Arg Thr
    130                 135                 140

Asp Gln Met Glu Ile Asp Ser Gly Pro Gly Lys Arg Pro Leu Arg Gly
145                 150                 155                 160

Gly Phe Ser Asp Lys Glu Arg Gln Asp His Arg Arg Lys Ala Leu
                165                 170                 175

Glu Asn Lys Arg Lys Gln Leu Ala Ala Gly Gly Lys His Leu Ser Lys
            180                 185                 190

Glu Glu Glu Glu Leu Lys Arg Leu Thr Glu Glu Asp Glu Arg Arg
        195                 200                 205

Glu Arg Arg Thr Ala Gly Pro Ser Val Gly Val Asn Pro Leu Glu
    210                 215                 220

Gly Gly Ser Arg Gly Val Ser Thr Arg Lys Lys Ala Glu Glu Leu Glu
225                 230                 235                 240

Arg Asp Leu Arg Lys Ala Arg Lys Thr Ile Lys Arg Leu Glu Asp Asp
                245                 250                 255

Asn Pro Trp Leu Gly Asn Ile Leu Gly Ile Ile Arg Lys Gly Lys Asp
            260                 265                 270

Gly Glu Gly Ala Pro Pro Ala Lys Arg Ala Arg Thr Asp Gln Met Glu
        275                 280                 285

Val Asp Ser Gly Pro Arg Lys Lys Pro His Lys Ser Gly Phe Thr Asp
    290                 295                 300

Lys Glu Arg Gln Asp His Arg Arg Lys Ala Leu Gln Asn Lys Lys
305                 310                 315                 320

Asn Gln Leu Ser Ala Gly Gly Lys Ser Leu Ser Lys Glu Glu Glu Glu
                325                 330                 335

Glu Leu Arg Arg Leu Thr Ile Glu Asp Asp Glu Arg Gln Arg Val
            340                 345                 350

Ala Gly Pro Arg Val Gly Asp Val Asn Pro Gly Gly Ser Pro Arg
        355                 360                 365

Gly Val Glu Glu Arg Lys Asn Arg Arg Lys Leu Glu Lys Asp Leu Arg
    370                 375                 380

Arg Ala Asn Lys Lys Ile Lys Lys Leu Glu Asp Glu Asn Pro Trp Leu
385                 390                 395                 400

Gly Asn Val Val Gly Leu Leu Arg Lys Lys Asp Glu Asp Gly Ala
                405                 410                 415

Pro Pro Ala Lys Arg Pro Arg Gln Glu Thr Met Glu Val Asp Ser Gly
            420                 425                 430

Pro Gly Arg Lys Pro Lys Ala Arg Gly Phe Thr Asp Gln Glu Arg Arg
        435                 440                 445
```

```
Asp His Arg Arg Arg Lys Ala Leu Glu Asn Lys Lys Gln Leu Ala
        450                 455                 460

Gly Gly Gly Lys His Leu Ser Gln Glu Glu Glu Glu Leu Arg Arg
465                 470                 475                 480

Leu Ala Arg Asp Asp Asp Glu Arg Glu Arg Arg Thr Ala Gly Pro Arg
                485                 490                 495

Pro Gly Gly Val Asn Pro Met Asp Gly Pro Pro Arg Gly His His His
            500                 505                 510

His His His
        515

<210> SEQ ID NO 19
<211> LENGTH: 9
<212> TYPE: PRT
<213> ORGANISM: Hepatitis D virus

<400> SEQUENCE: 19

Lys Leu Glu Asp Glu Asn Pro Trp Leu
1               5

<210> SEQ ID NO 20
<211> LENGTH: 9
<212> TYPE: PRT
<213> ORGANISM: Hepatitis D virus

<400> SEQUENCE: 20

Lys Leu Glu Asp Leu Glu Arg Asp Leu
1               5

<210> SEQ ID NO 21
<211> LENGTH: 16
<212> TYPE: PRT
<213> ORGANISM: Hepatitis D virus

<400> SEQUENCE: 21

Lys Leu Glu Asp Leu Glu Arg Asp Leu Arg Lys Ile Lys Lys Lys Ile
1               5                   10                  15

<210> SEQ ID NO 22
<211> LENGTH: 16
<212> TYPE: PRT
<213> ORGANISM: Hepatitis D virus

<400> SEQUENCE: 22

Trp Leu Gly Asn Ile Lys Gly Ile Leu Gly Lys Lys Asp Lys Asp Gly
1               5                   10                  15

<210> SEQ ID NO 23
<211> LENGTH: 16
<212> TYPE: PRT
<213> ORGANISM: Hepatitis D virus

<400> SEQUENCE: 23

Ala Gly Ala Pro Pro Ala Lys Arg Ala Arg Thr Asp Gln Met Glu Ile
1               5                   10                  15

<210> SEQ ID NO 24
<211> LENGTH: 16
<212> TYPE: PRT
<213> ORGANISM: Hepatitis D virus

<400> SEQUENCE: 24
```

Ala Arg Thr Asp Gln Met Glu Ile Asp Ser Gly Pro Gly Lys Arg Pro
1               5                   10                  15

<210> SEQ ID NO 25
<211> LENGTH: 16
<212> TYPE: PRT
<213> ORGANISM: Hepatitis D virus

<400> SEQUENCE: 25

Lys Ala Leu Glu Asn Lys Arg Lys Gln Leu Ala Ala Gly Gly Lys His
1               5                   10                  15

<210> SEQ ID NO 26
<211> LENGTH: 32
<212> TYPE: PRT
<213> ORGANISM: Hepatitis D virus

<400> SEQUENCE: 26

Leu Ser Lys Glu Glu Glu Glu Leu Lys Arg Leu Thr Glu Glu Asp
1               5                   10                  15

Glu Arg Arg Glu Arg Arg Thr Ala Gly Pro Ser Val Gly Gly Val Asn
            20                  25                  30

<210> SEQ ID NO 27
<211> LENGTH: 10
<212> TYPE: PRT
<213> ORGANISM: Hepatitis D virus

<400> SEQUENCE: 27

Ala Gly Ala Pro Pro Ala Lys Arg Ala Arg
1               5                   10

<210> SEQ ID NO 28
<211> LENGTH: 204
<212> TYPE: PRT
<213> ORGANISM: Artificial
<220> FEATURE:
<223> OTHER INFORMATION: synthetic construct

<400> SEQUENCE: 28

Met Ser Arg Ser Glu Ser Lys Arg Asn Arg Asp Gly Arg Glu Gly Ile
1               5                   10                  15

Leu Glu Gln Trp Val Asn Gly Arg Lys Lys Leu Glu Asp Leu Glu Arg
            20                  25                  30

Asp Leu Arg Lys Ile Lys Lys Lys Ile Lys Lys Leu Glu Asp Glu Asn
        35                  40                  45

Pro Trp Leu Gly Asn Ile Lys Gly Ile Leu Gly Lys Lys Asp Lys Asp
    50                  55                  60

Gly Thr Asp Gln Met Glu Ile Asp Ser Gly Pro Gly Lys Arg Pro Leu
65                  70                  75                  80

Arg Gly Gly Phe Ser Asp Lys Glu Arg Gln Asp His Arg Arg Arg Lys
                85                  90                  95

Ala Leu Glu Asn Lys Arg Lys Gln Leu Ala Ala Gly Gly Lys His Leu
            100                 105                 110

Ser Lys Glu Glu Glu Glu Glu Leu Lys Arg Leu Thr Glu Glu Asp Glu
        115                 120                 125

Arg Arg Glu Arg Arg Thr Ala Gly Pro Ser Val Gly Val Asn Pro
    130                 135                 140

Leu Glu Gly Gly Ser Arg Gly Ala Pro Gly Gly Phe Val Pro Asn
145                 150                 155                 160

```
Met Leu Ser Val Pro Glu Ser Pro Phe Ser Arg Thr Gly Glu Gly Leu
            165                 170                 175

Asp Val Arg Gly Asn Gln Gly Phe Pro Trp Asp Ile Leu Phe Pro Ala
        180                 185                 190

Asp Pro Pro Phe Ser Pro Gln Ser Cys Arg Pro Gln
    195                 200

<210> SEQ ID NO 29
<211> LENGTH: 677
<212> TYPE: DNA
<213> ORGANISM: Artificial
<220> FEATURE:
<223> OTHER INFORMATION: synthetic construct
<220> FEATURE:
<221> NAME/KEY: CDS
<222> LOCATION: (13)..(669)

<400> SEQUENCE: 29
gaattcgcca cc atg gct gac gaa gct cct act agt atg agt aga tct gaa      51
              Met Ala Asp Glu Ala Pro Thr Ser Met Ser Arg Ser Glu
                1               5                  10 tca aag aga aat aga gat ggc aga gag ggt att cta gaa caa tgg gtg        99
Ser Lys Arg Asn Arg Asp Gly Arg Glu Gly Ile Leu Glu Gln Trp Val
 15                  20                  25 aat ggt aga aag aaa tta gag gac ctc gaa cgt gac ctt aga aag att       147
Asn Gly Arg Lys Lys Leu Glu Asp Leu Glu Arg Asp Leu Arg Lys Ile
 30                  35                  40                  45 aag aag aaa atc aaa aag ctc gaa gat gaa aac cca tgg cta ggc aat       195
Lys Lys Lys Ile Lys Lys Leu Glu Asp Glu Asn Pro Trp Leu Gly Asn
                 50                  55                  60 atc aaa ggt atc tta ggt aaa aag gat aaa gac ggt aca gat caa atg       243
Ile Lys Gly Ile Leu Gly Lys Lys Asp Lys Asp Gly Thr Asp Gln Met
             65                  70                  75 gaa att gat tct ggc cca ggc aaa aga cct tta aga ggt gga ttc tct       291
Glu Ile Asp Ser Gly Pro Gly Lys Arg Pro Leu Arg Gly Gly Phe Ser
         80                  85                  90 gat aaa gag aga caa gat cat agg cga cgt aaa gcc cta gaa aat aag       339
Asp Lys Glu Arg Gln Asp His Arg Arg Arg Lys Ala Leu Glu Asn Lys
     95                 100                 105 aga aaa cag ttg gct gca ggg ggc aag cat ttg tca aag gag gag gaa       387
Arg Lys Gln Leu Ala Ala Gly Gly Lys His Leu Ser Lys Glu Glu Glu
110                 115                 120                 125 gag gaa ttg aaa aga ttg act gaa gag gat gaa cgt aga gaa aga cgt       435
Glu Glu Leu Lys Arg Leu Thr Glu Glu Asp Glu Arg Arg Glu Arg Arg
                130                 135                 140 aca gcg ggt cct tca gtc ggc ggt gtt aac cca tta gaa ggt ggt tca       483
Thr Ala Gly Pro Ser Val Gly Gly Val Asn Pro Leu Glu Gly Gly Ser
            145                 150                 155 aga gga gca cct gga gga gga ttc gta cca aac atg ttg tcc gtt cca       531
Arg Gly Ala Pro Gly Gly Gly Phe Val Pro Asn Met Leu Ser Val Pro
        160                 165                 170 gaa agc cca ttt tcc aga acc ggg gaa ggg ctg gac gtt aga ggt aat       579
Glu Ser Pro Phe Ser Arg Thr Gly Glu Gly Leu Asp Val Arg Gly Asn
    175                 180                 185 caa gga ttt cca tgg gat ata ctt ttt cca gca gat cca cca ttt tct       627
Gln Gly Phe Pro Trp Asp Ile Leu Phe Pro Ala Asp Pro Pro Phe Ser
190                 195                 200                 205 cct caa tct tgt agg cct cag cac cat cat cac cat cac tag gcggccgc     677
Pro Gln Ser Cys Arg Pro Gln His His His His His His
                210                 215
```

```
<210> SEQ ID NO 30
<211> LENGTH: 218
<212> TYPE: PRT
<213> ORGANISM: Artificial
<220> FEATURE:
<223> OTHER INFORMATION: Synthetic Construct

<400> SEQUENCE: 30

Met Ala Asp Glu Ala Pro Thr Ser Met Ser Arg Ser Glu Ser Lys Arg
1               5                   10                  15

Asn Arg Asp Gly Arg Glu Gly Ile Leu Glu Gln Trp Val Asn Gly Arg
            20                  25                  30

Lys Lys Leu Glu Asp Leu Glu Arg Asp Leu Arg Lys Ile Lys Lys Lys
        35                  40                  45

Ile Lys Lys Leu Glu Asp Glu Asn Pro Trp Leu Gly Asn Ile Lys Gly
    50                  55                  60

Ile Leu Gly Lys Lys Asp Lys Asp Gly Thr Asp Gln Met Glu Ile Asp
65                  70                  75                  80

Ser Gly Pro Gly Lys Arg Pro Leu Arg Gly Gly Phe Ser Asp Lys Glu
                85                  90                  95

Arg Gln Asp His Arg Arg Lys Ala Leu Glu Asn Lys Arg Lys Gln
            100                 105                 110

Leu Ala Ala Gly Gly Lys His Leu Ser Lys Glu Glu Glu Glu Glu Leu
        115                 120                 125

Lys Arg Leu Thr Glu Glu Asp Glu Arg Glu Arg Arg Thr Ala Gly
    130                 135                 140

Pro Ser Val Gly Val Asn Pro Leu Glu Gly Ser Arg Gly Ala
145                 150                 155                 160

Pro Gly Gly Gly Phe Val Pro Asn Met Leu Ser Val Pro Glu Ser Pro
                165                 170                 175

Phe Ser Arg Thr Gly Glu Gly Leu Asp Val Arg Gly Asn Gln Gly Phe
            180                 185                 190

Pro Trp Asp Ile Leu Phe Pro Ala Asp Pro Pro Phe Ser Pro Gln Ser
        195                 200                 205

Cys Arg Pro Gln His His His His His His
    210                 215

<210> SEQ ID NO 31
<211> LENGTH: 214
<212> TYPE: PRT
<213> ORGANISM: Artificial
<220> FEATURE:
<223> OTHER INFORMATION: synthetic construct

<400> SEQUENCE: 31

Met Ser Arg Ser Glu Ser Lys Arg Asn Arg Asp Gly Arg Glu Gly Ile
1               5                   10                  15

Leu Glu Gln Trp Val Asn Gly Arg Lys Lys Leu Glu Asp Leu Glu Arg
            20                  25                  30

Asp Leu Arg Lys Ile Lys Lys Lys Ile Lys Lys Leu Glu Asp Glu Asn
        35                  40                  45

Pro Trp Leu Gly Asn Ile Lys Gly Ile Leu Gly Lys Lys Asp Lys Asp
    50                  55                  60

Gly Ala Gly Ala Pro Pro Ala Lys Arg Ala Arg Thr Asp Gln Met Glu
65                  70                  75                  80

Ile Asp Ser Gly Pro Gly Lys Arg Pro Leu Arg Gly Gly Phe Ser Asp
                85                  90                  95
```

```
Lys Glu Arg Gln Asp His Arg Arg Lys Ala Leu Glu Asn Lys Arg
            100                 105                 110
Lys Gln Leu Ala Ala Gly Gly Lys His Leu Ser Lys Glu Glu Glu
            115                 120                 125
Glu Leu Lys Arg Leu Thr Glu Glu Asp Glu Arg Arg Glu Arg Arg Thr
130                 135                 140
Ala Gly Pro Ser Val Gly Val Asn Pro Leu Glu Gly Gly Ser Arg
145                 150                 155                 160
Gly Ala Pro Gly Gly Phe Val Pro Asn Met Leu Ser Val Pro Glu
                165                 170                 175
Ser Pro Phe Ser Arg Thr Gly Glu Gly Leu Asp Val Arg Gly Asn Gln
                180                 185                 190
Gly Phe Pro Trp Asp Ile Leu Phe Pro Ala Asp Pro Phe Ser Pro
                195                 200                 205
Gln Ser Cys Arg Pro Gln
    210
```

<210> SEQ ID NO 32
<211> LENGTH: 707
<212> TYPE: DNA
<213> ORGANISM: Artificial
<220> FEATURE:
<223> OTHER INFORMATION: synthetic construct
<220> FEATURE:
<221> NAME/KEY: CDS
<222> LOCATION: (13)..(699)

<400> SEQUENCE: 32

```
gaattcgcca cc atg gct gac gaa gct cct act agt atg agt aga tct gaa      51
              Met Ala Asp Glu Ala Pro Thr Ser Met Ser Arg Ser Glu
                1               5                   10 tca aag aga aat aga gat ggc aga gag ggt att cta gaa caa tgg gtg        99
Ser Lys Arg Asn Arg Asp Gly Arg Glu Gly Ile Leu Glu Gln Trp Val
     15                  20                  25 aat ggt aga aag aaa tta gag gac ctc gaa cgt gac ctt aga aag att       147
Asn Gly Arg Lys Lys Leu Glu Asp Leu Glu Arg Asp Leu Arg Lys Ile
 30                  35                  40                  45 aag aag aaa atc aaa aag ctc gaa gat gaa aac cca tgg cta ggc aat       195
Lys Lys Lys Ile Lys Lys Leu Glu Asp Glu Asn Pro Trp Leu Gly Asn
                 50                  55                  60 atc aaa ggt atc tta ggt aaa aag gat aaa gac ggt gcc ggt gcc cca       243
Ile Lys Gly Ile Leu Gly Lys Lys Asp Lys Asp Gly Ala Gly Ala Pro
             65                  70                  75 cct gct aaa aga gct aga aca gat caa atg gaa att gat tct ggc cca       291
Pro Ala Lys Arg Ala Arg Thr Asp Gln Met Glu Ile Asp Ser Gly Pro
         80                  85                  90 ggc aaa aga cct tta aga ggt gga ttc tct gat aaa gag aga caa gat       339
Gly Lys Arg Pro Leu Arg Gly Gly Phe Ser Asp Lys Glu Arg Gln Asp
     95                  100                 105 cat agg cga cgt aaa gcc cta gaa aat aag aga aaa cag ttg gct gca       387
His Arg Arg Arg Lys Ala Leu Glu Asn Lys Arg Lys Gln Leu Ala Ala
110                 115                 120                 125 ggg ggc aag cat ttg tca aag gag gag gaa gag gaa ttg aaa aga ttg       435
Gly Gly Lys His Leu Ser Lys Glu Glu Glu Glu Glu Leu Lys Arg Leu
                130                 135                 140 act gaa gag gat gaa cgt aga gaa aga cgt aca gcg ggt cct tca gtc       483
Thr Glu Glu Asp Glu Arg Arg Glu Arg Arg Thr Ala Gly Pro Ser Val
            145                 150                 155 ggc ggt gtt aac cca tta gaa ggt ggt tca aga gga gca cct gga gga       531
Gly Gly Val Asn Pro Leu Glu Gly Gly Ser Arg Gly Ala Pro Gly Gly
```

```
            160                 165                 170
gga ttc gta cca aac atg ttg tcc gtt cca gaa agc cca ttt tcc aga    579
Gly Phe Val Pro Asn Met Leu Ser Val Pro Glu Ser Pro Phe Ser Arg
175                 180                 185 acc ggg gaa ggg ctg gac gtt aga ggt aat caa gga ttt cca tgg gat    627
Thr Gly Glu Gly Leu Asp Val Arg Gly Asn Gln Gly Phe Pro Trp Asp
190                 195                 200                 205 ata ctt ttt cca gca gat cca cca ttt tct cct caa tct tgt agg cct    675
Ile Leu Phe Pro Ala Asp Pro Pro Phe Ser Pro Gln Ser Cys Arg Pro
                210                 215                 220 cag cac cat cat cac cat cac tag gcggccgc                           707
Gln His His His His His His
            225
```

<210> SEQ ID NO 33
<211> LENGTH: 228
<212> TYPE: PRT
<213> ORGANISM: Artificial
<220> FEATURE:
<223> OTHER INFORMATION: Synthetic Construct

<400> SEQUENCE: 33

```
Met Ala Asp Glu Ala Pro Thr Ser Met Ser Arg Ser Glu Ser Lys Arg
1               5                   10                  15

Asn Arg Asp Gly Arg Glu Gly Ile Leu Glu Gln Trp Val Asn Gly Arg
            20                  25                  30

Lys Lys Leu Glu Asp Leu Glu Arg Asp Leu Arg Lys Ile Lys Lys Lys
        35                  40                  45

Ile Lys Lys Leu Glu Asp Glu Asn Pro Trp Leu Gly Asn Ile Lys Gly
50                  55                  60

Ile Leu Gly Lys Lys Asp Lys Asp Gly Ala Gly Ala Pro Pro Ala Lys
65                  70                  75                  80

Arg Ala Arg Thr Asp Gln Met Glu Ile Asp Ser Gly Pro Gly Lys Arg
                85                  90                  95

Pro Leu Arg Gly Gly Phe Ser Asp Lys Glu Arg Gln Asp His Arg Arg
            100                 105                 110

Arg Lys Ala Leu Glu Asn Lys Arg Lys Gln Leu Ala Ala Gly Gly Lys
        115                 120                 125

His Leu Ser Lys Glu Glu Glu Glu Leu Lys Arg Leu Thr Glu Glu
130                 135                 140

Asp Glu Arg Arg Glu Arg Arg Thr Ala Gly Pro Ser Val Gly Gly Val
145                 150                 155                 160

Asn Pro Leu Glu Gly Gly Ser Arg Gly Ala Pro Gly Gly Gly Phe Val
                165                 170                 175

Pro Asn Met Leu Ser Val Pro Glu Ser Pro Phe Ser Arg Thr Gly Glu
            180                 185                 190

Gly Leu Asp Val Arg Gly Asn Gln Gly Phe Pro Trp Asp Ile Leu Phe
        195                 200                 205

Pro Ala Asp Pro Pro Phe Ser Pro Gln Ser Cys Arg Pro Gln His His
    210                 215                 220

His His His His
225
```

<210> SEQ ID NO 34
<211> LENGTH: 408
<212> TYPE: PRT
<213> ORGANISM: Artificial
<220> FEATURE:

<223> OTHER INFORMATION: synthetic construct

<400> SEQUENCE: 34

```
Met Ser Arg Ser Glu Ser Lys Arg Asn Arg Asp Gly Arg Glu Gly Ile
1               5                   10                  15

Leu Glu Gln Trp Val Asn Gly Arg Lys Lys Leu Glu Asp Leu Glu Arg
            20                  25                  30

Asp Leu Arg Lys Ile Lys Lys Ile Lys Lys Leu Glu Asp Glu Asn
        35                  40                  45

Pro Trp Leu Gly Asn Ile Lys Gly Ile Leu Gly Lys Lys Asp Lys Asp
    50                  55                  60

Gly Thr Asp Gln Met Glu Ile Asp Ser Gly Pro Gly Lys Arg Pro Leu
65                  70                  75                  80

Arg Gly Gly Phe Ser Asp Lys Glu Arg Gln Asp His Arg Arg Arg Lys
                85                  90                  95

Ala Leu Glu Asn Lys Arg Lys Gln Leu Ala Ala Gly Lys His Leu
            100                 105                 110

Ser Lys Glu Glu Glu Glu Leu Lys Arg Leu Thr Glu Glu Asp Glu
        115                 120                 125

Arg Arg Glu Arg Arg Thr Ala Gly Pro Ser Val Gly Val Asn Pro
130                 135                 140

Leu Glu Gly Gly Ser Arg Gly Ala Pro Gly Gly Phe Val Pro Asn
145                 150                 155                 160

Met Leu Ser Val Pro Glu Ser Pro Phe Ser Arg Thr Gly Glu Gly Leu
                165                 170                 175

Asp Val Arg Gly Asn Gln Gly Phe Pro Trp Asp Ile Leu Phe Pro Ala
            180                 185                 190

Asp Pro Pro Phe Ser Pro Gln Ser Cys Arg Pro Gln Met Ser Gln Ser
        195                 200                 205

Glu Ser Arg Lys Ser Arg Arg Gly Gly Arg Glu Asp Ile Leu Glu Lys
210                 215                 220

Trp Val Ser Thr Arg Lys Lys Ala Glu Glu Leu Glu Arg Asp Leu Arg
225                 230                 235                 240

Lys Ala Arg Lys Thr Ile Lys Arg Leu Glu Asp Asp Asn Pro Trp Leu
                245                 250                 255

Gly Asn Ile Leu Gly Ile Ile Arg Lys Gly Lys Asp Gly Thr Asp Gln
            260                 265                 270

Met Glu Val Asp Ser Gly Pro Arg Lys Lys Pro His Lys Ser Gly Phe
        275                 280                 285

Thr Asp Lys Glu Arg Gln Asp His Arg Arg Lys Ala Leu Gln Asn
290                 295                 300

Lys Lys Asn Gln Leu Ser Ala Gly Gly Lys Ser Leu Ser Lys Glu Glu
305                 310                 315                 320

Glu Glu Glu Leu Arg Arg Leu Thr Ile Glu Asp Asp Glu Arg Gln Arg
                325                 330                 335

Arg Val Ala Gly Pro Arg Val Gly Asp Val Asn Pro Gly Gly Ser
            340                 345                 350

Pro Arg Gly Ala Pro Gly Gly Gly Phe Val Pro Gln Met Thr Gly Val
        355                 360                 365

Pro Glu Ser Pro Phe Ser Arg Thr Gly Glu Gly Leu Asp Ile Arg Gly
370                 375                 380

Asp Arg Gly Phe Pro Trp Val Asn Pro Ala Pro Pro Gly Gln Arg Leu
385                 390                 395                 400
```

```
Pro Leu Leu Glu Cys Thr Pro Gln
            405
```

<210> SEQ ID NO 35
<211> LENGTH: 1292
<212> TYPE: DNA
<213> ORGANISM: Artificial
<220> FEATURE:
<223> OTHER INFORMATION: synthetic construct
<220> FEATURE:
<221> NAME/KEY: CDS
<222> LOCATION: (13)..(1284)

<400> SEQUENCE: 35

```
gaattcgcca cc atg gct gac gaa gct cct act agt atg agt aga tct gaa      51
              Met Ala Asp Glu Ala Pro Thr Ser Met Ser Arg Ser Glu
                1               5                  10 tca aag aga aat aga gat ggc aga gag ggt att cta gaa caa tgg gtg        99
Ser Lys Arg Asn Arg Asp Gly Arg Glu Gly Ile Leu Glu Gln Trp Val
 15                  20                  25 aat ggt aga aag aaa tta gag gac ctc gaa cgt gac ctt aga aag att      147
Asn Gly Arg Lys Lys Leu Glu Asp Leu Glu Arg Asp Leu Arg Lys Ile
 30                  35                  40                  45 aag aag aaa atc aaa aag ctc gaa gat gaa aac cca tgg cta ggc aat      195
Lys Lys Lys Ile Lys Lys Leu Glu Asp Glu Asn Pro Trp Leu Gly Asn
                 50                  55                  60 atc aaa ggt atc tta ggt aaa aag gat aaa gac ggt aca gat caa atg      243
Ile Lys Gly Ile Leu Gly Lys Lys Asp Lys Asp Gly Thr Asp Gln Met
             65                  70                  75 gaa att gat tct ggc cca ggc aaa aga cct tta aga ggt gga ttc tct      291
Glu Ile Asp Ser Gly Pro Gly Lys Arg Pro Leu Arg Gly Gly Phe Ser
         80                  85                  90 gat aaa gag aga caa gat cat agg cga cgt aaa gcc cta gaa aat aag      339
Asp Lys Glu Arg Gln Asp His Arg Arg Arg Lys Ala Leu Glu Asn Lys
     95                 100                 105 aga aaa cag ttg gct gca ggg ggc aag cat ttg tca aag gag gag gaa      387
Arg Lys Gln Leu Ala Ala Gly Gly Lys His Leu Ser Lys Glu Glu Glu
110                 115                 120                 125 gag gaa ttg aaa aga ttg act gaa gag gat gaa cgt aga gaa aga cgt      435
Glu Glu Leu Lys Arg Leu Thr Glu Glu Asp Glu Arg Arg Glu Arg Arg
                130                 135                 140 aca gcg ggt cct tca gtc ggc ggt gtt aac cca tta gaa ggt ggt tca      483
Thr Ala Gly Pro Ser Val Gly Gly Val Asn Pro Leu Glu Gly Gly Ser
            145                 150                 155 aga ggg gga gca cct gga gga gga ttc gta cca aac atg ttg tcc gtt      531
Arg Gly Gly Ala Pro Gly Gly Gly Phe Val Pro Asn Met Leu Ser Val
        160                 165                 170 cca gaa agc cca ttt tcc aga acc ggg gaa ggg ctg gac gtt aga ggt      579
Pro Glu Ser Pro Phe Ser Arg Thr Gly Glu Gly Leu Asp Val Arg Gly
    175                 180                 185 aat caa gga ttt cca tgg gat ata ctt ttt cca gca gat cca cca ttt      627
Asn Gln Gly Phe Pro Trp Asp Ile Leu Phe Pro Ala Asp Pro Pro Phe
190                 195                 200                 205 tct cct caa tct tgt agg cca cag atg tct cag tca gaa tcc aga aaa      675
Ser Pro Gln Ser Cys Arg Pro Gln Met Ser Gln Ser Glu Ser Arg Lys
                210                 215                 220 agc aga aga ggc gga aga gag gat att ttg gaa aaa tgg gtg tct act      723
Ser Arg Arg Gly Gly Arg Glu Asp Ile Leu Glu Lys Trp Val Ser Thr
            225                 230                 235 aga aag aaa gct gag gaa tta gaa agg gat ctt aga aaa gcg aga aaa      771
Arg Lys Lys Ala Glu Glu Leu Glu Arg Asp Leu Arg Lys Ala Arg Lys
        240                 245                 250
```

```
acc att aaa aga ctg gaa gat gat aat cca tgg ttg ggc aac atc cta      819
Thr Ile Lys Arg Leu Glu Asp Asp Asn Pro Trp Leu Gly Asn Ile Leu
    255                 260                 265 ggt ata atc aga aaa gga aaa gat ggg aca gac caa atg gaa gta gat      867
Gly Ile Ile Arg Lys Gly Lys Asp Gly Thr Asp Gln Met Glu Val Asp
270                 275                 280                 285 tct gga cct agg aaa aag cct cat aag tca ggt ttc acg gat aag gaa      915
Ser Gly Pro Arg Lys Lys Pro His Lys Ser Gly Phe Thr Asp Lys Glu
                290                 295                 300 aga caa gac cac aga cgt aga aaa gct ttg caa aac aag aag aac caa      963
Arg Gln Asp His Arg Arg Arg Lys Ala Leu Gln Asn Lys Lys Asn Gln
            305                 310                 315 ctg tcc gca gga ggc aaa tct ctc tca aaa gag gaa gaa gaa gag ctg     1011
Leu Ser Ala Gly Gly Lys Ser Leu Ser Lys Glu Glu Glu Glu Glu Leu
        320                 325                 330 agg aga ctt act ata gaa gat gac gag aga caa aga cga gtt gcc ggt     1059
Arg Arg Leu Thr Ile Glu Asp Asp Glu Arg Gln Arg Arg Val Ala Gly
    335                 340                 345 cca aga gtt ggt gac gtc aat cca cct ggc ggt agt cct aga gga gcc     1107
Pro Arg Val Gly Asp Val Asn Pro Pro Gly Gly Ser Pro Arg Gly Ala
350                 355                 360                 365 cct gga ggg ggc ttt gta cca caa atg aca ggt gtc cct gaa tca cca     1155
Pro Gly Gly Gly Phe Val Pro Gln Met Thr Gly Val Pro Glu Ser Pro
                370                 375                 380 ttc tct aga act ggt gaa ggt ttg gat atc aga ggt gac aga ggt ttt     1203
Phe Ser Arg Thr Gly Glu Gly Leu Asp Ile Arg Gly Asp Arg Gly Phe
            385                 390                 395 cca tgg gtg aat cct gct cca cca ggt cag cga tta cca tta ttg gaa     1251
Pro Trp Val Asn Pro Ala Pro Pro Gly Gln Arg Leu Pro Leu Leu Glu
        400                 405                 410 tgc aca cct caa cat cac cat cac cac cat tag gcggccgc                1292
Cys Thr Pro Gln His His His His His His
    415                 420

<210> SEQ ID NO 36
<211> LENGTH: 423
<212> TYPE: PRT
<213> ORGANISM: Artificial
<220> FEATURE:
<223> OTHER INFORMATION: Synthetic Construct

<400> SEQUENCE: 36

Met Ala Asp Glu Ala Pro Thr Ser Met Ser Arg Ser Glu Ser Lys Arg
1               5                   10                  15

Asn Arg Asp Gly Arg Glu Gly Ile Leu Glu Gln Trp Val Asn Gly Arg
                20                  25                  30

Lys Lys Leu Glu Asp Leu Glu Arg Asp Leu Arg Lys Ile Lys Lys Lys
            35                  40                  45

Ile Lys Lys Leu Glu Asp Glu Asn Pro Trp Leu Gly Asn Ile Lys Gly
        50                  55                  60

Ile Leu Gly Lys Lys Asp Lys Asp Gly Thr Asp Gln Met Glu Ile Asp
65                  70                  75                  80

Ser Gly Pro Gly Lys Arg Pro Leu Arg Gly Gly Phe Ser Asp Lys Glu
                85                  90                  95

Arg Gln Asp His Arg Arg Arg Lys Ala Leu Glu Asn Lys Arg Lys Gln
            100                 105                 110

Leu Ala Ala Gly Gly Lys His Leu Ser Lys Glu Glu Glu Glu Glu Leu
        115                 120                 125
```

```
                        -continued

Lys Arg Leu Thr Glu Glu Asp Glu Arg Arg Glu Arg Arg Thr Ala Gly
    130                 135                 140
Pro Ser Val Gly Gly Val Asn Pro Leu Glu Gly Gly Ser Arg Gly Gly
145                 150                 155                 160
Ala Pro Gly Gly Gly Phe Val Pro Asn Met Leu Ser Val Pro Glu Ser
                165                 170                 175
Pro Phe Ser Arg Thr Gly Glu Gly Leu Asp Val Arg Gly Asn Gln Gly
            180                 185                 190
Phe Pro Trp Asp Ile Leu Phe Pro Ala Asp Pro Pro Phe Ser Pro Gln
        195                 200                 205
Ser Cys Arg Pro Gln Met Ser Gln Ser Glu Ser Arg Lys Ser Arg Arg
    210                 215                 220
Gly Gly Arg Glu Asp Ile Leu Glu Lys Trp Val Ser Thr Arg Lys Lys
225                 230                 235                 240
Ala Glu Glu Leu Glu Arg Asp Leu Arg Lys Ala Arg Lys Thr Ile Lys
                245                 250                 255
Arg Leu Glu Asp Asp Asn Pro Trp Leu Gly Asn Ile Leu Gly Ile Ile
            260                 265                 270
Arg Lys Gly Lys Asp Gly Thr Asp Gln Met Glu Val Asp Ser Gly Pro
        275                 280                 285
Arg Lys Lys Pro His Lys Ser Gly Phe Thr Asp Lys Glu Arg Gln Asp
    290                 295                 300
His Arg Arg Arg Lys Ala Leu Gln Asn Lys Lys Asn Gln Leu Ser Ala
305                 310                 315                 320
Gly Gly Lys Ser Leu Ser Lys Glu Glu Glu Glu Leu Arg Arg Leu
                325                 330                 335
Thr Ile Glu Asp Asp Glu Arg Gln Arg Arg Val Ala Gly Pro Arg Val
            340                 345                 350
Gly Asp Val Asn Pro Pro Gly Gly Ser Pro Arg Gly Ala Pro Gly Gly
        355                 360                 365
Gly Phe Val Pro Gln Met Thr Gly Val Pro Glu Ser Pro Phe Ser Arg
    370                 375                 380
Thr Gly Glu Gly Leu Asp Ile Arg Gly Asp Arg Gly Phe Pro Trp Val
385                 390                 395                 400
Asn Pro Ala Pro Pro Gly Gln Arg Leu Pro Leu Leu Glu Cys Thr Pro
                405                 410                 415
Gln His His His His His
            420
```

YEAST-BASED COMPOSITIONS AND METHODS FOR THE TREATMENT OR PREVENTION OF HEPATITIS DELTA VIRUS INFECTION

CROSS-REFERENCE TO RELATED APPLICATIONS

This application is a divisional application of U.S. application Ser. No. 14/125,779, filed Feb. 13, 2014, which is a national stage application under 35 U.S.C. 371 of PCT Application No. PCT/US2012/042426 having an international filing date of 14 Jun. 2012, which designated the United States, which claims the benefit of priority under 35 U.S.C. § 119(e) from U.S. Provisional Patent Application No. 61/497,039, filed Jun. 14, 2011. The entire disclosure of each is incorporated herein by reference.

REFERENCE TO A SEQUENCE LISTING

This application contains a Sequence Listing submitted electronically as a text file by EFS-Web. The text file, named "3923-39-PCT_ST25", has a size in bytes of 66 KB, and was recorded on 12 Jun. 2012. The information contained in the text file is incorporated herein by reference in its entirety pursuant to 37 CFR § 1.52(e)(5).

FIELD OF THE INVENTION

The present invention generally relates to immunotherapeutic compositions and methods for preventing and/or treating hepatitis delta virus (HDV) infection.

BACKGROUND OF THE INVENTION

Hepatitis D is a disease caused by infection with a small, circular enveloped RNA virus known as hepatitis delta virus (HDV). HDV was first discovered in 1977 (Rizzetto et al., Gut 1977; 18: 997-1003) and was later shown to be the infectious agent of a new form of hepatitis (Rizzetto et al., J Infect Dis 1980; 141: 590-602; Rizzetto et al., Proc Natl Acad Sci USA 1980; 77: 6124-8; Wang et al., Nature 1986; 323: 508-14; Mason et al., In: Fauquet C M, Mayo M A, Maniloff J, Desselberger U, Ball L A, eds. Eight Report of the International Committee on Taxonomy of Viruses. London: Elsevier/Academic Press, 2005; 735-8). It has been recently estimated that 15-20 million people are infected with HDV, which requires concurrent infection with hepatitis B virus (HBV) for its life cycle, although this number may be underrepresented due in part to the lack of systematic screening for HDV infection in HBV-infected individuals (Pascarella and Negro, Liver International 2011, 31: 7-21).

Hepatitis D viruses are spherical particles that contain a core structure formed from an HDV genomic RNA that is complexed with about 70 molecules of HDAg (in both small and large forms) (Ryu et al., J Virol 1993; 67:3281-7). HDV is believed to enter the cell using the same receptor as HBV, utilizing the HBV envelope proteins as its outer coat. The envelope is comprised of approximately 100 copies of HBV surface antigen proteins (small, middle and large HBsAg). The large HDAg and HBsAg are sufficient to form virus particles, which are not infectious unless HDV RNA is also included, and small HDAg increases the packaging efficiency of the virus (Chen et al., J Virol 1992; 66: 2853-9; Wang et al., J Virol 1994; 68: 6363-71).

Once inside the cell, HDV uses host cellular RNA polymerases. Three RNAs accumulate during virus replication processes. The HDV genome is a circular negative single-stranded RNA of about 1672-1697 nucleotides (Radjef et al., J Virol 2004; 78:2537-44) and contains a ribozyme domain, spanning nucleotides 680-780, and a putative promoter site for HDAg RNA (Beard et al., J Virol 1996; 70: 4986-95). The antigenome, which contains the open reading frame coding for HDAg and a ribozyme domain (Sharmeen et al., J Virol 1988; 62: 2674-9; Ferre-D'amare et al., Nature 1998; 395:567-74) is the perfect complement of the genome and its replication occurs through RNA-directed RNA synthesis without any DNA intermediates (Chen et al., Proc Natl Acad Sci USA 1986; 83: 8774-8). The mRNA directs the synthesis of HDAg.

There is only one known protein encoded by the HDV genome, and it consists of two forms, a 27 kDa large (L) HDAg (HDAg-L or L-HDAg) (214 amino acids) and a 24 kDa small (S) HDAg (HDAg-S or S-HDAg) (195 amino acids). The proteins differ by about 19 amino acids at the C-terminus of the large HDAg. The N-terminus of the HDV antigen is responsible for nuclear localization signaling, the middle domain of HDV antigen is responsible for RNA binding, and the C-terminus is involved in virion assembly and inhibition of RNA assembly. HDAg-S is produced in early stages of the viral infection and supports viral replication. HDAg-L is produced later in viral infection, inhibits viral infection, and is required for assembly of viral particles.

HDV infection occurs only in individuals who are co-infected with a different virus, hepatitis B virus (HBV), and more specifically, only in HBV surface antigen (HBsAg)-positive individuals. As discussed above, HDV requires the HBV HBsAg for particle formation and transmission, and so HBV is essential for HDV virion assembly and release. There are two primary known ways in which HDV infects an individual. In the first, called co-infection, HDV and HBV can simultaneously co-infect an individual as an acute infection, and this type of infection results in about 95% recovery of most persons, similar to recovery rates for acute HBV infection alone. The second type of HDV infection, which is more common, is "superinfection", where HDV acutely infects an individual who already has chronic HBV infection. In this case, the HDV infection progresses to chronic HDV infection in about 80-90% of individuals, and it is this chronic HDV infection that is the more severe form of the disease. Therefore, superinfection can be classified as the earlier acute HDV superinfection of a chronic HBV carrier or the later HDV chronic infection. A third, but controversial, form of potential HDV infection, called helper-independent latent infection, was initially reported in 1991, and was described as occurring during liver transplantation (Ottobrelli et al., Gastroenterology 1991; 101: 1649-55). In this form of infection, a patient's hepatocytes might be infected with HDV alone (e.g., during liver transplantation when HBV transmission is prevented by administration of hepatitis B immunoglobulins), but if residual HBV escapes neutralization, or the patient is otherwise exposed to HBV subsequently, the HDV infected cells may be "rescued". This form has been demonstrated in animal models, but such infection of human hepatocytes remains controversial.

Chronic hepatitis D is now considered to be the most severe form of viral hepatitis in humans (for a detailed review of the disease and associated HDV, see Grabowski and Wedemeyer, 2010, Dig. Disease 28:133-138; or Pascarella and Negro, Liver International 2011, 31: 7-21).

Individuals chronically infected with HDV have an accelerated progression to fibrosis, increased risk of hepatocellular carcinoma, and early decompensation in the setting of cirrhosis. The disease may be asymptomatic or present with non-specific symptoms, and the diagnosis may only occur once complications appear at the cirrhosis stage of the disease. Alanine aminotransferase (ALT) and aspartate aminotransferase (AST) levels are persistently elevated in most patients and can be used to monitor the disease. Within 5-10 years, as many as 70-80% of chronic hepatitis D patients may develop cirrhosis (Rizzetto et al., Ann Intern Med 1983; 98: 437-41; Govindarajan et al., Hepatology 1986; 6: 640-4) and 15% within 1-2 years (Saracco et al., *J Hepatol* 1987; 5: 274-81). HDV infection may also accelerate the development of hepatocellular carcinoma (HCC).

HDV infection is most prevalent in the Mediterranean basin, the Middle East, Central and Northern Asia, West and Central Africa, the Amazonian basin, Venezuela, Colombia and certain islands of the Pacific, although the virus is present and/or emerging worldwide (e.g., Russia, Northern India, Southern Albania, mainland China, and some Pacific Islands). HDV infection is parenterally transmitted, most typically through drug use or exposure to blood or blood products. Sexual transmission of HDV is less common, and perinatal transmission of the virus is rare.

Regardless of the mode of HDV infection, there is currently no good option for the treatment or prevention of HDV infection. The anti-viral drugs used to treat other viruses that infect hepatocytes (e.g., antiviral drugs for HBV or HCV), are not effective against HDV. Immunomodulatory drugs such as corticosteroids or lemivasole have not been effective (Rizzetto et al., Ann Intern Med 1983; 98: 437-41; Arrigoni et al., Ann Intern Med 1983; 98:1024), nor have thymus-derived peptides (Rosina et al., Dig Liver Dis 2002; 34: 285-9; Zavaglia et al., J Clin Gastroenterol 1996; 23: 162-3). This leaves interferon treatment (e.g., pegylated interferon-α; pegIFN-α) as the only presently approved treatment for HDV infection. However, it is known that HDV can interfere with IFN-α signaling in vitro and indeed, treatment of HDV with pegIFN-α suffers from treatment failures and low response rates. In one prospective trial, only 21% of the patients achieved HDV RNA negativity and only 26% had a biochemical response (Niro et al., *Hepatology* 2006; 44:713-20), and similar results have been obtained in other trials, where sustained response to therapy (cure) remains very low. Therefore, there is a need in the art for new prophylactic and therapeutic approaches for HDV infection.

SUMMARY OF THE INVENTION

One embodiment of the invention relates to an immunotherapeutic composition comprising: (a) a yeast vehicle; and (b) a fusion protein comprising HDV antigens. The composition elicits an HDV-specific immune response when administered to a subject.

In one aspect of this embodiment of the invention, the HDV antigens consist of at least one immunogenic domain of an HDV large antigen (HDAg-L) or an HDV small antigen (HDAg-S), wherein the nuclear localization sequence (NLS) has been inactivated by substitution or deletion of one or more amino acids of the NLS. For example, an NLS can be inactivated by the deletion of the entire NLS, although the invention is not limited to this example.

In one aspect of this embodiment of the invention, the HDV antigen consists of at least one full-length HDAg-L or HDAg-S, except that the nuclear localization sequence (NLS) of the HDAg-L or HDAg-S has been inactivated by substitution or deletion of one or more amino acids of the NLS.

In another aspect of this embodiment of the invention, the HDV antigen consists of a fusion of two or more full-length HDAg-L or HDAg-S, except that the nuclear localization sequence (NLS) of each of the HDAg-L or HDAg-S has been inactivated by substitution or deletion of one or more amino acids of the NLS. For example, in one aspect, the NLS is deleted. In one aspect of this embodiment, each of the HDAg-L or HDAg-S is from a different HDV genotype.

In yet another aspect of this embodiment of the invention, the HDV antigen consists of a fusion of three full-length HDAg-L or HDAg-S, except that the nuclear localization sequence (NLS) of each of the HDAg-L or HDAg-S has been inactivated by substitution or deletion of one or more amino acids of the NLS. In one aspect of this embodiment, each of the HDAg-L or HDAg-S is from a different HDV genotype. In one example of such an HDV antigen, a full-length genotype 1 HDAg-L sequence represented by SEQ ID NO:2 (or a corresponding sequence from another HDV strain) with a deletion of positions 66-75 (the NLS) is linked to a full-length genotype 2 HDAg-L sequence represented by SEQ ID NO:5 (or a corresponding sequence from another HDV strain) with a deletion of positions 66-75 (the NLS) which is linked to a full-length genotype 3 HDAg-L sequence represented by SEQ ID NO:8 (or a corresponding sequence from another HDV strain) with a deletion of positions 66-75 (the NLS). The arrangement of these three HDAg's in the fusion protein can be modified to any order besides the one above. In one aspect, the three HDAg's are from different genotypes or subgenotypes of HDV than listed above.

In one aspect of this embodiment of the invention, the HDV antigen comprises an amino acid sequence that is at least 95% identical to an amino acid sequence selected from SEQ ID NO:34, SEQ ID NO:28, or a corresponding amino acid sequence from another HDV strain. In one aspect, the HDV antigen comprises an amino acid sequence that is at least 96% identical, at least 97% identical, at least 98% identical, or at least 99% identical, to an amino acid sequence selected from SEQ ID NO:34, SEQ ID NO:28, or a corresponding amino acid sequence from another HDV strain. In one aspect, the HDV antigen is selected from SEQ ID NO:34, SEQ ID NO:28, or a corresponding sequence from another HDV strain.

In one aspect of this embodiment of the invention, the fusion protein has an amino acid sequence selected from SEQ ID NO:36 or SEQ ID NO:30 or an amino acid sequence that is at least 95% identical to SEQ ID NO:36 or SEQ ID NO:30, respectively.

In yet another embodiment related to the immunotherapeutic composition of the invention, the HDV antigens consist of at least one immunogenic domain of an HDV large antigen (HDAg-L) or HDV small antigen (HDAg-S), wherein the HDV antigen is less than a full-length HDAg-L or HDAg-S protein. In one aspect, the HDV antigen consists of a fusion of at least two or more HDAg-L or HDAg-S proteins, wherein at least one of the HDAg-L or HDAg-S proteins is less than a full-length HDAg-L or HDAg-S protein. In one aspect, each of the HDAg-L or HDAg-S proteins is from a different HDV genotype. In one aspect, the HDV antigen comprises an amino acid sequence that is at least 95% identical to an amino acid sequence selected from SEQ ID NO:10, SEQ ID NO:16, or a corresponding amino acid sequence from another HDV strain. In one aspect, the HDV antigen comprises an amino acid sequence that is at least 96% identical, at least 97% identical, at least 98% identical, or at least 99% identical, to an amino acid sequence selected from SEQ ID NO:10, SEQ ID NO:16, or a corresponding amino acid sequence from another HDV strain. In one aspect, the HDV antigen is selected from SEQ ID NO:10, SEQ ID NO:16, or a corresponding sequence from another HDV strain.

In one aspect of this embodiment of the invention, the fusion protein is selected from SEQ ID NO:12, SEQ ID NO:15, SEQ ID NO:17, or SEQ ID NO:18.

In any of the above-described embodiments of the invention, in one aspect the HDAg-L has an amino acid sequence selected from SEQ ID NO:2, SEQ ID NO:5, SEQ ID NO:8, or a corresponding amino acid sequence from another HDV strain. In one aspect, the HDAg-S has an amino acid sequence selected from SEQ ID NO:3, SEQ ID NO:6, SEQ ID NO:9, or a corresponding sequence from another HDV strain. In one aspect, the HDV antigen comprises an amino acid sequence that is at least 95% identical to an amino acid sequence selected from SEQ ID NO:2, SEQ ID NO:5, SEQ ID NO:8, or a corresponding amino acid sequence from another HDV strain.

In any of the above-described embodiments related to an immunotherapeutic composition of the invention, in one aspect, the HDV antigen is expressed by the yeast vehicle. In one aspect, the yeast vehicle is a whole yeast. In one aspect, the whole yeast is killed. In one aspect, the whole yeast is heat-inactivated. In one aspect, the yeast vehicle is from a yeast genus selected from the group consisting of: *Saccharomyces, Candida, Cryptococcus, Hansenula, Kluyveromyces, Pichia, Rhodotorula, Schizosaccharomyces* and *Yarrowia*. In one aspect, the yeast vehicle is from *Saccharomyces*. In one aspect, the yeast vehicle is from *Saccharomyces cerevisiae*.

In any of the above-described embodiments related to an immunotherapeutic composition of the invention, in one aspect, the composition is formulated in a pharmaceutically acceptable excipient suitable for administration to a subject.

In any of the above-described embodiments related to an immunotherapeutic composition of the invention, in one aspect, the composition contains greater than 90% yeast protein.

Another embodiment of the invention relates to a method to treat hepatitis D virus (HDV) infection or at least one symptom resulting from HDV infection in a subject or improve survival of a subject who is infected with HDV. The method includes a step of administering to a subject that has been infected with HDV at least one immunotherapeutic composition as described above or elsewhere herein, wherein administration of the composition to the subject reduces HDV infection or at least one symptom resulting from HDV infection in a subject. In one aspect, the method additionally includes administering to the subject one or more additional agents useful for treating or ameliorating a symptom of HDV infection. For example, such an agent can include, but is not limited to, an interferon. Interferons include, but are not limited to, interferon-α, including, but not limited to, pegylated interferon-α2a. In one aspect, the interferon is interferon-λ.

In one aspect of this embodiment of the invention, the subject is chronically infected with hepatitis B virus (HBV). In one aspect, the method further includes a step of administering to the subject an anti-viral compound to treat the HBV infection. Such an anti-viral compound can include, but is not limited to: tenofovir, lamivudine, adefovir, telbivudine, entecavir, and combinations thereof.

Yet another embodiment of the invention relates to a method to elicit an antigen-specific, cell-mediated immune response against an HDV antigen, comprising administering to a subject at least one immunotherapeutic composition as described above or elsewhere herein.

Another embodiment of the invention relates to a method to prevent HDV infection in a subject, comprising administering to a subject that has not been infected with HDV, at least one immunotherapeutic composition as described above or elsewhere herein. In one aspect of this embodiment, the subject is chronically infected with hepatitis B virus (HBV). In one aspect, the method additionally includes administering to the subject an anti-viral compound to treat the HBV infection.

Yet another embodiment of the invention relates to a method to immunize a population of individuals against HDV, comprising administering to the population of individuals at least one immunotherapeutic composition as described above or elsewhere herein. In one aspect of this embodiment of the invention, the population of individuals is chronically infected with HBV.

Another embodiment of the invention relates to an immunotherapeutic composition as described above or elsewhere herein, for use to treat HDV infection.

Yet another embodiment of the invention relates to an immunotherapeutic composition as described above or elsewhere herein, for use to prevent HDV infection in a subject. In one aspect, the subject is chronically infected with HBV.

Another embodiment of the invention relates to the use of at least one immunotherapeutic composition as described above or elsewhere herein in the preparation of a medicament to treat HDV infection.

Yet another embodiment of the invention relates to the use of at least one immunotherapeutic composition as described above or elsewhere herein in the preparation of a medicament to prevent HDV infection.

BRIEF DESCRIPTION OF THE DRAWINGS OF THE INVENTION

FIG. 1 is a sequence alignment showing shows the portions of the HDAg used in the construct represented by SEQ ID NO:16 aligned, to illustrate the homology among genotypes used in this fusion protein ("genotype1" sequence on line 1 is positions 1-140 of SEQ ID NO:16; "genotype2" sequence on line 2 is positions 141-280 of SEQ ID NO:16; "genotype3" sequence on line 3 is positions 281-420 of SEQ ID NO:16).

FIG. 6A is a graph showing an interleukin-2 (IL-2) ELISpot of yeast-based HDV immunotherapeutic composition HDV-1-vaccinated C57BL/6 mice using HDV-P1 peptide (OVAX=control yeast expressing irrelevant antigen).

FIG. 6B is a graph showing the same ELISpot results as in FIG. 6A, with the medium background subtracted.

DETAILED DESCRIPTION OF THE INVENTION

Figure 2:
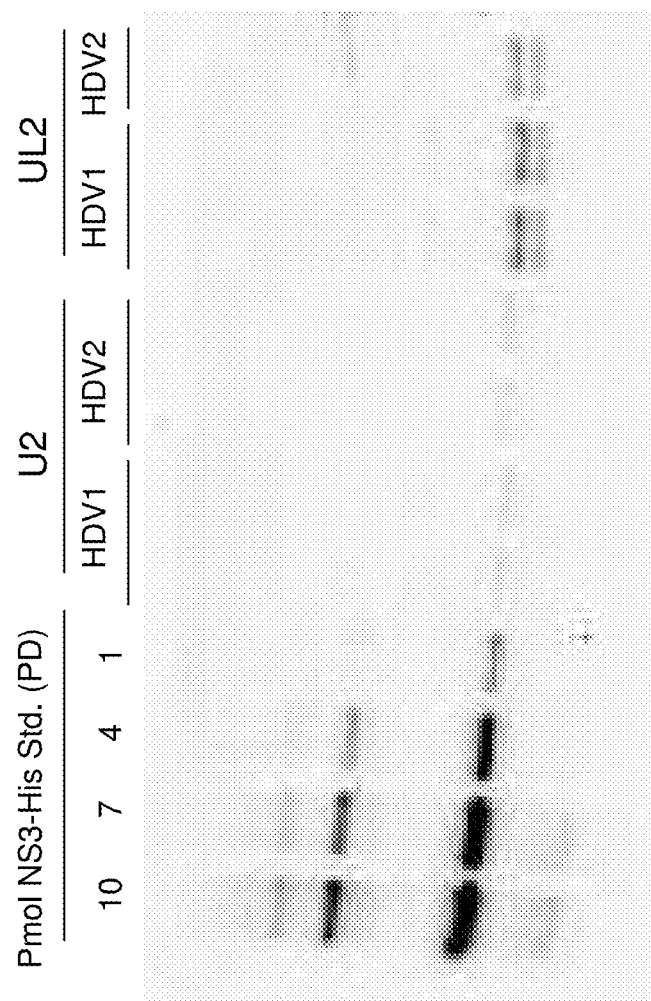
FIG. 2 is a digitized image showing expression of the yeast-based immunotherapeutics known as HDV1 (expressing SEQ ID NO:30) and HDV2 (expressing SEQ ID NO:33), grown in U2 and UL2 medium, and compared to one set of NS3-His standards.
Figure 3:
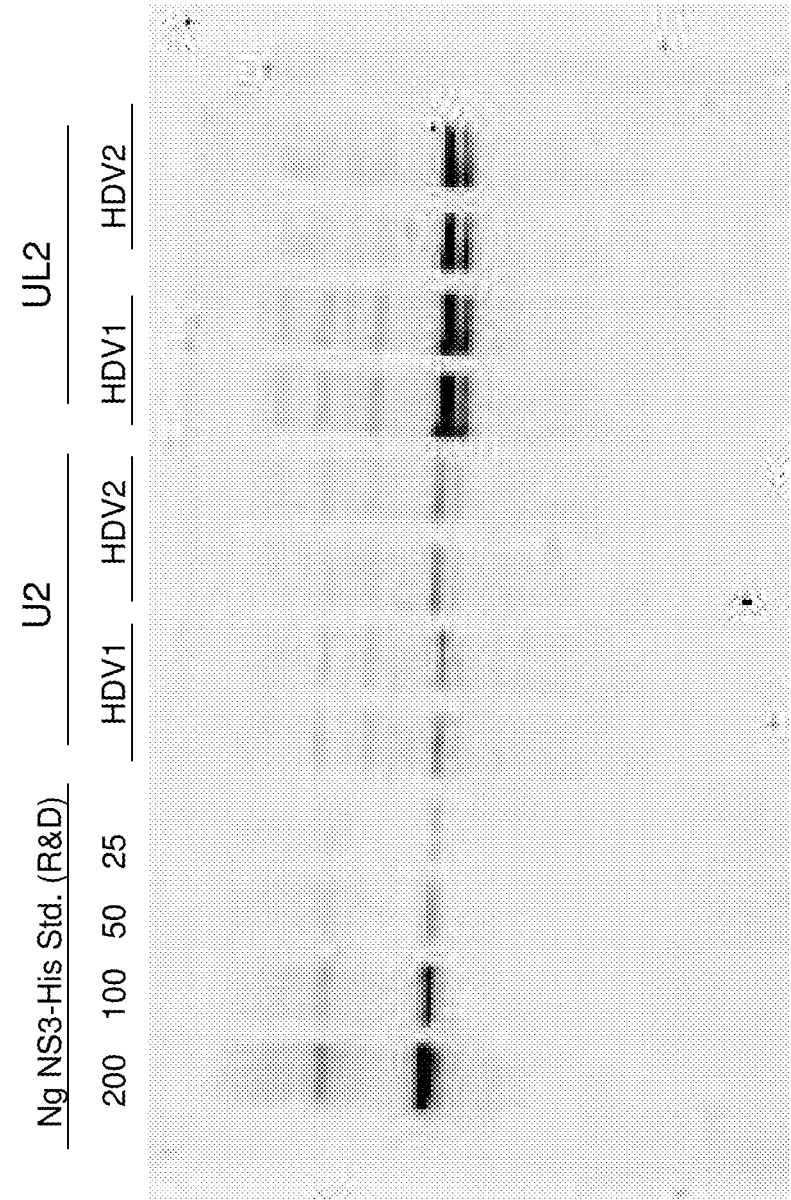
FIG. 3 is a digitized image showing expression of the yeast-based immunotherapeutics known as HDV1 (expressing SEQ ID NO:30) and HDV2 (expressing SEQ ID NO:33), grown in U2 and UL2 medium, and compared to a second set of NS3-His standards.

This invention generally relates to compositions and methods for preventing and/or treating hepatitis delta virus (HDV) infection. The invention includes a yeast-based immunotherapeutic composition (also referred to as yeast-based HDV immunotherapy) comprising a yeast vehicle and HDV antigen(s) that have been designed to elicit a prophylactic and/or therapeutic immune response against HDV infection in a subject, and the use of such compositions to prevent and/or treat HDV infection. The invention also includes the recombinant nucleic acid molecules used in the yeast-based compositions of the invention, as well as the proteins encoded thereby, for use in any immunotherapeutic composition and/or any therapeutic or prophylactic protocol for HDV, including any therapeutic or prophylactic protocol that combines the HDV-specific yeast-based compositions of the invention with any one or more other therapeutic or prophylactic compositions, agents, drugs, compounds, and/or protocols for HDV infection and/or related co-infections.

Yeast-based immunotherapeutic compositions are administered as biologics or pharmaceutically acceptable compositions. Accordingly, rather than using yeast as an antigen production system followed by purification of the antigen from the yeast, the entire yeast vehicle as described herein must be suitable for, and formulated for, administration to a patient. This is in contrast to the use of yeast to produce recombinant proteins for subunit vaccines, where the proteins, once expressed, are subsequently released from the yeast by disruption and purified from the yeast so that the final vaccine combined with an adjuvant contains no detectable yeast DNA and contains no more than 1-5% yeast protein. The HDV yeast-based immunotherapeutic compositions of the invention, on the other hand, contain readily detectable yeast DNA and contain substantially more than 5% yeast protein (i.e., more than 5% of the total protein in the vaccine is that belonging to or contributed by the yeast); generally, yeast-based immunotherapeutics of the invention contain more than 70%, more than 80%, or generally more than 90% yeast protein.

Yeast-based immunotherapeutic compositions are administered to a patient in order to immunize the patient for therapeutic and/or prophylactic purposes. In one embodiment of the invention, the yeast-based compositions are formulated for administration in a pharmaceutically acceptable excipient or formulation. The composition should be formulated, in one aspect, to be suitable for administration to a human subject (e.g., the manufacturing conditions should be suitable for use in humans, and any excipients or formulations used to finish the composition and/or prepare the dose of the immunotherapeutic for administration should be suitable for use in humans). In one aspect of the invention, yeast-based immunotherapeutic compositions are formulated for administration by injection of the patient or subject, such as by a parenteral route (e.g., by subcutaneous, intraperitoneal, intramuscular or intradermal injection, or another suitable parenteral route).

In one embodiment, the yeast express the antigen (e.g., detectable by a Western blot), and the antigen is not aggregated in the yeast, the antigen does not form inclusion bodies in the yeast, and/or does not form virus-like particles (VLPs) or other large antigen particles in the yeast. In one embodiment, the antigen is produced as a soluble protein in the yeast, and/or is not secreted from the yeast or is not substantially or primarily secreted from the yeast. The yeast-based immunotherapeutics should be readily phagocytosed by dendritic cells of the immune system, and the yeast and antigens readily processed by such dendritic cells, in order to elicit an effective immune response against HDV.

Hepatitis D Virus Antigens, Constructs, and Compositions of the Invention

One embodiment of the present invention relates to a yeast-based immunotherapy composition which can be used to prevent and/or treat HDV infection and/or to alleviate at least one symptom resulting from the HDV infection. The composition comprises: (a) a yeast vehicle; and (b) one or more HDV antigens comprising HDV protein(s) and/or immunogenic domain(s) thereof, as described in detail herein. In conjunction with the yeast vehicle, the HDV antigens are most typically expressed as recombinant proteins by the yeast vehicle (e.g., by an intact yeast or yeast spheroplast, which can optionally be further processed to a yeast cytoplast, yeast ghost, or yeast membrane extract or fraction thereof), although it is an embodiment of the invention that one or more such HDV antigens are loaded into a yeast vehicle or otherwise complexed with, attached to, mixed with or administered with a yeast vehicle as described herein to form a composition of the present invention. According to the present invention, reference to a "heterologous" protein or "heterologous" antigen, including a heterologous fusion protein, in connection with a yeast vehicle of the invention, means that the protein or antigen is not a protein or antigen that is naturally expressed by the yeast, although a fusion protein that includes heterologous antigen or heterologous protein may also include yeast sequences or proteins or portions thereof that are also naturally expressed by yeast (e.g., an alpha factor prepro sequence as described herein).

One embodiment of the invention relates to HDV antigens useful in an immunotherapeutic composition of the invention and in one aspect, in a yeast-based immunotherapy composition of the invention. As discussed above, there is only one known protein encoded by the HDV genome, and it consists of two forms, a 27 kDa large (L) HDAg (HDAg-L or L-HDAg) (214 amino acids) and a 24 kDa small (S) HDAg (HDAg-S or S-HDAg) (195 amino acids). The proteins differ by about 19 amino acids at the C-terminus of the large HDAg.

Although there are presently known to be at least eight distinct genotypes of HDV (Le Gal et al., *Emerg Infect Dis* 2006; 12:1447-50), three genotypes are most prevalent, known as 1 (or I), 2 (or II), and 3 (or III). The genotype(s) can be determined in an individual by routine methods (e.g., restriction fragment length polymorphism (RFLP) analysis of polymerase chain reaction (PCR) products, sequencing, and/or immunohistochemical staining). Highly conserved domains among HDV genotypes are located around the genomic and antigenomic RNA autocatalytic cleavage sites and the RNA-binding domain of HDAg (Chao et al., *Virology* 1990; 178: 384-92; Wu et al., *Hepatology* 1995; 22: 1656-60).

Genotype 1 is presently the most dominant HDV genotype and is found worldwide, but particularly in Europe, North America, Africa and some Asian regions. An example of a genotype 1 HDV genome is represented by Database Accession No. AF104263 or GI:11022740, also represented herein by SEQ ID NO:1. SEQ ID NO:1 encodes an HDAg-L represented by SEQ ID NO:2 (also under Accession No. AAG26087.1 or GI:11022742) and an HDAg-S represented by SEQ ID NO:3. Genotype 2 is found in Japan, Taiwan and Russia. An example of a genotype 2 HDV partial genome is represented by Database Accession No. AJ309880 or GI:15212076, also represented herein by SEQ ID NO:4. SEQ ID NO:4 encodes an HDAg-L represented by SEQ ID NO:5 (also under Accession No. CAC51366.1 or GI:15212077) and an HDAg-S represented by SEQ ID NO:6. Genotype 3 is found in South America (e.g., Peru, Colombia, Venezuela). An example of a genotype 3 HDV genome is represented by Database Accession No. L22063.1 or GI:410182, also represented herein by SEQ ID NO:7. SEQ ID NO:7 encodes an HDAg-L represented by SEQ ID NO:8 (also under Accession No. POC6M3.1 or GI:226737601) and an HDAg-S represented by SEQ ID NO:9. Genotype 4 is found in Japan and Taiwan, and genotypes 5-8 are found in Africa. Various sequences of HDAg have been described for these genotypes and can be found in public databases. Multiple genotypes can infect a single patient, although one genotype typically dominates.

The nucleic acid and amino acid sequence for many HDV genomes and the HDAg proteins (large and small) encoded thereby are known in the art for each of the known genotypes. The above-described sequences are exemplary (representative). It is noted that small variations may occur in the amino acid sequence between different viral isolates of the same protein or domain from the same HDV genotype. However, the HDAg antigen has essentially the same overall structure among different strains and genotypes, such that one skilled in the art can readily determine from one given sequence of an HDAg the corresponding sequence of the HDAg from a different HDV strain/isolate or genotype. Therefore, using the guidance provided herein and the reference to the exemplary HDV sequences, one of skill in the art will readily be able to produce a variety of HDV-based proteins, including fusion proteins, from any HDV strain (isolate) or genotype, for use in the compositions and methods of the present invention, and as such, the invention is not limited to the specific sequences disclosed herein. Reference to an HDV protein or HDV antigen anywhere in this disclosure, or to any functional, structural, or immunogenic domain thereof, can accordingly be made by reference to a particular sequence from one or more of the sequences presented in this disclosure, or by reference to the same, similar or corresponding sequence from a different HDV isolate (strain), including from a different genotype or sub-genotype than the reference isolate/strain.

While utilization of any of the full-length or near full-length HDV antigens (HDAg-L or HDAg-S) described herein is within the scope of the invention, additional HDV antigens are contemplated, particularly in order to optimize or enhance the usefulness of the HDV antigens as clinical products, including in the context of a yeast-based immunotherapeutic composition. HDV antigens that are useful in the present invention have been designed to produce an HDV yeast-based immunotherapeutic product that achieves one or more of the following goals: (1) inclusion of a maximized number of known T cell epitopes (MHC Class I and MHC Class II); (2) maximizing or prioritizing the inclusion of immunogenic domains, and more particularly T cell epitopes (CD4$^+$ and/or CD8$^+$ epitopes, and dominant and/or subdominant epitopes), that are the most conserved among HDV genotypes and/or sub-genotypes, or that can be readily modified to a consensus sequence or included in two or more forms to cover the most important sequence differences among target genotypes; (3) minimizing the number of non-natural junctions within the sequence of the HDV antigen in the product; (4) minimizing or eliminating sequences that may interfere with the expression of the protein by yeast (e.g., hydrophobic domains); and/or (5) minimizing or eliminating sequences that may be essential for viral function (the nuclear localization sequence), e.g., modifications to deactivate the virus. In one embodiment, HDV antigens may be designed to comply with the guidelines of the Recombinant DNA Advisory Committee (RAC) of the National Institutes of Health (NIH).

In one embodiment of the invention, an HDV antigen useful in the invention consists of HDAg that are encoded by less than about: 99%, 98%, 97%, 96%, 95%, 94%, 93%, 92%, 91%, 90%, 85%, 80%, 75%, 70%, or 66.67% of an HDV genome, although several copies of the same HDAg meeting this parameter, or two or more different HDAg meeting the parameter but each coming from a different genotype, sub-genotype, or HDV strain/isolate, can be provided in the form of a fusion protein in the present invention.

In one embodiment of the invention, an HDV antigen useful in the invention consists of HDAg containing a mutation sufficient to deactivate or remove the nuclear localization sequence (NLS; represented, for example, by the published sequence of AGAPPAKRAR (SEQ ID NO:27) or by EGAPPAKRAR which corresponds to positions 66-75 of SEQ ID NO:2, or the corresponding sequence from a different HDV genotype or strain/isolate of HDV). Such a mutation can consist of a deletion or substitution of one, two, three, four, five, six, seven, eight, nine, or all ten of the amino acid residues comprising the NLS. Additional amino acids flanking the NLS may also be deleted or substituted, although this is typically not required, and it is more preferable to retain amino acid residues from natural T cell epitopes in the HDV antigen. Removal of the NLS is useful for at least two reasons. First, concerns regarding the potential biological activity of the HDV antigen used in the invention are obviated (the virus is inactivated) and second, the inventors have discovered that deletion of this functional site improves expression of the resulting protein or fusion protein in yeast, while improving the growth rate and eliminating an abnormal clumping morphology the yeast acquired when expressing the HDV antigen containing the NLS sequence.

Table 1 shows several published T cell epitopes from HDV (positions given with respect to a HDAg-L protein), any one or more of which may be used in an HDV antigen according to the present invention. In one aspect of the invention, an HDV antigen includes at least one, two, three, four, five, or more of these epitopes or other T cell epitopes.

TABLE 1

| Epitope | Sequence Identifier | HDAg Position | HLA Preference |
|---|---|---|---|
| [1]KLEDENPWL | SEQ ID NO: 19 | 43-51 | Class I A2 |
| [1]KLEDLERDL | SEQ ID NO: 20 | 26-34 | Class I A2 |

TABLE 1-continued

| Epitope | Sequence Identifier | HDAg Position | HLA Preference |
|---|---|---|---|
| [2]KLEDLERDLRKIKKKI | SEQ ID NO: 21 | 26-41 | Class II |
| [2]WLGNIKGILGKKDKDG | SEQ ID NO: 22 | 50-65 | Class II |
| [2]AGAPPAKRARTDQMEI | SEQ ID NO: 23 | 66-81 | Class II |
| [2]ARTDQMEIDSGPGKRP | SEQ ID NO: 24 | 74-89 | Class II |
| [2]KALENKRKQLAAGGKH | SEQ ID NO: 25 | 106-121 | Class II |
| [2]LSKEEEEELKRLTEEDERRERRTAGPSVGGVN | SEQ ID NO: 26 | 122-153 (122-137, 130-145, & 138-153) | Class II (3 overlapping epitopes) |

[1]Huang et al., 2004, J Gen Virol 85:3089-3098
[2]Nisini et al., 1997, J. ViroL 71(3):2241-2251

HDV antigens and fusion proteins of the invention are useful in an immunotherapeutic composition of the invention, including a yeast-based immunotherapeutic composition of the invention. Such antigens, fusion proteins, and/or the recombinant nucleic acid molecules encoding such proteins, can also be used in, in combination with, or to produce, a non-yeast-based immunotherapeutic composition, which may include, without limitation, a DNA vaccine, a protein subunit vaccine, a recombinant viral-based immunotherapeutic composition, a killed or inactivated pathogen vaccine and/or a dendritic cell vaccine. In another embodiment, such fusion proteins can be used in a diagnostic assay for HDV and/or to generate antibodies against HDV.

One embodiment of the invention relates to novel HDV antigens and fusion proteins and recombinant nucleic acid molecules encoding these antigens and proteins. Described herein are several different novel HDV antigens for use in a yeast-based immunotherapeutic composition or other composition (e.g., other immunotherapeutic or diagnostic compositions).

According to the present invention, the general use herein of the term "antigen" refers: to any portion of a protein (peptide, partial protein, full-length protein), wherein the protein is naturally occurring or synthetically derived, to a cellular composition (whole cell, cell lysate or disrupted cells), to an organism (whole organism, lysate or disrupted cells) or to a carbohydrate, or other molecule, or a portion thereof. An antigen may elicit an antigen-specific immune response (e.g., a humoral and/or a cell-mediated immune response) against the same or similar antigens that are encountered by an element of the immune system (e.g., T cells, antibodies).

An antigen can be as small as a single epitope, a single immunogenic domain or larger, and can include multiple epitopes or immunogenic domains. As such, the size of an antigen can be as small as about 8-12 amino acids (i.e., a peptide) and as large as: a full length protein, a multimer, a fusion protein, a chimeric protein, a whole cell, a whole microorganism, or any portions thereof (e.g., lysates of whole cells or extracts of microorganisms). In addition, antigens can include carbohydrates, which can be loaded into a yeast vehicle or into a composition of the invention. It will be appreciated that in some embodiments (e.g., when the antigen is expressed by the yeast vehicle from a recombinant nucleic acid molecule), the antigen is a protein, fusion protein, chimeric protein, or fragment thereof, rather than an entire cell or microorganism.

When the antigen is to be expressed in yeast, an antigen is of a minimum size capable of being expressed recombinantly in yeast, and is typically at least or greater than 25 amino acids in length, or at least or greater than 26, at least or greater than 27, at least or greater than 28, at least or greater than 29, at least or greater than 30, at least or greater than 31, at least or greater than 32, at least or greater than 33, at least or greater than 34, at least or greater than 35, at least or greater than 36, at least or greater than 37, at least or greater than 38, at least or greater than 39, at least or greater than 40, at least or greater than 41, at least or greater than 42, at least or greater than 43, at least or greater than 44, at least or greater than 45, at least or greater than 46, at least or greater than 47, at least or greater than 48, at least or greater than 49, or at least or greater than 50 amino acids in length, or is at least 25-50 amino acids in length, at least 30-50 amino acids in length, or at least 35-50 amino acids in length, or at least 40-50 amino acids in length, or at least 45-50 amino acids in length. Smaller proteins may be expressed, and considerably larger proteins (e.g., hundreds of amino acids in length or even a few thousand amino acids in length) may be expressed. In one aspect, a full-length protein, or a structural or functional domain thereof, or an immunogenic domain thereof, that is lacking one or more amino acids from the N- and/or the C-terminus may be expressed (e.g., lacking between about 1 and about 20 amino acids from the N- and/or the C-terminus). Fusion proteins and chimeric proteins are also antigens that may be expressed in the invention. A "target antigen" is an antigen that is specifically targeted by an immunotherapeutic composition of the invention (i.e., an antigen against which elicitation of an immune response is desired). An "HDV antigen" is an antigen derived, designed, or produced from one or more HDV proteins such that targeting the antigen also targets the hepatitis D virus.

When referring to stimulation of an immune response, the term "immunogen" is a subset of the term "antigen", and therefore, in some instances, can be used interchangeably with the term "antigen". An immunogen, as used herein, describes an antigen which elicits a humoral and/or cell-mediated immune response (i.e., is immunogenic), such that administration of the immunogen to an individual mounts an antigen-specific immune response against the same or similar antigens that are encountered by the immune system of the individual. In one embodiment, an immunogen elicits a cell-mediated immune response, including a CD4$^+$ T cell response (e.g., TH1, TH2 and/or TH17) and/or a CD8$^+$ T cell response (e.g., a CTL response).

An "immunogenic domain" of a given antigen can be any portion, fragment or epitope of an antigen (e.g., a peptide fragment or subunit or an antibody epitope or other conformational epitope) that contains at least one epitope that acts as an immunogen when administered to an animal. Therefore, an immunogenic domain is larger than a single amino acid and is at least of a size sufficient to contain at least one epitope that can act as an immunogen. For example, a single protein can contain multiple different immunogenic domains. Immunogenic domains need not be linear sequences within a protein, such as in the case of a humoral immune response, where conformational domains are contemplated.

A "functional domain" of a given protein is a portion or functional unit of the protein that includes sequence or structure that is directly or indirectly responsible for at least one biological or chemical function associated with, ascribed to, or performed by the protein. For example, a functional domain can include an active site for enzymatic activity, a ligand binding site, a receptor binding site, a binding site for a molecule or moiety such as calcium, a phosphorylation site, or a transactivation domain. Examples of HDV functional domains include, but are not limited to, the nuclear localization sequence (NLS), RNA binding domain, and domains involved in virion assembly and inhibition of RNA assembly.

A "structural domain" of a given protein is a portion of the protein or an element in the protein's overall structure that has an identifiable structure (e.g., it may be a primary or tertiary structure belonging to and indicative of several proteins within a class or family of proteins), is self-stabilizing and/or may fold independently of the rest of the protein. A structural domain is frequently associated with or features prominently in the biological function of the protein to which it belongs.

An epitope is defined herein as a single immunogenic site within a given antigen that is sufficient to elicit an immune response when provided to the immune system in the context of appropriate costimulatory signals and/or activated cells of the immune system. In other words, an epitope is the part of an antigen that is actually recognized by components of the immune system, and may also be referred to as an antigenic determinant. Those of skill in the art will recognize that T cell epitopes are different in size and composition from B cell or antibody epitopes, and that epitopes presented through the Class I MHC pathway differ in size and structural attributes from epitopes presented through the Class II MHC pathway. For example, T cell epitopes presented by Class I MHC molecules are typically between 8 and 11 amino acids in length, whereas epitopes presented by Class II MHC molecules are less restricted in length and may be from 8 amino acids up to 25 amino acids or longer. In addition, T cell epitopes have predicted structural characteristics depending on the specific MHC molecules bound by the epitope. Some T cell epitopes have been identified in HDV strains and are identified in Table 1. Epitopes can be linear sequence epitopes or conformational epitopes (conserved binding regions). Most antibodies recognize conformational epitopes.

In any of the HDV antigens described herein, including any of the fusion proteins, the following additional embodiments can apply. First, the N-terminal expression sequence and the C-terminal tag included in some of the antigen constructs are optional, and if used, may be selected from several different sequences described elsewhere herein to impart resistance to proteasomal degradation and/or stabilize or improve expression, stability, and/or allow for identification and/or purification of the protein. Alternatively, one or both of the N- or C-terminal sequences are omitted altogether. In addition, many different promoters suitable for use in yeast are known in the art and are encompassed for use to express HDV antigens according to the present invention. Suitable promoters include, but are not limited to, CUP1 and TEF2. Furthermore, short intervening linker sequences (e.g., 1, 2, 3, 4, or 5, or larger, amino acid peptides) may be introduced between portions of the fusion protein for a variety of reasons, including the introduction of restriction enzyme sites to facilitate cloning and future manipulation of the constructs. Finally, as discussed in detail elsewhere herein, the sequences described herein are exemplary, and may be modified as described in detail elsewhere herein to substitute, add, or delete sequences in order to accommodate preferences for HDV genotype, HDV strain or isolate, or consensus sequences and inclusion of preferred T cell epitopes, including dominant and/or subdominant T cell epitopes. A description of several different exemplary HDV antigens useful in the invention is provided below.

In one embodiment of the invention, the HDV antigen(s) for use in a composition or method of the invention is a protein or fusion protein comprising HDV antigens, wherein the HDV antigens comprise or consist of all at least one HDAg-L or HDAg-S protein, and/or at least one immunogenic domain thereof. In one aspect, the HDAg-L or HDAg-S protein is full-length or near full-length. According to any embodiment of the present invention, reference to a "full-length" protein (or a full-length functional domain or full-length immunological domain) includes the full-length amino acid sequence of the protein or functional domain or immunological domain, as described herein or as otherwise known or described in a publicly available sequence. A protein or domain that is "near full-length", which is also a type of homologue of a protein, differs from a full-length protein or domain, by the addition or deletion or omission of 1, 2, 3, 4, 5, 6, 7, 8, 9, or 10 amino acids from the N- and/or C-terminus of such a full-length protein or full-length domain. General reference to a protein or domain can include both full-length and near full-length proteins, as well as other homologues thereof.

The HDV sequences used to design these constructs and the others described and/or exemplified herein are based on isolates or strains of a particular HDV genotype. However, it is an embodiment of the invention to add to or substitute into any portion of an HDV antigen described herein that is based on or derived from one particular genotype, sub-genotype, or strain/isolate, a corresponding sequence, or even a single or small amino acid substitution, insertion or deletion that occurs in a corresponding sequence, from any other HDV genotype(s), sub-genotype(s), or strain(s). In one embodiment, an HDV antigen can be produced by substituting an entire sequence(s) of an HDV antigen described herein with the corresponding sequence(s) from one or more different HDV genotypes, sub-genotypes or strain/isolates. Adding to or substituting a sequence from one HDV genotype or sub-genotype for another, for example, allows for the customization of the immunotherapeutic composition for a particular individual or population of individuals (e.g., a population of individuals within a given country or region of a country, in order to target the HDV genotype(s) that is most prevalent in that country or region of the country). Similarly, it is also an embodiment of the invention to use all or a portion of a consensus sequence derived from, determined from, or published for, a given HDV strain, genotype or subtype to make changes in the sequence of a given HDV antigen to more closely or exactly correspond to the consensus sequence. According to the present invention and as generally understood in the art, a "consensus sequence" is typically a sequence based on the most common nucleotide or amino acid at a particular position of a given sequence after multiple sequences are aligned.

As a particular example of the above-mentioned types of modifications, an HDV antigen can be modified to change a T cell epitope in a given sequence from one isolate to correspond more closely or exactly with a T cell epitope from a different isolate, or to correspond more closely or exactly with a consensus sequence for the T cell epitope. Indeed, according to the invention, HDV antigens can be designed that incorporate consensus sequences from a variety of HDV genotypes and/or subtypes, or mixtures of sequences from different HDV genotypes and/or subtypes. Alignments of HDV HDAg's across exemplary sequences from each of the major known genotypes can be readily generated using publicly available software, which will inform the generation of consensus sequences, for example. Examples of such modifications are illustrated and exemplified herein.

One exemplary embodiment of the invention relates to an HDV antigen that has the amino acid sequence represented by SEQ ID NO:10, which is a truncated (less than full-length) HDV genotype 1 HDAg-L. This antigen includes the sequence KLEDLERDL or SEQ ID NO:20 (positions 5-13 of SEQ ID NO:10) which is a MHC Class I T cell epitope; and the sequence KLEDENPWL or SEQ ID NO:19 (positions 22-30) which is another MHC Class I T cell epitope (see Table 1 above). Positions 22-140 of SEQ ID NO:10 are regions rich in MHC Class II binding epitopes (see Table 2). This antigen can be produced using the corresponding sequence of any HDV genotype, subgenotype, or strain (i.e., one can use the same amino acid positions of the HDAg-L from a different HDV strain in place of that selected for SEQ ID NO:10). For use in the production of a yeast-based immunotherapeutic composition, yeast (e.g., *Saccharomyces cerevisiae*) are engineered to express the HDV antigen under the control of a suitable promoter. Construction and production of yeast-based immunotherapeutic products is described in more detail below.

As discussed generally above and further described in more detail below, the antigen represented by SEQ ID NO:10, and any other HDV antigen described herein, can also be appended at the N-terminus to add a sequence that imparts resistance to proteasomal degradation and/or stabilizes expression of the protein, such as the following protein: MADEAP (SEQ ID NO:11). Additional suitable N-terminal sequences are discussed below. Optionally, this antigen, and any HDV antigen described herein can be modified to include a C-terminal sequence that may assist with stabilization, identification and/or isolation of the protein, such as a hexa-histidine sequence, which is useful for identifying a protein. By way of an example, a fusion protein comprising the N-terminal sequence of SEQ ID NO:11 and a hexahistidine C-terminus is represented by SEQ ID NO:12, where positions 1-6 of SEQ ID NO:12 correspond to SEQ ID NO:11, positions 7-146 of SEQ ID NO:12 correspond to SEQ ID NO:10, and positions 147-152 of SEQ ID NO:12 is a hexahistidine tag.

The antigen of SEQ ID NO:10, which can be substituted with the corresponding sequence of a different HDV genotype, subgenotype or strain, can also be appended at the N-terminus to add an alpha factor prepro sequence to stabilize expression (represented herein by SEQ ID NO:13 or SEQ ID NO:14, both of which are exemplary alpha factor prepro sequences), and again can optionally be appended at the C-terminus to add a hexa-histidine sequence, if desired. One such fusion protein is represented here by SEQ ID NO:15, which can be substituted with the corresponding sequence of a different HDV strain (incorporating SEQ ID NO:10 and SEQ ID NO:13, as well as a hexa-histidine tag). Positions 1-89 of SEQ ID NO:15 correspond to SEQ ID NO:13, positions 90-229 of SEQ ID NO:15 correspond to SEQ ID NO:10, and positions 230-235 of SEQ ID NO:15 is a hexahistidine tag.

Another HDV antigen useful in the invention is represented by the amino acid sequence of SEQ ID NO:16. In this antigen, one copy of a truncated HDAg (selected to maximize T cell epitopes) from a strain from each of the three different genotypes known as genotypes 1, 2 and 3, is provided as a single fusion protein to produce a more universal construct. This antigen can be produced using the corresponding sequence of any HDV genotype(s) or strain(s), and furthermore, any portion of the HDAg can be used to create such a fusion (i.e., the portions of HDAg's used in SEQ ID NO:16 are exemplary, but smaller portions or larger portions, up to the full length HDAg's could be used). In this construct, a portion of an HDAg from a genotype 1 HDV strain ("genotype1" below) corresponds to positions 1-140 of SEQ ID NO:16; a portion of an HDAg from a genotype 2 strain ("genotype2" below) corresponds to positions 141-280 of SEQ ID NO:16; and a portion of an HDAg from a genotype 3 strain ("genotype3" below) corresponds to positions 281-420 of SEQ ID NO:16.

Another similar construct that may be produced that is related to the sequence represented by SEQ ID NO:16 is a fusion of three or more full-length HDAg-L proteins, where each of the HDAg-L proteins is from a different HDV genotype (e.g., genotypes 1, 2 and 3, or different genotype combinations), except that, as compared to the full-length sequences, each of the HDAg-L proteins has been modified to inactivate the NLS region, as described above (e.g., by substitution and/or deletion of residues within this site). In one example of such a construct, a full-length genotype 1 HDAg-L sequence represented by SEQ ID NO:2 (or a corresponding sequence from another HDV strain) with a deletion of positions 66-75 (the NLS) is linked to a full-length genotype 2 HDAg-L sequence represented by SEQ ID NO:5 (or a corresponding sequence from another HDV strain) with a deletion of positions 66-75 (the NLS) which is linked to a full-length genotype 3 HDAg-L sequence represented by SEQ ID NO:8 (or a corresponding sequence from another HDV strain) with a deletion of positions 66-75 (the NLS). These sequences can also be fused together in a different order, or different or additional HDV genotypes or subgenotypes can be added to the fusion, to produce a "universal" immunotherapeutic composition. In addition, various residues of any of the individual genotype sequences can be modified (e.g., by amino acid substitution) to correspond more closely to a consensus sequence for a given genotype, and/or various residues may be modified (e.g., by amino acid substitution) to correspond more closely to known consensus T cell epitopes that have been associated with immune responses to HDV.

FIG. 1 shows an alignment of the portions of the HDAg used in the construct of SEQ ID NO:16, to illustrate the homology among genotypes used in this fusion protein of SEQ ID NO:16. This alignment also illustrates that it is straightforward to identify the corresponding sequence among different HDV genotypes, subgenotypes or strains/isolates, since each of the sequences in SEQ ID NO:16 is a truncated portion of a full-length HDV HDAg-L.

As with the HDV antigens discussed elsewhere herein, the N- and/or C-termini of SEQ ID NO:16 or a similar fusion protein can be appended to include various sequences (e.g., SEQ ID NO:11, 13 or 14). For example, using an N-terminal peptide of SEQ ID NO:11 and a C-terminal hexahistidine sequence together with SEQ ID NO:16, the fusion protein represented by SEQ ID NO:17 is produced. Positions 1-6 of SEQ ID NO:17 correspond to SEQ ID NO:11; positions 7-426 of SEQ ID NO:17 correspond to SEQ ID NO:16 and positions 427-432 of SEQ ID NO:17 correspond to a hexa-histidine tag. Using the N-terminal sequence of SEQ ID NO:13 together with SEQ ID NO:16 and appending the C-terminus as above, the fusion protein represented by SEQ ID NO:18 is produced, where positions 1-89 of SEQ ID NO:18 correspond to SEQ ID NO:13, positions 90-509 of SEQ ID NO:18 correspond to SEQ ID NO:16, and positions 510-515 of SEQ ID NO:18 correspond to a hexahistidine tag.

Additional HDV antigens, including fusion proteins, and compositions comprising HDV antigens are described in Example 1. In one construct, yeast (e.g., *Saccharomyces cerevisiae*) were engineered to express an HDV antigen under the control of the copper-inducible promoter, CUP1 (an optional promoter can include, but is not limited to, the TEF2 promoter). This HDV antigen comprises a single copy of a genotype 1 HDV HDAg-L. The antigen was constructed using a single copy of the HDAg represented herein as SEQ ID NO:2 as the backbone template, although a corresponding sequence from any other HDV strain/isolate, or any other HDV genotype or subgenotype, could be used instead of the one included in this construct. In this construct, the HDV antigen represented by SEQ ID NO:2 was modified to delete the 10 amino acid residue nuclear localization sequence (i.e., EGAPPAKRAR, or positions 66-75 of SEQ ID NO:2) in order to enhance the potential safety profile of the resulting construct and of the yeast-based immunotherapeutic expressing this antigen, and to potentially enhance the expression of this construct in yeast. This HDV isolate (SEQ ID NO:2) contains several T cell epitopes that are predicted to elicit an immune response against HDV. The resulting protein did not contain known transmembrane domains and was free of extremely hydrophobic elements, and so further modification to account for hydrophobicity was not considered to be an important factor in the design of this HDV antigen. The amino acid sequence of the resulting antigen is represented here by SEQ ID NO:28, which can be substituted with the corresponding sequence from a different HDV strain, genotype or subgenotype. An N-terminal sequence corresponding to SEQ ID NO:11 and a C-terminal sequence of a hexa-histidine tag were added to SEQ ID NO:28 in order to improve the expression of the antigen in yeast (N-terminal sequence) and to facilitate identification of the antigen (C-terminal sequence). A two amino acid linker (Thr-Ser) which introduces a SpeI restriction enzyme site was inserted between SEQ ID NO:11 and SEQ ID NO:28 to facilitate cloning of the construct. The resulting fusion protein has the amino acid sequence represented by SEQ ID NO:30, where positions 1-6 of SEQ ID NO:30 are the N-terminal peptide of SEQ ID NO:11; positions 7-8 of SEQ ID NO:30 are the two amino acid linker; positions 9-212 of SEQ ID NO:30 is the HDV antigen of SEQ ID NO:28; and positions 213-218 of SEQ ID NO:30 is the hexa-histidine tag. SEQ ID NO:30 is encoded by a nucleic acid sequence represented herein by SEQ ID NO:29, which is optimized for expression in yeast.

In a second construct based on the HDV HDAg of SEQ ID NO:2 and described in Example 1, the NLS sequence was retained, in order to evaluate the resulting antigen with respect to yeast biology and expression of the antigen by yeast. The amino acid sequence of the resulting antigen is represented here by SEQ ID NO:31, which can be substituted with the corresponding sequence from a different HDV strain, genotype or subgenotype. An N-terminal sequence corresponding to SEQ ID NO:11 and a C-terminal sequence of a hexa-histidine tag were added to SEQ ID NO:31 in order to improve the expression of the antigen in yeast (N-terminal sequence) and to facilitate identification of the antigen (C-terminal sequence). A two amino acid linker (Thr-Ser) was inserted between SEQ ID NO:11 and SEQ ID NO:31 to facilitate cloning of the construct. The resulting fusion protein has the amino acid sequence represented by SEQ ID NO:33, where positions 1-6 of SEQ ID NO:33 are the N-terminal peptide of SEQ ID NO:11; positions 7-8 of SEQ ID NO:33 are the two amino acid linker; positions 9-222 of SEQ ID NO:33 is the HDV antigen of SEQ ID NO:31; and positions 223-228 of SEQ ID NO:33 is the hexa-histidine tag. SEQ ID NO:33 is encoded by a nucleic acid sequence represented herein by SEQ ID NO:32, which is optimized for expression in yeast.

In a third construct described in Example 1, yeast (e.g., *Saccharomyces cerevisiae*) were engineered to express an HDV antigen under the control of the copper-inducible promoter, CUP1. This antigen is considered to be a more "universal" immunotherapeutic or vaccine, and is a single fusion protein comprising modified HDAg-L from two different HDV genotypes, in this case genotypes 1 and 2. This HDV antigen was constructed using a single copy of the HDAg represented herein as SEQ ID NO:2 (genotype 1) as one backbone template, and a single copy of the HDAg represented herein as SEQ ID NO:5 (genotype 2) as a second backbone template. A corresponding sequence from any other HDV strain/isolate, or any other HDV genotype or subgenotype, could be used instead of one or both of the two sequences included in this construct, and similar fusions can be made using a third, fourth, fifth, or additional genotype, subgenotype or strain. In this fusion protein, the HDV antigen represented by SEQ ID NO:2 was modified to delete the 10 residue nuclear localization sequence (i.e., EGAPPAKRAR, or positions 66-75 of SEQ ID NO:2) in order to enhance the potential safety profile of the resulting construct and of the yeast-based immunotherapeutic expressing this antigen. Similarly, the HDV antigen represented by SEQ ID NO:5 was modified to delete the 10 residue nuclear localization sequence (EGAPPAKRAR, or positions 66-75 of SEQ ID NO:5), also to enhance the safety profile of the resulting construct and of the yeast-based immunotherapeutic expressing this antigen. This fusion protein contains several T cell epitopes in each of the sequences of the HDV isolate templates (SEQ ID NO:2 and SEQ ID NO:5) that are predicted to elicit an immune response against HDV. The amino acid sequence of the resulting antigen is represented here by SEQ ID NO:34, which can be substituted with the corresponding sequence from different HDV strain(s), genotype(s) or subgenotype(s). In SEQ ID NO:34, the sequence of the genotype 1 HDV antigen is represented by positions 1-204 of SEQ ID NO:34 and the sequence of the genotype 2 HDV antigen is represented by positions 205-408 of SEQ ID NO:34.

An N-terminal sequence corresponding to SEQ ID NO:11 and a C-terminal sequence of a hexa-histidine tag were added to SEQ ID NO:34 in order to improve the expression of the antigen in yeast (N-terminal sequence) and to facilitate identification of the antigen (C-terminal sequence). A two amino acid linker (Thr-Ser) was inserted between SEQ ID NO:11 and SEQ ID NO:34 to facilitate cloning of the construct. The resulting fusion protein has the amino acid sequence represented by SEQ ID NO:36, where positions 1-6 of SEQ ID NO:36 are the N-terminal peptide of SEQ ID NO:11; positions 7-8 of SEQ ID NO:36 are the two amino acid linker; positions 9-212 of SEQ ID NO:36 is the genotype 1 HDV antigen from SEQ ID NO:34; positions 213-416 of SEQ ID NO:36 is the genotype 2 antigen from SEQ ID NO:34, and positions 417-422 of SEQ ID NO:36 is the hexa-histidine tag. SEQ ID NO:36 is encoded by a nucleic acid sequence represented herein by SEQ ID NO:35, which is optimized for expression in yeast.

The invention also includes homologues of any of the above-described HDV antigens and fusion proteins, as well as the use of homologues, variants, or mutants of the individual HDV proteins or portions thereof (including any functional and/or immunogenic domains) that are part of such fusion proteins. In one aspect, an HDV antigen useful in the present invention (including any of SEQ ID NO:2, SEQ ID NO:3, SEQ ID NO:5, SEQ ID NO:6, SEQ ID NO:8, SEQ ID NO:9, SEQ ID NO:10, SEQ ID NO:12, SEQ ID NO:15, SEQ ID NO:16, SEQ ID NO:17, SEQ ID NO:18, SEQ ID NO:28, SEQ ID NO:30, SEQ ID NO:31, SEQ ID NO:33, SEQ ID NO:34 or SEQ ID NO:36) comprises at least 80%, 85%, 90%, 91%, 92%, 93%, 94%, 95%, 96%, 97%, 98%, or 99% of the linear sequence of a full-length HDV antigen (HDAg-L or HDAg-S), or of an HDV antigen that has been modified to delete or substitute between 1 and 10 amino acids of the NLS domain, or of a portion of HDAg-L or HDAg-S protein that comprises at least one immunogenic domain of HDAg-L or HDAg-S. In one aspect, the HDV antigen (including any of SEQ ID NO:2, SEQ ID NO:3, SEQ ID NO:5, SEQ ID NO:6, SEQ ID NO:8, SEQ ID NO:9, SEQ ID NO:10, SEQ ID NO:12, SEQ ID NO:15, SEQ ID NO:16, SEQ ID NO:17, SEQ ID NO:18, SEQ ID NO:28, SEQ ID NO:30, SEQ ID NO:31, SEQ ID NO:33, SEQ ID NO:34 or SEQ ID NO:36) is at least 80%, 85%, 90%, 91%, 92%, 93%, 94%, 95%, 96%, 97%, 98%, or 99% identical to a full-length HDV antigen (HDAg-L or HDAg-S), or to an HDV antigen that has been modified to delete or substitute between 1 and 10 amino acids of the NLS domain, or to a portion of HDAg-L or HDAg-S protein that comprises at least one immunogenic domain of HDAg-L or HDAg-S. Addition of an N-terminal expression sequence and the C-terminal tag are optional, and may be selected from several different sequences described elsewhere herein to improve expression, stability, and/or allow for identification and/or purification of the protein, or one or both of the N- or C-terminal sequences are omitted altogether. In addition, many different promoters suitable for use in yeast are known in the art. Furthermore, short intervening linker sequences (e.g., 1, 2, 3, 4, or 5, or larger, amino acid peptides) may be introduced between portions of a fusion protein for a variety of reasons, including the introduction of restriction enzyme sites to facilitate cloning and future manipulation of the constructs.

In some aspects of the invention, amino acid insertions, deletions, and/or substitutions can be made for one, two, three, four, five, six, seven, eight, nine, ten, or more amino acids of a wild-type or reference HDV protein or immunogenic domain thereof, provided that the resulting HDV protein, when used as an antigen in a yeast-HDV immunotherapeutic composition of the invention, elicits an immune response against the target or wild-type or reference HDV protein, which may include an enhanced immune response, a diminished immune response, or a substantially similar immune response. For example, the invention includes the use of HDV agonist antigens, which may include one or more T cell epitopes that have been mutated to enhance the T cell response against the HDV agonist, such as by improving the avidity or affinity of the epitope for an MHC molecule or for the T cell receptor that recognizes the epitope in the context of MHC presentation. HDV protein agonists may therefore improve the potency or efficiency of a T cell response against native HDV proteins that infect a host.

Recombinant nucleic acid molecules and the proteins encoded thereby, including any HDV antigens described herein, as one embodiment of the invention, may be used in yeast-based immunotherapy compositions, or in other embodiments, for any other suitable purpose for HDV antigen(s), including in an in vitro assay, for the production of antibodies, or in another immunotherapy composition, including another vaccine that is not based on the yeast-based immunotherapy described herein (e.g., a viral vector vaccine, a dendritic cell vaccine, or as a component of a fusion or linkage to another immunotherapeutic moiety). Expression of the proteins by yeast is one preferred embodiment, although other expression systems may be used to produce the proteins for applications other than a yeast-based immunotherapy composition.

Yeast-Based Immunotherapy Compositions.

In various embodiments of the invention, the invention includes the use of at least one "yeast-based immunotherapeutic composition" (which phrase may be used interchangeably with "yeast-based immunotherapy product", "yeast-based immunotherapy composition", "yeast-based composition", "yeast-based immunotherapeutic", "yeast-based vaccine", or derivatives of these phrases). An "immunotherapeutic composition" is a composition that elicits an immune response sufficient to achieve at least one therapeutic benefit in a subject. As used herein, yeast-based immunotherapeutic composition refers to a composition that includes a yeast vehicle component and that elicits an immune response sufficient to achieve at least one therapeutic benefit in a subject. More particularly, a yeast-based immunotherapeutic composition is a composition that includes a yeast vehicle component and can elicit or induce an immune response, such as a cellular immune response, including without limitation a T cell-mediated cellular immune response. In one aspect, a yeast-based immunotherapeutic composition useful in the invention is capable of inducing a CD8+ and/or a CD4+ T cell-mediated immune response and in one aspect, a CD8+ and a CD4+ T cell-mediated immune response. Optionally, a yeast-based immunotherapeutic composition is capable of eliciting a humoral immune response. A yeast-based immunotherapeutic composition useful in the present invention can, for example, elicit an immune response in an individual such that the individual is protected from HDV infection and/or is treated for HDV infection or for symptoms resulting from HDV infection.

Yeast-based immunotherapy compositions of the invention may be either "prophylactic" or "therapeutic". When provided prophylactically, the compositions of the present invention are provided in advance of the detection or observation of any identifier or symptom of HDV infection. Such a composition could be administered at birth, in early childhood, or to adults, and may be useful in one embodiment, to immunize populations of individuals in whom HDV infection is a risk, or in whom HBV infection is a risk. The prophylactic administration of the immunotherapy compositions serves to prevent subsequent HDV infection, to resolve an infection more quickly or more completely if HDV infection subsequently ensues, and/or to ameliorate the symptoms of HDV infection if infection subsequently ensues. When provided therapeutically, the immunotherapy compositions are provided at or after the onset of HDV infection, with the goal of ameliorating at least one symptom of the infection and preferably, with a goal of eliminating the infection, providing a long lasting remission of infection, and/or providing long term immunity against subsequent infections or reactivations of the virus.

Typically, a yeast-based immunotherapy composition includes a yeast vehicle and at least one antigen or immunogenic domain thereof expressed by, attached to, or mixed with the yeast vehicle, wherein the antigen is heterologous to the yeast, and wherein the antigen comprises one or more HDV antigens. In some embodiments, the HDV antigen is provided as a fusion protein. Several HDV fusion proteins suitable for use in the compositions and methods of the invention have been described above. In one aspect of the invention, fusion protein can include two or more antigens, such as a repeat of the same antigen or two or more HDAg where each antigen is from a different genotype, sub-genotype or strain. In one aspect, the fusion protein can include two or more immunogenic domains of one or more antigens, or two or more epitopes of one or more antigens.

In any of the yeast-based immunotherapy compositions used in the present invention, the following aspects related to the yeast vehicle are included in the invention. According to the present invention, a yeast vehicle is any yeast cell (e.g., a whole or intact cell) or a derivative thereof (see below) that can be used in conjunction with one or more antigens, immunogenic domains thereof or epitopes thereof in a therapeutic composition of the invention, or in one aspect, the yeast vehicle can be used alone or as an adjuvant. The yeast vehicle can therefore include, but is not limited to, a live, intact (whole) yeast microorganism (i.e., a yeast cell having all its components including a cell wall), a killed (dead) or inactivated intact (whole) yeast microorganism, or derivatives of intact (whole) yeast including: a yeast spheroplast (i.e., a yeast cell lacking a cell wall), a yeast cytoplast (i.e., a yeast cell lacking a cell wall and nucleus), a yeast ghost (i.e., a yeast cell lacking a cell wall, nucleus and cytoplasm), a subcellular yeast membrane extract or fraction thereof (also referred to as a yeast membrane particle and previously as a subcellular yeast particle), any other yeast particle, or a yeast cell wall preparation.

Yeast spheroplasts are typically produced by enzymatic digestion of the yeast cell wall. Such a method is described, for example, in Franzusoff et al., 1991, *Meth. Enzymol.* 194, 662-674., incorporated herein by reference in its entirety.

Yeast cytoplasts are typically produced by enucleation of yeast cells. Such a method is described, for example, in Coon, 1978, *Natl. Cancer Inst. Monogr.* 48, 45-55 incorporated herein by reference in its entirety.

Yeast ghosts are typically produced by resealing a permeabilized or lysed cell and can, but need not, contain at least some of the organelles of that cell. Such a method is described, for example, in Franzusoff et al., 1983, *J. Biol. Chem.* 258, 3608-3614 and Bussey et al., 1979, *Biochim. Biophys. Acta* 553, 185-196, each of which is incorporated herein by reference in its entirety.

A yeast membrane particle (subcellular yeast membrane extract or fraction thereof) refers to a yeast membrane that lacks a natural nucleus or cytoplasm. The particle can be of any size, including sizes ranging from the size of a natural yeast membrane to microparticles produced by sonication or other membrane disruption methods known to those skilled in the art, followed by resealing. A method for producing subcellular yeast membrane extracts is described, for example, in Franzusoff et al., 1991, *Meth. Enzymol.* 194, 662-674. One may also use fractions of yeast membrane particles that contain yeast membrane portions and, when the antigen or other protein was expressed recombinantly by the yeast prior to preparation of the yeast membrane particles, the antigen or other protein of interest. Antigens or other proteins of interest can be carried inside the membrane, on either surface of the membrane, or combinations thereof (i.e., the protein can be both inside and outside the membrane and/or spanning the membrane of the yeast membrane particle). In one embodiment, a yeast membrane particle is a recombinant yeast membrane particle that can be an intact, disrupted, or disrupted and resealed yeast membrane that includes at least one desired antigen or other protein of interest on the surface of the membrane or at least partially embedded within the membrane.

An example of a yeast cell wall preparation is a preparation of isolated yeast cell walls carrying an antigen on its surface or at least partially embedded within the cell wall such that the yeast cell wall preparation, when administered to an animal, stimulates a desired immune response against a disease target.

Any yeast strain can be used to produce a yeast vehicle of the present invention. Yeast are unicellular microorganisms that belong to one of three classes: Ascomycetes, Basidiomycetes and Fungi Imperfecti. One consideration for the selection of a type of yeast for use as an immune modulator is the pathogenicity of the yeast. In one embodiment, the yeast is a non-pathogenic strain such as *Saccharomyces cerevisiae*. The selection of a non-pathogenic yeast strain minimizes any adverse effects to the individual to whom the yeast vehicle is administered. However, pathogenic yeast may be used if the pathogenicity of the yeast can be negated by any means known to one of skill in the art (e.g., mutant strains). In accordance with one aspect of the present invention, nonpathogenic yeast strains are used.

Genera of yeast strains that may be used in the invention include but are not limited to *Saccharomyces, Candida, Cryptococcus, Hansenula, Kluyveromyces, Pichia, Rhodotorula, Schizosaccharomyces* and *Yarrowia*. In one aspect, yeast genera are selected from *Saccharomyces, Candida, Hansenula, Pichia* or *Schizosaccharomyces*, and in one aspect, yeast genera are selected from *Saccharomyces, Hansenula*, and *Pichia*, and in one aspect, *Saccharomyces* is used. Species of yeast strains that may be used in the invention include but are not limited to *Saccharomyces cerevisiae, Saccharomyces carlsbergensis, Candida albicans, Candida kefyr, Candida tropicalis, Cryptococcus laurentii, Cryptococcus neoformans, Hansenula anomala, Hansenula polymorpha, Kluyveromyces fragilis, Kluyveromyces lactis, Kluyveromyces marxianus* var. *lactis, Pichia pastoris, Rhodotorula rubra, Schizosaccharomyces pombe*, and *Yarrowia lypolytica*. It is to be appreciated that a number of these species include a variety of subspecies, types, subtypes, etc. that are intended to be included within the aforementioned species. In one aspect, yeast species used in the invention include *S. cerevisiae, C. albicans, H. polymorpha, P. pastoris* and *S. pombe*. *S. cerevisiae* is useful as it is relatively easy to manipulate and being "Generally Recognized As Safe" or "GRAS" for use as food additives (GRAS, FDA proposed Rule 62FR18938, Apr. 17, 1997). One embodiment of the present invention is a yeast strain that is capable of replicating plasmids to a particularly high copy number, such as a *S. cerevisiae* cir° strain. The *S. cerevisiae* strain is one such strain that is capable of supporting expression vectors that allow one or more target antigen(s) and/or antigen fusion protein(s) and/or other proteins to be expressed at high levels. In addition, any mutant yeast strains can be used in the present invention, including those that exhibit reduced post-translational modifications of expressed target antigens or other proteins, such as mutations in the enzymes that extend N-linked glycosylation.

In most embodiments of the invention, the yeast-based immunotherapy composition includes at least one antigen, immunogenic domain thereof, or epitope thereof. The antigens contemplated for use in this invention include any HDV antigen or immunogenic domain thereof, including mutants, variants and agonists of HDV proteins or domains thereof, against which it is desired to elicit an immune response for the purpose of prophylactically or therapeutically immunizing a host against HDV infection. HDV antigens that are useful in various embodiments of the invention have been described in detail above.

As discussed above, the compositions of the invention include at least one HDV antigen and/or at least one immunogenic domain of at least one HDV antigen for immunizing a subject. In some embodiments, the antigen is a fusion protein, several examples of which have been described above.

Optionally, proteins, including fusion proteins, which are used as a component of the yeast-based immunotherapeutic composition of the invention are produced using constructs that are particularly useful for improving or enhancing the expression, or the stability of expression, of recombinant antigens in yeast. Typically, the desired antigenic protein(s) or peptide(s) are fused at their amino-terminal end to: (a) a specific synthetic peptide that stabilizes the expression of the fusion protein in the yeast vehicle or prevents posttranslational modification of the expressed fusion protein (such peptides are described in detail, for example, in U.S. Patent Publication No. 2004-0156858 A1, published Aug. 12, 2004, incorporated herein by reference in its entirety); (b) at least a portion of an endogenous yeast protein, including but not limited to alpha factor, wherein either fusion partner provides improved stability of expression of the protein in the yeast and/or a prevents post-translational modification of the proteins by the yeast cells (such proteins are also described in detail, for example, in U.S. Patent Publication No. 2004-0156858 A1, supra); and/or (c) at least a portion of a yeast protein that causes the fusion protein to be expressed on the surface of the yeast (e.g., an Aga protein, described in more detail herein). In addition, the present invention optionally includes the use of peptides that are fused to the C-terminus of the antigen-encoding construct, particularly for use in the selection and identification of the protein. Such peptides include, but are not limited to, any synthetic or natural peptide, such as a peptide tag (e.g., 6×His) or any other short epitope tag. Peptides attached to the C-terminus of an antigen according to the invention can be used with or without the addition of the N-terminal peptides discussed above.

In one embodiment, a synthetic peptide useful in a fusion protein is linked to the N-terminus of the antigen, the peptide consisting of at least two amino acid residues that are heterologous to the antigen, wherein the peptide stabilizes the expression of the fusion protein in the yeast vehicle or prevents posttranslational modification of the expressed fusion protein. The synthetic peptide and N-terminal portion of the antigen together form a fusion protein that has the following requirements: (1) the amino acid residue at position one of the fusion protein is a methionine (i.e., the first amino acid in the synthetic peptide is a methionine); (2) the amino acid residue at position two of the fusion protein is not a glycine or a proline (i.e., the second amino acid in the synthetic peptide is not a glycine or a proline); (3) none of the amino acid residues at positions 2-6 of the fusion protein is a methionine (i.e., the amino acids at positions 2-6, whether part of the synthetic peptide or the protein, if the synthetic peptide is shorter than 6 amino acids, do not include a methionine); and (4) none of the amino acids at positions 2-6 of the fusion protein is a lysine or an arginine (i.e., the amino acids at positions 2-6, whether part of the synthetic peptide or the protein, if the synthetic peptide is shorter than 5 amino acids, do not include a lysine or an arginine). The synthetic peptide can be as short as two amino acids, but in one aspect, is 2-6 amino acids (including 3, 4, 5 amino acids), and can be longer than 6 amino acids, in whole integers, up to about 200 amino acids, 300 amino acids, 400 amino acids, 500 amino acids, or more.

In one embodiment, a fusion protein comprises an amino acid sequence of M-X2-X3-X4-X5-X6, wherein M is methionine; wherein X2 is any amino acid except glycine, proline, lysine or arginine; wherein X3 is any amino acid except methionine, lysine or arginine; wherein X4 is any amino acid except methionine, lysine or arginine; wherein X5 is any amino acid except methionine, lysine or arginine; and wherein X6 is any amino acid except methionine, lysine or arginine. In one embodiment, the X6 residue is a proline. An exemplary synthetic sequence that enhances the stability of expression of an antigen in a yeast cell and/or prevents post-translational modification of the protein in the yeast includes the sequence M-A-D-E-A-P (SEQ ID NO:11). Another exemplary synthetic sequence with the same properties is M-V. In addition to the enhanced stability of the expression product, these fusion partners do not appear to negatively impact the immune response against the immunizing antigen in the construct. In addition, the synthetic fusion peptides can be designed to provide an epitope that can be recognized by a selection agent, such as an antibody.

In one embodiment, the HDV antigen is linked at the N-terminus to a yeast protein, such as an alpha factor prepro sequence (also referred to as the alpha factor signal leader sequence, the amino acid sequence of which is exemplified herein by SEQ ID NO:13 or SEQ ID NO:14. Other sequences for yeast alpha factor prepro sequence are known in the art and are encompassed for use in the present invention.

In one aspect of the invention, the yeast vehicle is manipulated such that the antigen is expressed or provided by delivery or translocation of an expressed protein product, partially or wholly, on the surface of the yeast vehicle (extracellular expression). One method for accomplishing this aspect of the invention is to use a spacer arm for positioning one or more protein(s) on the surface of the yeast vehicle. For example, one can use a spacer arm to create a fusion protein of the antigen(s) or other protein of interest with a protein that targets the antigen(s) or other protein of interest to the yeast cell wall. For example, one such protein that can be used to target other proteins is a yeast protein (e.g., cell wall protein 2 (cwp2), Aga2, Pir4 or Flo1 protein) that enables the antigen(s) or other protein to be targeted to the yeast cell wall such that the antigen or other protein is located on the surface of the yeast. Proteins other than yeast proteins may be used for the spacer arm; however, for any spacer arm protein, it is most desirable to have the immunogenic response be directed against the target antigen rather than the spacer arm protein. As such, if other proteins are used for the spacer arm, then the spacer arm protein that is used should not generate such a large immune response to the spacer arm protein itself such that the immune response to the target antigen(s) is overwhelmed. One of skill in the art should aim for a small immune response to the spacer arm protein relative to the immune response for the target antigen(s). Spacer arms can be constructed to have cleavage sites (e.g., protease cleavage sites) that allow the antigen to be readily removed or processed away from the yeast, if desired. Any known method of determining the magnitude of immune responses can be used (e.g., antibody production, lytic assays, etc.) and are readily known to one of skill in the art.

Another method for positioning the target antigen(s) or other proteins to be exposed on the yeast surface is to use signal sequences such as glycosylphosphatidyl inositol (GPI) to anchor the target to the yeast cell wall. Alternatively, positioning can be accomplished by appending signal sequences that target the antigen(s) or other proteins of interest into the secretory pathway via translocation into the endoplasmic reticulum (ER) such that the antigen binds to a protein which is bound to the cell wall (e.g., cwp).

In one aspect, the spacer arm protein is a yeast protein. The yeast protein can consist of between about two and about 800 amino acids of a yeast protein. In one embodiment, the yeast protein is about 10 to 700 amino acids. In another embodiment, the yeast protein is about 40 to 600 amino acids. Other embodiments of the invention include the yeast protein being at least 250 amino acids, at least 300 amino acids, at least 350 amino acids, at least 400 amino acids, at least 450 amino acids, at least 500 amino acids, at least 550 amino acids, at least 600 amino acids, or at least 650 amino acids. In one embodiment, the yeast protein is at least 450 amino acids in length. Another consideration for optimizing antigen surface expression, if that is desired, is whether the antigen and spacer arm combination should be expressed as a monomer or as dimer or as a trimer, or even more units connected together. This use of monomers, dimers, trimers, etc. allows for appropriate spacing or folding of the antigen such that some part, if not all, of the antigen is displayed on the surface of the yeast vehicle in a manner that makes it more immunogenic.

Use of yeast proteins can stabilize the expression of fusion proteins in the yeast vehicle, prevents posttranslational modification of the expressed fusion protein, and/or targets the fusion protein to a particular compartment in the yeast (e.g., to be expressed on the yeast cell surface). For delivery into the yeast secretory pathway, exemplary yeast proteins to use include, but are not limited to: Aga (including, but not limited to, Aga1 and/or Aga2); SUC2 (yeast invertase); alpha factor signal leader sequence; CPY; Cwp2p for its localization and retention in the cell wall; BUD genes for localization at the yeast cell bud during the initial phase of daughter cell formation; Flo1p; Pir2p; and Pir4p.

Other sequences can be used to target, retain and/or stabilize the protein to other parts of the yeast vehicle, for example, in the cytosol or the mitochondria or the endoplasmic reticulum or the nucleus. Examples of suitable yeast protein that can be used for any of the embodiments above include, but are not limited to, TK, AF, SEC7; phosphoenolpyruvate carboxykinase PCK1, phosphoglycerokinase PGK and triose phosphate isomerase TPI gene products for their repressible expression in glucose and cytosolic localization; the heat shock proteins SSA1, SSA3, SSA4, SSC1, whose expression is induced and whose proteins are more thermostable upon exposure of cells to heat treatment; the mitochondrial protein CYC1 for import into mitochondria; ACT1.

Methods of producing yeast vehicles and expressing, combining and/or associating yeast vehicles with antigens and/or other proteins and/or agents of interest to produce yeast-based immunotherapy compositions are contemplated by the invention.

According to the present invention, the term "yeast vehicle-antigen complex" or "yeast-antigen complex" is used generically to describe any association of a yeast vehicle with an antigen, and can be used interchangeably with "yeast-based immunotherapy composition" when such composition is used to elicit an immune response as described above. Such association includes expression of the antigen by the yeast (a recombinant yeast), introduction of an antigen into a yeast, physical attachment of the antigen to the yeast, and mixing of the yeast and antigen together, such as in a buffer or other solution or formulation. These types of complexes are described in detail below.

In one embodiment, a yeast cell used to prepare the yeast vehicle is transfected with a heterologous nucleic acid molecule encoding a protein (e.g., the antigen) such that the protein is expressed by the yeast cell. Such a yeast is also referred to herein as a recombinant yeast or a recombinant yeast vehicle. The yeast cell can then be loaded into the dendritic cell as an intact cell, or the yeast cell can be killed, or it can be derivatized such as by formation of yeast spheroplasts, cytoplasts, ghosts, or subcellular particles, any of which is followed by loading of the derivative into the dendritic cell. Yeast spheroplasts can also be directly transfected with a recombinant nucleic acid molecule (e.g., the spheroplast is produced from a whole yeast, and then transfected) in order to produce a recombinant spheroplast that expresses an antigen or other protein.

In general, the yeast vehicle and antigen(s) and/or other agents can be associated by any technique described herein. In one aspect, the yeast vehicle was loaded intracellularly with the antigen(s) and/or agent(s). In another aspect, the antigen(s) and/or agent(s) was covalently or non-covalently attached to the yeast vehicle. In yet another aspect, the yeast vehicle and the antigen(s) and/or agent(s) were associated by mixing. In another aspect, and in one embodiment, the antigen(s) and/or agent(s) is expressed recombinantly by the yeast vehicle or by the yeast cell or yeast spheroplast from which the yeast vehicle was derived.

A number of antigens and/or other proteins to be produced by a yeast vehicle of the present invention is any number of antigens and/or other proteins that can be reasonably produced by a yeast vehicle, and typically ranges from at least one to at least about 6 or more, including from about 2 to about 6 heterologous antigens and or other proteins.

Expression of an antigen or other protein in a yeast vehicle of the present invention is accomplished using techniques known to those skilled in the art. Briefly, a nucleic acid molecule encoding at least one desired antigen or other protein is inserted into an expression vector in such a manner that the nucleic acid molecule is operatively linked to a transcription control sequence in order to be capable of effecting either constitutive or regulated expression of the nucleic acid molecule when transformed into a host yeast cell. Nucleic acid molecules encoding one or more antigens and/or other proteins can be on one or more expression vectors operatively linked to one or more expression control sequences. Particularly important expression control sequences are those which control transcription initiation, such as promoter and upstream activation sequences. Any suitable yeast promoter can be used in the present invention and a variety of such promoters are known to those skilled in the art. Promoters for expression in Saccharomyces cerevisiae include, but are not limited to, promoters of genes encoding the following yeast proteins: alcohol dehydrogenase I (ADH1) or II (ADH2), CUP1, phosphoglycerate kinase (PGK), triose phosphate isomerase (TPI), translational elongation factor EF-1 alpha (TEF2), glyceraldehyde- 3-phosphate dehydrogenase (GAPDH; also referred to as TDH3, for triose phosphate dehydrogenase), galactokinase (GAL1), galactose-1-phosphate uridyl-transferase (GAL7), UDP-galactose epimerase (GAL10), cytochrome c1 (CYC1), Sec7 protein (SEC7) and acid phosphatase (PHO5), including hybrid promoters such as ADH2/GAPDH and CYC1/GAL10 promoters, and including the ADH2/GAPDH promoter, which is induced when glucose concentrations in the cell are low (e.g., about 0.1 to about 0.2 percent), as well as the CUP1 promoter and the TEF2 promoter. Likewise, a number of upstream activation sequences (UASs), also referred to as enhancers, are known. Upstream activation sequences for expression in *Saccharomyces cerevisiae* include, but are not limited to, the UASs of genes encoding the following proteins: PCK1, TPI, TDH3, CYC1, ADH1, ADH2, SUC2, GAL1, GAL7 and GAL10, as well as other UASs activated by the GAL4 gene product, with the ADH2 UAS being used in one aspect. Since the ADH2 UAS is activated by the ADR1 gene product, it may be preferable to overexpress the ADR1 gene when a heterologous gene is operatively linked to the ADH2 UAS. Transcription termination sequences for expression in *Saccharomyces cerevisiae* include the termination sequences of the α-factor, GAPDH, and CYC1 genes.

Transcription control sequences to express genes in methyltrophic yeast include the transcription control regions of the genes encoding alcohol oxidase and formate dehydrogenase.

Transfection of a nucleic acid molecule into a yeast cell according to the present invention can be accomplished by any method by which a nucleic acid molecule can be introduced into the cell and includes, but is not limited to, diffusion, active transport, bath sonication, electroporation, microinjection, lipofection, adsorption, and protoplast fusion. Transfected nucleic acid molecules can be integrated into a yeast chromosome or maintained on extrachromosomal vectors using techniques known to those skilled in the art. Examples of yeast vehicles carrying such nucleic acid molecules are disclosed in detail herein. As discussed above, yeast cytoplast, yeast ghost, and yeast membrane particles or cell wall preparations can also be produced recombinantly by transfecting intact yeast microorganisms or yeast spheroplasts with desired nucleic acid molecules, producing the antigen therein, and then further manipulating the microorganisms or spheroplasts using techniques known to those skilled in the art to produce cytoplast, ghost or subcellular yeast membrane extract or fractions thereof containing desired antigens or other proteins.

Effective conditions for the production of recombinant yeast vehicles and expression of the antigen and/or other protein by the yeast vehicle include an effective medium in which a yeast strain can be cultured. An effective medium is typically an aqueous medium comprising assimilable carbohydrate, nitrogen and phosphate sources, as well as appropriate salts, minerals, metals and other nutrients, such as vitamins and growth factors. The medium may comprise complex nutrients or may be a defined minimal medium. Yeast strains of the present invention can be cultured in a variety of containers, including, but not limited to, bioreactors, Erlenmeyer flasks, test tubes, microtiter dishes, and Petri plates. Culturing is carried out at a temperature, pH and oxygen content appropriate for the yeast strain. Such culturing conditions are well within the expertise of one of ordinary skill in the art (see, for example, Guthrie et al. (eds.), 1991, Methods in Enzymology, vol. 194, Academic Press, San Diego).

In some embodiments of the invention, yeast are grown under neutral pH conditions. As used herein, the general use of the term "neutral pH" refers to a pH range between about pH 5.5 and about pH 8, and in one aspect, between about pH 6 and about 8. One of skill in the art will appreciate that minor fluctuations (e.g., tenths or hundredths) can occur when measuring with a pH meter. As such, the use of neutral pH to grow yeast cells means that the yeast cells are grown in neutral pH for the majority of the time that they are in culture. In one embodiment, yeast are grown in a medium maintained at a pH level of at least 5.5 (i.e., the pH of the culture medium is not allowed to drop below pH 5.5). In another aspect, yeast are grown at a pH level maintained at about 6, 6.5, 7, 7.5 or 8. The use of a neutral pH in culturing yeast promotes several biological effects that are desirable characteristics for using the yeast as vehicles for immunomodulation. For example, culturing the yeast in neutral pH allows for good growth of the yeast without negative effect on the cell generation time (e.g., slowing of doubling time). The yeast can continue to grow to high densities without losing their cell wall pliability. The use of a neutral pH allows for the production of yeast with pliable cell walls and/or yeast that are more sensitive to cell wall digesting enzymes (e.g., glucanase) at all harvest densities. This trait is desirable because yeast with flexible cell walls can induce different or improved immune responses as compared to yeast grown under more acidic conditions, e.g., by promoting the secretion of cytokines by antigen presenting cells that have phagocytosed the yeast (e.g., TH1-type cytokines including, but not limited to, IFN-γ, interleukin-12 (IL-12), and IL-2, as well as proinflammatory cytokines such as IL-6). In addition, greater accessibility to the antigens located in the cell wall is afforded by such culture methods. In another aspect, the use of neutral pH for some antigens allows for release of the di-sulfide bonded antigen by treatment with dithiothreitol (DTT) that is not possible when such an antigen-expressing yeast is cultured in media at lower pH (e.g., pH 5).

In one embodiment, control of the amount of yeast glycosylation is used to control the expression of antigens by the yeast, particularly on the surface. The amount of yeast glycosylation can affect the immunogenicity and antigenicity of the antigen expressed on the surface, since sugar moieties tend to be bulky. As such, the existence of sugar moieties on the surface of yeast and its impact on the three-dimensional space around the target antigen(s) should be considered in the modulation of yeast according to the invention. Any method can be used to reduce the amount of glycosylation of the yeast (or increase it, if desired). For example, one could use a yeast mutant strain that has been selected to have low glycosylation (e.g., mnn1, och1 and mnn9 mutants), or one could eliminate by mutation the glycosylation acceptor sequences on the target antigen. Alternatively, one could use a yeast with abbreviated glycosylation patterns, e.g., *Pichia*. One can also treat the yeast using methods that reduce or alter the glycosylation.

In one embodiment of the present invention, as an alternative to expression of an antigen or other protein recombinantly in the yeast vehicle, a yeast vehicle is loaded intracellularly with the protein or peptide, or with carbohydrates or other molecules that serve as an antigen and/or are useful as immunomodulatory agents or biological response modifiers according to the invention. Subsequently, the yeast vehicle, which now contains the antigen and/or other proteins intracellularly, can be administered to an individual or loaded into a carrier such as a dendritic cell. Peptides and proteins can be inserted directly into yeast vehicles of the present invention by techniques known to those skilled in the art, such as by diffusion, active transport, liposome fusion, electroporation, phagocytosis, freeze-thaw cycles and bath sonication. Yeast vehicles that can be directly loaded with peptides, proteins, carbohydrates, or other molecules include intact yeast, as well as spheroplasts, ghosts or cytoplasts, which can be loaded with antigens and other agents after production. Alternatively, intact yeast can be loaded with the antigen and/or agent, and then spheroplasts, ghosts, cytoplasts, or subcellular particles can be prepared therefrom. Any number of antigens and/or other agents can be loaded into a yeast vehicle in this embodiment, from at least 1, 2, 3, 4 or any whole integer up to hundreds or thousands of antigens and/or other agents, such as would be provided by the loading of a microorganism or portions thereof, for example.

In another embodiment of the present invention, an antigen and/or other agent is physically attached to the yeast vehicle. Physical attachment of the antigen and/or other agent to the yeast vehicle can be accomplished by any method suitable in the art, including covalent and noncovalent association methods which include, but are not limited to, chemically crosslinking the antigen and/or other agent to the outer surface of the yeast vehicle or biologically linking the antigen and/or other agent to the outer surface of the yeast vehicle, such as by using an antibody or other binding partner. Chemical cross-linking can be achieved, for example, by methods including glutaraldehyde linkage, photoaffinity labeling, treatment with carbodiimides, treatment with chemicals capable of linking di-sulfide bonds, and treatment with other cross-linking chemicals standard in the art. Alternatively, a chemical can be contacted with the yeast vehicle that alters the charge of the lipid bilayer of yeast membrane or the composition of the cell wall so that the outer surface of the yeast is more likely to fuse or bind to antigens and/or other agent having particular charge characteristics. Targeting agents such as antibodies, binding peptides, soluble receptors, and other ligands may also be incorporated into an antigen as a fusion protein or otherwise associated with an antigen for binding of the antigen to the yeast vehicle.

When the antigen or other protein is expressed on or physically attached to the surface of the yeast, spacer arms may, in one aspect, be carefully selected to optimize antigen or other protein expression or content on the surface. The size of the spacer arm(s) can affect how much of the antigen or other protein is exposed for binding on the surface of the yeast. Thus, depending on which antigen(s) or other protein(s) are being used, one of skill in the art will select a spacer arm that effectuates appropriate spacing for the antigen or other protein on the yeast surface. In one embodiment, the spacer arm is a yeast protein of at least 450 amino acids. Spacer arms have been discussed in detail above.

In yet another embodiment, the yeast vehicle and the antigen or other protein are associated with each other by a more passive, non-specific or non-covalent binding mechanism, such as by gently mixing the yeast vehicle and the antigen or other protein together in a buffer or other suitable formulation (e.g., admixture).

In one embodiment of the invention, the yeast vehicle and the antigen or other protein are both loaded intracellularly into a carrier such as a dendritic cell or macrophage to form the therapeutic composition or vaccine of the present invention. Alternatively, an antigen or other protein can be loaded into a dendritic cell in the absence of the yeast vehicle.

In one embodiment, intact yeast (with or without expression of heterologous antigens or other proteins) can be ground up or processed in a manner to produce yeast cell wall preparations, yeast membrane particles or yeast fragments (i.e., not intact) and the yeast fragments can, in some embodiments, be provided with or administered with other compositions that include antigens (e.g., DNA vaccines, protein subunit vaccines, killed or inactivated pathogens) to enhance immune responses. For example, enzymatic treatment, chemical treatment or physical force (e.g., mechanical shearing or sonication) can be used to break up the yeast into parts that are used as an adjuvant.

In one embodiment of the invention, yeast vehicles useful in the invention include yeast vehicles that have been killed or inactivated. Killing or inactivating of yeast can be accomplished by any of a variety of suitable methods known in the art. For example, heat inactivation of yeast is a standard way of inactivating yeast, and one of skill in the art can monitor the structural changes of the target antigen, if desired, by standard methods known in the art. Alternatively, other methods of inactivating the yeast can be used, such as chemical, electrical, radioactive or UV methods. See, for example, the methodology disclosed in standard yeast culturing textbooks such as *Methods of Enzymology*, Vol. 194, Cold Spring Harbor Publishing (1990). Any of the inactivation strategies used should take the secondary, tertiary or quaternary structure of the target antigen into consideration and preserve such structure as to optimize its immunogenicity.

Yeast vehicles can be formulated into yeast-based immunotherapy compositions or products of the present invention, including preparations to be administered to a subject directly or first loaded into a carrier such as a dendritic cell, using a number of techniques known to those skilled in the art. For example, yeast vehicles can be dried by lyophilization. Formulations comprising yeast vehicles can also be prepared by packing yeast in a cake or a tablet, such as is done for yeast used in baking or brewing operations. In addition, yeast vehicles can be mixed with a pharmaceutically acceptable excipient, such as an isotonic buffer that is tolerated by a host or host cell. Examples of such excipients include water, saline, Ringer's solution, dextrose solution, Hank's solution, and other aqueous physiologically balanced salt solutions. Nonaqueous vehicles, such as fixed oils, sesame oil, ethyl oleate, or triglycerides may also be used. Other useful formulations include suspensions containing viscosity-enhancing agents, such as sodium carboxymethylcellulose, sorbitol, glycerol or dextran. Excipients can also contain minor amounts of additives, such as substances that enhance isotonicity and chemical stability. Examples of buffers include phosphate buffer, bicarbonate buffer and Tris buffer, while examples of preservatives include thimerosal, m- or o-cresol, formalin and benzyl alcohol. Standard formulations can either be liquid injectables or solids which can be taken up in a suitable liquid as a suspension or solution for injection. Thus, in a non-liquid formulation, the excipient can comprise, for example, dextrose, human serum albumin, and/or preservatives to which sterile water or saline can be added prior to administration.

In one embodiment of the present invention, a composition can include additional agents, which may also be referred to as biological response modifier compounds, or the ability to produce such agents/modifiers. For example, a yeast vehicle can be transfected with or loaded with at least one antigen and at least one agent/biological response modifier compound, or a composition of the invention can be administered in conjunction with at least one agent/biological response modifier. Biological response modifiers include adjuvants and other compounds that can modulate immune responses, which may be referred to as immunomodulatory compounds, as well as compounds that modify the biological activity of another compound or agent, such as a yeast-based immunotherapeutic, such biological activity not being limited to immune system effects. Certain immunomodulatory compounds can stimulate a protective immune response whereas others can suppress a harmful immune response, and whether an immunomodulatory is useful in combination with a given yeast-based immunotherapeutic may depend, at least in part, on the disease state or condition to be treated or prevented, and/or on the individual who is to be treated. Certain biological response modifiers preferentially enhance a cell-mediated immune response whereas others preferentially enhance a humoral immune response (i.e., can stimulate an immune response in which there is an increased level of cell-mediated compared to humoral immunity, or vice versa.). Certain biological response modifiers have one or more properties in common with the biological properties of yeast-based immunotherapeutics or enhance or complement the biological properties of yeast-based immunotherapeutics. There are a number of techniques known to those skilled in the art to measure stimulation or suppression of immune responses, as well as to differentiate cell-mediated immune responses from humoral immune responses, and to differentiate one type of cell-mediated response from another (e.g., a TH17 response versus a TH1 response).

Agents/biological response modifiers useful in the invention may include, but are not limited to, cytokines, chemokines, hormones, lipidic derivatives, peptides, proteins, polysaccharides, small molecule drugs, antibodies and antigen binding fragments thereof (including, but not limited to, anti-cytokine antibodies, anti-cytokine receptor antibodies, anti-chemokine antibodies), vitamins, polynucleotides, nucleic acid binding moieties, aptamers, and growth modulators. Some suitable agents include, but are not limited to, IL-1 or agonists of IL-1 or of IL-1R, anti-IL-1 or other IL-1 antagonists; IL-6 or agonists of IL-6 or of IL-6R, anti-IL-6 or other IL-6 antagonists; IL-12 or agonists of IL-12 or of IL-12R, anti-IL-12 or other IL-12 antagonists; IL-17 or agonists of IL-17 or of IL-17R, anti-IL-17 or other IL-17 antagonists; IL-21 or agonists of IL-21 or of IL-21R, anti-IL-21 or other IL-21 antagonists; IL-22 or agonists of IL-22 or of IL-22R, anti-IL-22 or other IL-22 antagonists; IL-23 or agonists of IL-23 or of IL-23R, anti-IL-23 or other IL-23 antagonists; IL-25 or agonists of IL-25 or of IL-25R, anti-IL-25 or other IL-25 antagonists; IL-27 or agonists of IL-27 or of IL-27R, anti-IL-27 or other IL-27 antagonists; type I interferon (including IFN-α) or agonists or antagonists of type I interferon or a receptor thereof; type II interferon (including IFN-β) or agonists or antagonists of type II interferon or a receptor thereof; anti-CD40, CD40L, anti-CTLA-4 antibody (e.g., to release anergic T cells); T cell co-stimulators (e.g., anti-CD137, anti-CD28, anti-CD40); alemtuzumab (e.g., CamPath®), denileukin diftitox (e.g., ONTAK®); anti-CD4; anti-CD25; anti-PD-1, anti-PD-L1, anti-PD-L2; agents that block FOXP3 (e.g., to abrogate the activity/kill CD4+/CD25+ T regulatory cells); Flt3 ligand, imiquimod (Aldara™), granulocyte-macrophage colony stimulating factor (GM-CSF); granulocyte-colony stimulating factor (G-CSF), sargramostim (Leukine®); hormones including without limitation prolactin and growth hormone; Toll-like receptor (TLR) agonists, including but not limited to TLR-2 agonists, TLR-4 agonists, TLR-7 agonists, and TLR-9 agonists; TLR antagonists, including but not limited to TLR-2 antagonists, TLR-4 antagonists, TLR-7 antagonists, and TLR-9 antagonists; anti-inflammatory agents and immunomodulators, including but not limited to, COX-2 inhibitors (e.g., Celecoxib, NSAIDS), glucocorticoids, statins, and thalidomide and analogues thereof including IMiD™s (which are structural and functional analogues of thalidomide (e.g., REVLIMID® (lenalidomide), ACTIMID® (pomalidomide)); proinflammatory agents, such as fungal or bacterial components or any proinflammatory cytokine or chemokine; immunotherapeutic vaccines including, but not limited to, virus-based vaccines, bacteria-based vaccines, or antibody-based vaccines; and any other immunomodulators, immunopotentiators, anti-inflammatory agents, and/or proinflammatory agents. Any combination of such agents is contemplated by the invention, and any of such agents combined with or administered in a protocol with (e.g., concurrently, sequentially, or in other formats with) a yeast-based immunotherapeutic is a composition encompassed by the invention. Such agents are well known in the art. These agents may be used alone or in combination with other agents described herein.

Agents can include agonists and antagonists of a given protein or peptide or domain thereof. As used herein, an "agonist" is any compound or agent, including without limitation small molecules, proteins, peptides, antibodies, nucleic acid binding agents, etc., that binds to a receptor or ligand and produces or triggers a response, which may include agents that mimic the action of a naturally occurring substance that binds to the receptor or ligand. An "antagonist" is any compound or agent, including without limitation small molecules, proteins, peptides, antibodies, nucleic acid binding agents, etc., that blocks or inhibits or reduces the action of an agonist.

Compositions of the invention can further include or can be administered with (concurrently, sequentially, or intermittently with) any other compounds or compositions that are useful for preventing or treating HDV infection or any compounds that treat or ameliorate any symptom of HDV infection. Such agents include, but are not limited to, small molecule drugs against HDAg, or interferons, such as interferon-α2a or pegylated interferon-α2a (PEGASYS®). In addition, compositions of the invention can be used together with other immunotherapeutic compositions, including prophylactic and/or therapeutic immunotherapy. While no immunotherapy compositions have been approved in the U.S. for the treatment of HDV, such compositions can include HDV protein or epitope subunit vaccines, HDV viral vector vaccines, cytokines, and/or other immunomodulatory agents (e.g., TLR agonists, immunomodulatory drugs).

The invention also includes a kit comprising any of the compositions described herein, or any of the individual components of the compositions described herein.

Methods for Administration or Use of Compositions of the Invention

Compositions of the invention, which can include any one or more (e.g., combinations of two, three, four, five, or more) yeast-based immunotherapeutic compositions described herein, HDV antigens including HDV proteins and fusion proteins, and/or recombinant nucleic acid molecules encoding such HDV proteins or fusion proteins described above, and other compositions comprising such yeast-based compositions, antigens, proteins, fusion proteins, or recombinant molecules described herein, can be used in a variety of in vivo and in vitro methods, including, but not limited to, to treat and/or prevent HDV infection and its sequelae, in diagnostic assays for HDV, or to produce antibodies against HDV.

HDV infection is detected most typically by measurement of HDV RNA, detection of the HDV antigen (HDAg), and/or detection of anti-HDV (antibodies against HDV).

Detection of HDV RNA can be performed, for example, by nucleotide hybridization assays (which may include in situ hybridization) or reverse transcriptase-polymerase chain reaction (RT-PCR). RT-PCR is the most sensitive of these assays, and detects 10 genomes/ml. Serum HDAg or anti-HDV IgM or IgG are typically detected by enzyme-linked immunosorbant assay (ELISA) or radioimmunoassay (RIA), and HDAg can also be detected by immunofluorescence or immunohistochemical staining of liver biopsies. Since HBV infection is essential for HDV infection, the presence of the HBV surface antigen (HBsAg) usually precedes the detection of HDV.

Acute HDV co-infection (HDV/HBV) is characterized by high titers of IgM anti-HBc (antibodies against HBV core antigen), which are antibodies that disappear in chronic HBV infection. HDAg is also an early marker of acute HDV infection (both in the co-infection and superinfection setting). Anti-HD antibodies are later markers but can be used to establish the diagnosis if the early markers are no longer present, and are an indicator of progression to chronic infection. In chronic HDV infection, HDAg are complexed with anti-HD at high titer. At this stage, it is difficult to detect HDAg in the liver, but HDV RNA can typically be detected in the serum, and the high titer of anti-HD is the main biomarker used to diagnose chronic HDV infection.

HDV is considered to be eliminated when both HDV RNA in the serum and HDAg in the liver become persistently undetectable (Pascarella et al., supra), although only when accompanied by or followed by clearance of HBsAg (HBV surface antigen) is the cure considered to be definitive. It is believed that the development of anti-HD antibodies will protect against re-infection with HDV, and clearance of the virus is typically characterized by normalization of ALT levels, reduction in liver necro-inflammation, and halting of the progression of liver fibrosis.

One embodiment of the invention relates to a method to treat chronic hepatitis D virus (HDV) infection, and/or to prevent, ameliorate or treat at least one symptom of chronic HDV infection, in an individual or population of individuals. The method includes the step of administering to an individual or a population of individuals who are chronically infected with HDV one or more immunotherapeutic compositions of the invention. In one aspect, the composition is an immunotherapeutic composition comprising one or more HDV antigens as described herein, which can include one or more yeast-based immunotherapeutic compositions. In one aspect, the composition includes a protein or fusion protein comprising HDV antigens as described herein, and/or recombinant nucleic acid molecule encoding such protein or fusion protein. In one aspect, the individual or population of individuals is additionally treated with at least one other therapeutic compound useful for the treatment of HDV infection, such as a type I interferon (e.g., IFN-α).

In this embodiment of the invention, the subject to be treated, having chronic HDV infection, will also therefore be infected with hepatitis B virus (HBV). Accordingly, it is a further aspect of this method of the invention to concurrently or sequentially (before or after) treat the subject for the HBV infection. A variety of agents are known to be useful for preventing and/or treating or ameliorating HBV infection. Such agents include, but are not limited to, anti-viral compounds, including, but not limited to, nucleotide analogue reverse transcriptase inhibitor (nRTIs). In one aspect of the invention, suitable anti-viral compounds include, but are not limited to: tenofovir (VIREAD®), lamivudine (EPIVIR®), adefovir (HEPSERA®), telbivudine (TYZEKA®), entecavir (BARACLUDE®), and combinations thereof, and/or interferons, such as interferon-α2a or pegylated interferon-α2a (PEGASYS®) or interferon-λ. For the treatment of HBV, these agents are typically administered for long periods of time (e.g., daily or weekly for up to one to five years or longer).

In addition, other compositions for the treatment of HBV may be combined with the compositions of the invention for treating HDV, such as various prophylactic and/or immunotherapeutic compositions for HBV. Prophylactic vaccines for HBV have been commercially available since the early 1980's, and are non-infectious, subunit viral vaccines providing purified recombinant hepatitis B virus surface antigen (HBsAg), and can be administered beginning at birth. There are currently no approved therapeutic vaccines for HBV.

Another embodiment of the invention relates to a method to immunize an individual or population of individuals against HDV in order to prevent HDV infection, prevent chronic HDV infection, and/or reduce the severity of HDV infection in the individual or population of individuals. The method includes the step of administering to an individual or population of individuals that is not infected with HDV (or believed not to be infected with HDV), a composition of the invention. In one aspect, the composition is an immunotherapeutic composition comprising one or more HDV antigens as described herein, including one or more yeast-based immunotherapeutic compositions. In one aspect, the composition includes a fusion protein comprising HDV antigens as described herein, or recombinant nucleic acid molecule encoding such fusion protein.

In one aspect of this embodiment of the invention, the subject or population to be immunized against HDV infection using a composition of the invention is already chronically infected with HBV. In this aspect of the invention, the subject who is already chronically infected with HBV may be newly diagnosed, diagnosed but currently untreated for the HBV infection regardless of time since HBV diagnosis, or presently on treatment for chronic HBV infection, and can include subjects who have been on treatment for HBV infection for a long period of time (e.g., years). Such subjects can also include subjects who have been treated for HBV previously and are believed to be cured of the HBV infection at the present time. An HDV immunotherapeutic composition of the invention can also be used to immunize individuals or populations of individuals who may be at greater risk of becoming infected with HBV and HDV regardless of HBV infection status (e.g., these individuals may be immunized even if HBV-negative, or if the HBV status of the individual is not known), for example, due to location in an area of the world where HDV is endemic or highly prevalent. Individuals or populations of individuals who are at higher risk of exposure to HBV infection as compared to the general population (e.g., due to location, occupation, and/or high-risk practices associated with transmission of HBV) may also be immunized against HDV (concurrently), particularly if these individuals are located in an area where HDV is endemic or prevalent.

As used herein, the phrase "treat" HDV infection, or any permutation thereof (e.g., "treated for HDV infection", etc.) generally refers to applying or administering a composition of the invention once the infection (acute or chronic) has occurred, with the goal of reduction or elimination of detectable viral titer (e.g., reduction of viral RNA), reduction in at least one symptom resulting from the infection in the individual, delaying or preventing the onset and/or severity of symptoms and/or downstream sequela caused by the infection, reduction of organ or physiological system damage (e.g., cirrhosis) resulting from the infection (e.g., reduction of abnormal ALT levels, reduction of liver inflammation, reduction of liver fibrosis), prevention and/or reduction in the frequency and incidence of hepatocellular carcinoma (HCC), improvement in organ or system function that was negatively impacted by the infection (normalization of serum ALT levels, improvement in liver inflammation, improvement in liver fibrosis), improvement of immune responses against the infection, improvement of long term memory immune responses against the infection, reduced reactivation of HDV virus, improved general health of the individual or population of individuals, and/or improved overall survival of the individual or population of individuals. All such parameters are as compared to the status of the individual or population of individuals in the absence of the use of the HDV immunotherapeutic compositions of the invention.

In one aspect, a goal of treatment is sustained viral clearance for at least 6 months after the completion of therapy. In one aspect, a goal of treatment is the loss of detectable HDV RNA in the serum and HDAg in the liver, followed by clearance of HBsAg (HBV surface antigen), the latter of which may be achieved when the corresponding HBV infection is treated concurrently or sequentially with the HDV treatment described herein, such as by concurrent or sequential administration of anti-viral drugs for HBV, or other HBV therapies, including, but not limited to, interferons, HBV immunotherapy agents, or other therapeutic treatments for HBV. In one aspect, a goal of treatment is the development of antibodies (seroconversion) against the HDAg (anti-HD). Seroconversion may be determined by radioimmunoassay, enzyme immunoassay. Additional results of successful treatment of HDV infection include normalization of ALT levels, reduction in liver necro-inflammation, and halt of the progression of liver fibrosis.

To "prevent" HDV infection, or any permutation thereof (e.g., "prevention of HDV infection", etc.), generally refers to applying or administering a composition of the invention before an infection with HDV has occurred, with the goal of preventing infection by HDV, preventing chronic infection by HDV (i.e., enabling an individual to clear an acute HDV infection without further intervention), or at least reducing the severity, and/or length of infection and/or the physiological damage caused by the chronic infection, including by improving survival, in an individual or population of individuals should the infection later occur. In one aspect, the present invention can be used to prevent chronic HDV infection, such as by enabling an individual who becomes acutely infected with HDV subsequent to administration of a composition of the invention to clear the infection and not become chronically infected. In one aspect, the present invention is used to prevent or reduce the occurrence or severity of HDV infection in an individual chronically infected with HBV, even if the HBV infection is not itself cured.

The present invention includes the delivery (administration, immunization) of one or more immunotherapeutic compositions of the invention, including a yeast-based HDV immunotherapy composition, to a subject. The administration process can be performed ex vivo or in vivo, but is typically performed in vivo. Ex vivo administration refers to performing part of the regulatory step outside of the patient, such as administering a composition of the present invention to a population of cells (dendritic cells) removed from a patient under conditions such that a yeast vehicle, antigen(s) and any other agents or compositions are loaded into the cell, and returning the cells to the patient. The therapeutic composition of the present invention can be returned to a patient, or administered to a patient, by any suitable mode of administration.

Administration of a composition can be systemic, mucosal and/or proximal to the location of the target site (e.g., near a site of infection). Suitable routes of administration will be apparent to those of skill in the art, depending on the type of condition to be prevented or treated, the antigen used, and/or the target cell population or tissue. Various acceptable methods of administration include, but are not limited to, intravenous administration, intraperitoneal administration, intramuscular administration, intranodal administration, intracoronary administration, intraarterial administration (e.g., into a carotid artery), subcutaneous administration, transdermal delivery, intratracheal administration, intraarticular administration, intraventricular administration, inhalation (e.g., aerosol), intracranial, intraspinal, intraocular, aural, intranasal, oral, pulmonary administration, impregnation of a catheter, and direct injection into a tissue. In one aspect, routes of administration include: intravenous, intraperitoneal, subcutaneous, intradermal, intranodal, intramuscular, transdermal, inhaled, intranasal, oral, intraocular, intraarticular, intracranial, and intraspinal. Parenteral delivery can include intradermal, intramuscular, intraperitoneal, intrapleural, intrapulmonary, intravenous, subcutaneous, atrial catheter and venal catheter routes. Aural delivery can include ear drops, intranasal delivery can include nose drops or intranasal injection, and intraocular delivery can include eye drops. Aerosol (inhalation) delivery can also be performed using methods standard in the art (see, for example, Stribling et al., *Proc. Natl. Acad. Sci. USA* 189:11277-11281, 1992). Other routes of administration that modulate mucosal immunity may be useful in the treatment of viral infections. Such routes include bronchial, intradermal, intramuscular, intranasal, other inhalatory, rectal, subcutaneous, topical, transdermal, vaginal and urethral routes. In one aspect, an immunotherapeutic composition of the invention is administered subcutaneously.

With respect to the yeast-based immunotherapy compositions of the invention, in general, a suitable single dose is a dose that is capable of effectively providing a yeast vehicle and an antigen (if included) to a given cell type, tissue, or region of the patient body in an amount effective to elicit an antigen-specific immune response against one or more HDV antigens or epitopes, when administered one or more times over a suitable time period. For example, in one embodiment, a single dose of a yeast vehicle of the present invention is from about $1 \times 10^5$ to about $5 \times 10^7$ yeast cell equivalents per kilogram body weight of the organism being administered the composition. In one aspect, a single dose of a yeast vehicle of the present invention is from about 0.1 Y.U. ($1 \times 10^6$ cells) to about 100 Y.U. ($1 \times 10^9$ cells) per dose (i.e., per organism), including any interim dose, in increments of $0.1 \times 10^6$ cells (i.e., $1.1 \times 10^6$, $1.2 \times 10^6$, $1.3 \times 10^6$ . . . ). In one embodiment, doses include doses between 1 Y.U and 40 Y.U., doses between 1 Y.U. and 50 Y.U., doses between 1 Y.U. and 60 Y.U., doses between 1 Y.U. and 70 Y.U., or doses between 1 Y.U. and 80 Y.U., and in one aspect, between 10 Y.U. and 40 Y.U., 50 Y.U., 60 Y.U., 70 Y.U., or 80 Y.U. In one embodiment, the doses are administered at different sites on the individual but during the same dosing period. For example, a 40 Y.U. dose may be administered via by injecting 10 Y.U. doses to four different sites on the individual during one dosing period, or a 20 Y.U. dose may be administered by injecting 5 Y.U. doses to four different sites on the individual, or by injecting 10 Y.U. doses to two different sites on the individual, during the same dosing period. The invention includes administration of an amount of the yeast-based immunotherapy composition (e.g., 1, 2, 3, 4, 5, 6, 7, 8, 9 10, 11, 12, 13, 14, 15, 16, 17, 18, 19, 20 Y.U. or more) at 1, 2, 3, 4, 5, 6, 7, 8, 9, 10, or more different sites on an individual to form a single dose.

"Boosters" or "boosts" of a therapeutic composition are administered, for example, when the immune response against the antigen has waned or as needed to provide an immune response or induce a memory response against a particular antigen or antigen(s). Boosters can be administered from about 1, 2, 3, 4, 5, 6, 7, or 8 weeks apart, to monthly, to bimonthly, to quarterly, to annually, to several years after the original administration. In one embodiment, an administration schedule is one in which from about $1 \times 10^5$ to about $5 \times 10^7$ yeast cell equivalents of a composition per kg body weight of the organism is administered at least 1, 2, 3, 4, 5, 6, 7, 8, 9, 10, or more times over a time period of from weeks, to months, to years. In one embodiment, the doses are administered weekly for 1, 2, 3, 4, 5, 6, 7, 8, 9, 10 or more doses, followed by monthly doses as needed to achieve the desired inhibition or elimination of the HDV virus. For example, the doses can be administered until the individual achieves seroconversion, until HDV RNA titers are persistently undetectable, until HDAg is not detected in the liver, until HBV HBsAg is not detected, and/or until ALT levels normalize. In one embodiment, the doses are administered in a 4-weekly protocol (every 4 weeks, or on day 1, week 4, week 8, week 12, etc., for between 2 and 10 doses or longer as determined by the clinician). Additional doses can be administered even after the individual achieves seroconversion, if desired, although such dosing may not be necessary.

HDV immunotherapeutic compositions of the invention, including yeast-based HDV immunotherapeutic compositions, can be administered with one or more additional therapeutic or prophylactic agents. Such therapeutic or prophylactic agents can include agents that are useful for the prevention and/or treatment of HDV and can additionally include agents that are useful for the prevention and/or treatment of HBV. In one aspect of the invention, one or more additional therapeutic or prophylactic agents are administered sequentially with the yeast-based immunotherapy composition. In another embodiment, one or more additional therapeutic or prophylactic agents are administered before the yeast-based immunotherapy composition is administered. In another embodiment, one or more additional therapeutic or prophylactic agents are administered after the yeast-based HDV immunotherapy composition is administered. In one embodiment, one or more additional therapeutic or prophylactic agents are administered in alternating doses with the yeast-based immunotherapy composition, or in a protocol in which the yeast-based HDV composition is administered at prescribed intervals in between or with one or more consecutive doses of the additional agents, or vice versa. In one embodiment, the yeast-based HDV immunotherapy composition is administered in one or more doses over a period of time prior to commencing the administration of the additional agents. In other words, the yeast-based HDV immunotherapeutic composition is administered as a monotherapy for a period of time, and then the therapeutic or prophylactic agent administration is added, either concurrently with new doses of yeast-based HDV immunotherapy, or in an alternating fashion with yeast-based immunotherapy. Alternatively, the agent may be administered for a period of time prior to beginning administration of the yeast-based HDV immunotherapy composition.

In one embodiment of the invention, an additional therapeutic agent to be used in conjunction with a yeast-based HDV immunotherapeutic composition of the invention is an interferon. In one aspect, the interferon is interferon-α, and in one aspect, interferon-α2b (administered by subcutaneous injection 3 times per week); or pegylated interferon-α2a (e.g.) PEGASYS®. As used herein, the term "interferon" refers to a cytokine that is typically produced by cells of the immune system and by a wide variety of cells in response to the presence of double-stranded RNA. Interferons assist the immune response by inhibiting viral replication within host cells, activating natural killer cells and macrophages, increasing antigen presentation to lymphocytes, and inducing the resistance of host cells to viral infection. Type I interferons include interferon-α. Type III interferons include interferon-λ. Interferons useful in the methods of the present invention include any type I or type III interferon, including interferon-α, interferon-α2, and in one aspect, longer lasting forms of interferon, including, but not limited to, pegylated interferons, interferon fusion proteins (interferon fused to albumin), and controlled-release formulations comprising interferon (e.g., interferon in microspheres or interferon with polyaminoacid nanoparticles). One interferon, PEGASYS®, pegylated interferon-α2a, is a covalent conjugate of recombinant interferon-α2a (approximate molecular weight [MW] 20,000 daltons) with a single branched bis-monomethoxy polyethylene glycol (PEG) chain (approximate MW 40,000 daltons). The PEG moiety is linked at a single site to the interferon-α moiety via a stable amide bond to lysine. Pegylated interferon-α2a has an approximate molecular weight of 60,000 daltons.

For the treatment of HDV, interferon is typically administered by intramuscular or subcutaneous injection, and is usually administered at a high dose over a long period of time. In one embodiment, standard IFN-α is administered at about 9 million unites three times per week or 5 million units daily for 12 months, which may be extended if HBsAg is not cleared. Pegylated IFN-α can be administered weekly at a dose of between 3 and 10 million units, with 3 million units being preferred in one embodiment, and higher doses being preferred in other embodiments (e.g., 4 million units, 5 million units, 6 million units, 7 million units, 8 million units, 9 million units, or 10 million units. In general, doses of interferon are administered on a regular schedule, which can vary from 1, 2, 3, 4, 5, or 6 times a week, to weekly, biweekly, every three weeks, or monthly, and depend on the type of interferon administered, tolerance of the patient, and resolution of the infection. A typical dose of interferon that is currently available is provided weekly (pegylated IFN-α), and that is a preferred dosing schedule for interferon, according to the present invention.

In one aspect of the invention, when a treatment course of interferon therapy begins, additional doses of the immunotherapeutic composition of the invention are administered over the same period of time, or for at least a portion of that time, and may continue to be administered once the course of interferon has ended. However, the dosing schedule for the immunotherapy over the entire period may be, and is expected to typically be, different than that for the interferon. For example, the immunotherapeutic composition may be administered on the same days or at least 3-4 days after the last given (most recent) dose of interferon (or any suitable number of days after the last dose), and may be administered daily, weekly, biweekly, monthly, bimonthly, or every 3-6 months, or at longer intervals as determined by the physician. During an initial period of monotherapy, administration of the immunotherapeutic composition, if utilized, the immunotherapeutic composition is preferably administered weekly for between 4 and 12 weeks, followed by monthly administration (regardless of when the additional interferon is added into the protocol). In one aspect, the immunotherapeutic composition is administered weekly for four or five weeks, followed by monthly administration thereafter, until conclusion of the complete treatment protocol. In one aspect of the invention, the use of an HDV immunotherapeutic composition of the invention is used in an interferon-free protocol (i.e., as monotherapy or in combination with one or more agents that are not interferon).

In one aspect of the invention, an additional therapeutic agent to be administered in conjunction with a yeast-based HDV immunotherapeutic composition of the invention is an anti-viral compound that is effective for the treatment of the co-existing HBV infection in the subject. As used herein, the term "anti-viral" refers to any compound or drug, typically a small-molecule inhibitor or antibody, which targets one or more steps in the virus life cycle with direct anti-viral therapeutic effects. Suitable anti-viral compounds include, but are not limited to: tenofovir (VIREAD®), lamivudine (EPIVIR®), adefovir (HEPSERA®), telbivudine (TYZEKA®), entecavir (BARACLUDE®), and combinations thereof.

Tenofovir (tenofovir disoproxil fumarate or TDF), or ({[(2R)-1-(6-amino-9H-purin-9-yl)propan-2-yl]oxy}methyl)phosphonic acid, is a nucleotide analogue reverse transcriptase inhibitor (nRTIs). For the treatment of HBV infection, tenofovir is typically administered to adults as a pill taken at a dose of 300 mg (tenofovir disproxil fumarate) once daily. Dosage for pediatric patients is based on body weight of the patient (8 mg per kg body weight, up to 300 mg once daily) and may be provided as tablet or oral powder.

Lamivudine, or 2',3'-dideoxy-3'-thiacytidine, commonly called 3TC, is a potent nucleoside analog reverse transcriptase inhibitor (nRTI). For the treatment of HBV infection, lamivudine is administered as a pill or oral solution taken at a dose of 100 mg once a day (1.4-2 mg/lb. twice a day for children 3 months to 12 years old).

Adefovir (adefovir dipivoxil), or 9-[2-[[bis[(pivaloyloxy)methoxy]-phosphinyl]-methoxy]ethyl]adenine, is an orally-administered nucleotide analog reverse transcriptase inhibitor (ntRTI). For the treatment of HBV infection, adefovir is administered as a pill taken at a dose of 10 mg once daily.

Telbivudine, or 1-(2-deoxy-β-L-erythro-pentofuranosyl)-5-methylpyrimidine-2,4(1H,3H)-dione, is a synthetic thymidine nucleoside analogue (the L-isomer of thymidine). For the treatment of HBV infection, telbivudine is administered as a pill or oral solution taken at a dose of 600 mg once daily.

Entecavir, or 2-Amino-9-[(1S,3R,4S)-4-hydroxy-3-(hydroxymethyl)-2-methylidenecyclopentyl]-6,9-dihydro-3H-purin-6-one, is a nucleoside analog (guanine analogue) that inhibits reverse transcription, DNA replication and transcription of the virus. For the treatment of HBV infection, entecavir is administered as a pill or oral solution taken at a dose of 0.5 mg once daily (1 mg daily for lamivudine-refractory or telbivudine resistance mutations).

In aspects of the invention, an immunotherapeutic composition and other agents can be administered together (concurrently). As used herein, concurrent use does not necessarily mean that all doses of all compounds are administered on the same day at the same time. Rather, concurrent use means that each of the therapy components (e.g., immunotherapy and interferon therapy) are started at approximately the same period (within hours, up to 1-7 days of each other, or even longer (weeks or months apart) but administered as part of the same protocol) and are administered over the same general period of time, noting that each component may have a different dosing schedule (e.g., interferon weekly, immunotherapy monthly). In addition, before or after the concurrent administration period, any one of the agents or immunotherapeutic compositions can be administered without the other agent(s).

It is contemplated by the present invention that the use of an immunotherapeutic composition of the invention with an interferon such as IFN-α will enable a shorter time course for the use of the interferon, or may enable the elimination of the interferon. Dosing requirements for the interferon may also be reduced or modified as a result of combination with the immunotherapeutic of the invention to generally improve the tolerance of the patient for the drug. In addition, it is contemplated that the immunotherapeutic composition of the invention will enable seroconversion or sustained viral responses for patients in whom interferon therapy alone fails to achieve these endpoints. In other words, more patients will achieve viral negativity or seroconversion when an immunotherapeutic composition of the invention is combined with an interferon than will achieve viral negativity or seroconversion by using interferon alone.

In the method of the present invention, compositions and therapeutic compositions can be administered to animal, including any vertebrate, and particularly to any member of the Vertebrate class, Mammalia, including, without limitation, primates, rodents, livestock and domestic pets. Livestock include mammals to be consumed or that produce useful products (e.g., sheep for wool production). Mammals to treat or protect include humans, dogs, cats, mice, rats, goats, sheep, cattle, horses and pigs.

An "individual" is a vertebrate, such as a mammal, including without limitation a human. Mammals include, but are not limited to, farm animals, sport animals, pets, primates, mice and rats. The term "individual" can be used interchangeably with the term "animal", "subject" or "patient".

General Techniques Useful in the Invention

The practice of the present invention will employ, unless otherwise indicated, conventional techniques of molecular biology (including recombinant techniques), microbiology, cell biology, biochemistry, nucleic acid chemistry, and immunology, which are well known to those skilled in the art. Such techniques are explained fully in the literature, such as, *Methods of Enzymology*, Vol. 194, Guthrie et al., eds., Cold Spring Harbor Laboratory Press (1990); *Biology and activities of yeasts*, Skinner, et al., eds., Academic Press (1980); *Methods in yeast genetics: a laboratory course manual*, Rose et al., Cold Spring Harbor Laboratory Press (1990); *The Yeast Saccharomyces: Cell Cycle and Cell Biology*, Pringle et al., eds., Cold Spring Harbor Laboratory Press (1997); *The Yeast Saccharomyces: Gene Expression*, Jones et al., eds., Cold Spring Harbor Laboratory Press (1993); *The Yeast Saccharomyces: Genome Dynamics, Protein Synthesis, and Energetics*, Broach et al., eds., Cold Spring Harbor Laboratory Press (1992); *Molecular Cloning: A Laboratory Manual*, second edition (Sambrook et al., 1989) and *Molecular Cloning: A Laboratory Manual*, third edition (Sambrook and Russel, 2001), (jointly referred to herein as "Sambrook"); Current Protocols in Molecular Biology (F. M. Ausubel et al., eds., 1987, including supplements through 2001); *PCR: The Polymerase Chain Reaction*, (Mullis et al., eds., 1994); Harlow and Lane (1988), *Antibodies, A Laboratory Manual*, Cold Spring Harbor Publications, New York; Harlow and Lane (1999) *Using Antibodies: A Laboratory Manual*, Cold Spring Harbor Laboratory Press, Cold Spring Harbor, N.Y. (jointly referred to herein as "Harlow and Lane"), Beaucage et al. eds., *Current Protocols in Nucleic Acid Chemistry*, John Wiley & Sons, Inc., New York, 2000); Casarett and Doull's *Toxicology The Basic Science of Poisons*, C. Klaassen, ed., 6th edition (2001), and *Vaccines*, S. Plotkin and W. Orenstein, eds., 3rd edition (1999).

General Definitions

A "TARMOGEN®" (GlobeImmune, Inc., Louisville, Colo.) generally refers to a yeast vehicle expressing one or more heterologous antigens extracellularly (on its surface), intracellularly (internally or cytosolically) or both extracellularly and intracellularly. TARMOGEN® products have been generally described (see, e.g., U.S. Pat. No. 5,830,463). Certain yeast-based immunotherapy compositions, and methods of making and generally using the same, are also described in detail, for example, in U.S. Pat. No. 5,830,463, U.S. Pat. No. 7,083,787, U.S. Pat. No. 7,736,642, Stubbs et al., *Nat. Med.* 7:625-629 (2001), Lu et al., *Cancer Research* 64:5084-5088 (2004), and in Bernstein et al., *Vaccine* 2008 Jan. 24; 26(4):509-21, each of which is incorporated herein by reference in its entirety.

As used herein, the term "analog" refers to a chemical compound that is structurally similar to another compound but differs slightly in composition (as in the replacement of one atom by an atom of a different element or in the presence of a particular functional group, or the replacement of one functional group by another functional group). Thus, an analog is a compound that is similar or comparable in function and appearance, but has a different structure or origin with respect to the reference compound.

The terms "substituted", "substituted derivative" and "derivative", when used to describe a compound, means that at least one hydrogen bound to the unsubstituted compound is replaced with a different atom or a chemical moiety.

Although a derivative has a similar physical structure to the parent compound, the derivative may have different chemical and/or biological properties than the parent compound. Such properties can include, but are not limited to, increased or decreased activity of the parent compound, new activity as compared to the parent compound, enhanced or decreased bioavailability, enhanced or decreased efficacy, enhanced or decreased stability in vitro and/or in vivo, and/or enhanced or decreased absorption properties.

In general, the term "biologically active" indicates that a compound (including a protein or peptide) has at least one detectable activity that has an effect on the metabolic or other processes of a cell or organism, as measured or observed in vivo (i.e., in a natural physiological environment) or in vitro (i.e., under laboratory conditions).

According to the present invention, the term "modulate" can be used interchangeably with "regulate" and refers generally to upregulation or downregulation of a particular activity. As used herein, the term "upregulate" can be used generally to describe any of: elicitation, initiation, increasing, augmenting, boosting, improving, enhancing, amplifying, promoting, or providing, with respect to a particular activity. Similarly, the term "downregulate" can be used generally to describe any of: decreasing, reducing, inhibiting, ameliorating, diminishing, lessening, blocking, or preventing, with respect to a particular activity.

In one embodiment of the present invention, any of the amino acid sequences described herein can be produced with from at least one, and up to about 20, additional heterologous amino acids flanking each of the C- and/or N-terminal ends of the specified amino acid sequence. The resulting protein or polypeptide can be referred to as "consisting essentially of" the specified amino acid sequence. According to the present invention, the heterologous amino acids are a sequence of amino acids that are not naturally found (i.e., not found in nature, in vivo) flanking the specified amino acid sequence, or that are not related to the function of the specified amino acid sequence, or that would not be encoded by the nucleotides that flank the naturally occurring nucleic acid sequence encoding the specified amino acid sequence as it occurs in the gene, if such nucleotides in the naturally occurring sequence were translated using standard codon usage for the organism from which the given amino acid sequence is derived. Similarly, the phrase "consisting essentially of", when used with reference to a nucleic acid sequence herein, refers to a nucleic acid sequence encoding a specified amino acid sequence that can be flanked by from at least one, and up to as many as about 60, additional heterologous nucleotides at each of the 5' and/or the 3' end of the nucleic acid sequence encoding the specified amino acid sequence. The heterologous nucleotides are not naturally found (i.e., not found in nature, in vivo) flanking the nucleic acid sequence encoding the specified amino acid sequence as it occurs in the natural gene or do not encode a protein that imparts any additional function to the protein or changes the function of the protein having the specified amino acid sequence.

According to the present invention, the phrase "selectively binds to" refers to the ability of an antibody, antigen-binding fragment or binding partner of the present invention to preferentially bind to specified proteins. More specifically, the phrase "selectively binds" refers to the specific binding of one protein to another (e.g., an antibody, fragment thereof, or binding partner to an antigen), wherein the level of binding, as measured by any standard assay (e.g., an immunoassay), is statistically significantly higher than the background control for the assay. For example, when performing an immunoassay, controls typically include a reaction well/tube that contain antibody or antigen binding fragment alone (i.e., in the absence of antigen), wherein an amount of reactivity (e.g., non-specific binding to the well) by the antibody or antigen-binding fragment thereof in the absence of the antigen is considered to be background. Binding can be measured using a variety of methods standard in the art including enzyme immunoassays (e.g., ELISA, immunoblot assays, etc.).

Reference to a protein or polypeptide used in the present invention includes full-length proteins, fusion proteins, or any fragment, domain, conformational epitope, or homologue of such proteins, including functional domains and immunological domains of proteins. More specifically, an isolated protein, according to the present invention, is a protein (including a polypeptide or peptide) that has been removed from its natural milieu (i.e., that has been subject to human manipulation) and can include purified proteins, partially purified proteins, recombinantly produced proteins, and synthetically produced proteins, for example. As such, "isolated" does not reflect the extent to which the protein has been purified. Preferably, an isolated protein of the present invention is produced recombinantly. According to the present invention, the terms "modification" and "mutation" can be used interchangeably, particularly with regard to the modifications/mutations to the amino acid sequence of proteins or portions thereof (or nucleic acid sequences) described herein.

As used herein, the term "homologue" is used to refer to a protein or peptide which differs from a naturally occurring protein or peptide (i.e., the "prototype" or "wild-type" protein) by minor modifications to the naturally occurring protein or peptide, but which maintains the basic protein and side chain structure of the naturally occurring form. Such changes include, but are not limited to: changes in one or a few amino acid side chains; changes one or a few amino acids, including deletions (e.g., a truncated version of the protein or peptide) insertions and/or substitutions; changes in stereochemistry of one or a few atoms; and/or minor derivatizations, including but not limited to: methylation, glycosylation, phosphorylation, acetylation, myristoylation, prenylation, palmitation, amidation and/or addition of glycosylphosphatidyl inositol. A homologue can have enhanced, decreased, or substantially similar properties as compared to the naturally occurring protein or peptide. A homologue can include an agonist of a protein or an antagonist of a protein. Homologues can be produced using techniques known in the art for the production of proteins including, but not limited to, direct modifications to the isolated, naturally occurring protein, direct protein synthesis, or modifications to the nucleic acid sequence encoding the protein using, for example, classic or recombinant DNA techniques to effect random or targeted mutagenesis.

A homologue of a given protein may comprise, consist essentially of, or consist of, an amino acid sequence that is at least about 45%, or at least about 50%, or at least about 55%, or at least about 60%, or at least about 65%, or at least about 70%, or at least about 75%, or at least about 80%, or at least about 85%, or at least about 90%, or at least about 91% identical, or at least about 92% identical, or at least about 93% identical, or at least about 94% identical, or at least about 95% identical, or at least about 96% identical, or at least about 97% identical, or at least about 98% identical, or at least about 99% identical (or any percent identity between 45% and 99%, in whole integer increments), to the amino acid sequence of the reference protein. In one embodiment, the homologue comprises, consists essentially of, or consists of, an amino acid sequence that is less than 100% identical, less than about 99% identical, less than about 98% identical, less than about 97% identical, less than about 96% identical, less than about 95% identical, and so on, in increments of 1%, to less than about 70% identical to the naturally occurring amino acid sequence of the reference protein.

A homologue may include proteins or domains of proteins that are "near full-length", which means that such a homologue differs from the full-length protein, functional domain or immunological domain (as such protein, functional domain or immunological domain is described herein or otherwise known or described in a publicly available sequence) by the addition of or deletion of 1, 2, 3, 4, 5, 6, 7, 8, 9, or 10 amino acids from the N- and/or the C-terminus of such full-length protein or full-length functional domain or full-length immunological domain.

As used herein, unless otherwise specified, reference to a percent (%) identity refers to an evaluation of homology which is performed using: (1) a BLAST 2.0 Basic BLAST homology search using blastp for amino acid searches and blastn for nucleic acid searches with standard default parameters, wherein the query sequence is filtered for low complexity regions by default (described in Altschul, S. F., Madden, T. L., Schäffer, A. A., Zhang, J., Zhang, Z., Miller, W. & Lipman, D. J. (1997) "Gapped BLAST and PSI-BLAST: a new generation of protein database search programs." Nucleic Acids Res. 25:3389-3402, incorporated herein by reference in its entirety); (2) a BLAST 2 alignment (using the parameters described below); (3) and/or PSI-BLAST with the standard default parameters (Position-Specific Iterated BLAST. It is noted that due to some differences in the standard parameters between BLAST 2.0 Basic BLAST and BLAST 2, two specific sequences might be recognized as having significant homology using the BLAST 2 program, whereas a search performed in BLAST 2.0 Basic BLAST using one of the sequences as the query sequence may not identify the second sequence in the top matches. In addition, PSI-BLAST provides an automated, easy-to-use version of a "profile" search, which is a sensitive way to look for sequence homologues. The program first performs a gapped BLAST database search. The PSI-BLAST program uses the information from any significant alignments returned to construct a position-specific score matrix, which replaces the query sequence for the next round of database searching. Therefore, it is to be understood that percent identity can be determined by using any one of these programs.

Two specific sequences can be aligned to one another using BLAST 2 sequence as described in Tatusova and Madden, (1999), "Blast 2 sequences—a new tool for comparing protein and nucleotide sequences", FEMS Microbiol Lett. 174:247-250, incorporated herein by reference in its entirety. BLAST 2 sequence alignment is performed in blastp or blastn using the BLAST 2.0 algorithm to perform a Gapped BLAST search (BLAST 2.0) between the two sequences allowing for the introduction of gaps (deletions and insertions) in the resulting alignment. For purposes of clarity herein, a BLAST 2 sequence alignment is performed using the standard default parameters as follows.

For blastn, using 0 BLOSUM62 matrix:
Reward for match=1
Penalty for mismatch=−2
Open gap (5) and extension gap (2) penalties
gap x_dropoff (50) expect (10) word size (11) filter (on)
For blastp, using 0 BLOSUM62 matrix:
Open gap (11) and extension gap (1) penalties
gap x_dropoff (50) expect (10) word size (3) filter (on).

An isolated nucleic acid molecule is a nucleic acid molecule that has been removed from its natural milieu (i.e., that has been subject to human manipulation), its natural milieu being the genome or chromosome in which the nucleic acid molecule is found in nature. As such, "isolated" does not necessarily reflect the extent to which the nucleic acid molecule has been purified, but indicates that the molecule does not include an entire genome or an entire chromosome in which the nucleic acid molecule is found in nature. An isolated nucleic acid molecule can include a gene. An isolated nucleic acid molecule that includes a gene is not a fragment of a chromosome that includes such gene, but rather includes the coding region and regulatory regions associated with the gene, but no additional genes that are naturally found on the same chromosome. An isolated nucleic acid molecule can also include a specified nucleic acid sequence flanked by (i.e., at the 5' and/or the 3' end of the sequence) additional nucleic acids that do not normally flank the specified nucleic acid sequence in nature (i.e., heterologous sequences). Isolated nucleic acid molecule can include DNA, RNA (e.g., mRNA), or derivatives of either DNA or RNA (e.g., cDNA). Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding a protein or domain of a protein.

A recombinant nucleic acid molecule is a molecule that can include at least one of any nucleic acid sequence encoding any one or more proteins described herein operatively linked to at least one of any transcription control sequence capable of effectively regulating expression of the nucleic acid molecule(s) in the cell to be transfected. Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding a protein. In addition, the phrase "recombinant molecule" primarily refers to a nucleic acid molecule operatively linked to a transcription control sequence, but can be used interchangeably with the phrase "nucleic acid molecule" which is administered to an animal.

A recombinant nucleic acid molecule includes a recombinant vector, which is any nucleic acid sequence, typically a heterologous sequence, which is operatively linked to the isolated nucleic acid molecule encoding a fusion protein of the present invention, which is capable of enabling recombinant production of the fusion protein, and which is capable of delivering the nucleic acid molecule into a host cell according to the present invention. Such a vector can contain nucleic acid sequences that are not naturally found adjacent to the isolated nucleic acid molecules to be inserted into the vector. The vector can be either RNA or DNA, either prokaryotic or eukaryotic, and preferably in the present invention, is a virus or a plasmid. Recombinant vectors can be used in the cloning, sequencing, and/or otherwise manipulating of nucleic acid molecules, and can be used in delivery of such molecules (e.g., as in a DNA composition or a viral vector-based composition). Recombinant vectors are preferably used in the expression of nucleic acid molecules, and can also be referred to as expression vectors. Preferred recombinant vectors are capable of being expressed in a transfected host cell.

In a recombinant molecule of the present invention, nucleic acid molecules are operatively linked to expression vectors containing regulatory sequences such as transcription control sequences, translation control sequences, origins of replication, and other regulatory sequences that are compatible with the host cell and that control the expression of nucleic acid molecules of the present invention. In particular, recombinant molecules of the present invention include nucleic acid molecules that are operatively linked to one or more expression control sequences. The phrase "operatively linked" refers to linking a nucleic acid molecule to an expression control sequence in a manner such that the molecule is expressed when transfected (i.e., transformed, transduced or transfected) into a host cell.

According to the present invention, the term "transfection" is used to refer to any method by which an exogenous nucleic acid molecule (i.e., a recombinant nucleic acid molecule) can be inserted into a cell. The term "transformation" can be used interchangeably with the term "transfection" when such term is used to refer to the introduction of nucleic acid molecules into microbial cells, such as algae, bacteria and yeast. In microbial systems, the term "transformation" is used to describe an inherited change due to the acquisition of exogenous nucleic acids by the microorganism and is essentially synonymous with the term "transfection." Therefore, transfection techniques include, but are not limited to, transformation, chemical treatment of cells, particle bombardment, electroporation, microinjection, lipofection, adsorption, infection and protoplast fusion.

The following experimental results are provided for purposes of illustration and are not intended to limit the scope of the invention.

EXAMPLES

Example 1

The following example describes the production of a yeast-based immunotherapeutic composition for the treatment or prevention of hepatitis D virus (HDV) infection.

In this experiment, yeast (e.g., *Saccharomyces cerevisiae*) were engineered to express an HDV antigen under the control of the copper-inducible promoter, CUP1. The HDV antigen was a single polypeptide of approximately 218 amino acids, with the following sequence elements fused in frame from N- to C-terminus, represented by SEQ ID NO:30: (1) an N-terminal peptide to impart resistance to proteasomal degradation and stabilize expression (positions 1 to 6 of SEQ ID NO:30); 2) a two amino acid spacer (Thr-Ser) to introduce a SpeI restriction enzyme site (positions 7 to 8 of SEQ ID NO:30); 3) the amino acid sequence of a HDV genotype 1 large (L) antigen (HDAg-L) that was modified to delete the nuclear localization sequence (positions 9 to 212 of SEQ ID NO:30, also represented herein by SEQ ID NO:28); and 4) a hexahistidine tag (positions 213 to 218 of SEQ ID NO:30). A nucleic acid sequence encoding the fusion protein of SEQ ID NO:30 (codon optimized for yeast expression) is represented herein by SEQ ID NO:29. SEQ ID NO:30 (and SEQ ID NO:28) contains multiple epitopes or domains that are believed to enhance the immunogenicity of the HDV antigen. For example, positions 34 to 42 and positions 51 to 59 of SEQ ID NO:30, comprise known MHC Class I T cell epitopes, and positions 34 to 49, positions 58 to 73, positions 74 to 87, positions 104 to 119, and positions 120-151 comprise known MHC Class II T cell epitopes. A yeast immunotherapy composition expressing SEQ ID NO:30 is also referred to herein as HDV1.

A second product expressing the same HDV antigen as above, but with the NLS retained, was produced as follows. Yeast (e.g., *Saccharomyces cerevisiae*) were engineered to express the HDV antigen under the control of the copper-inducible promoter, CUP1. The HDV antigen was a single polypeptide of approximately 228 amino acids, with the following sequence elements fused in frame from N- to C-terminus, represented by SEQ ID NO:33: (1) an N-terminal peptide to impart resistance to proteasomal degradation and stabilize expression (positions 1 to 6 of SEQ ID NO:33); 2) a two amino acid spacer (Thr-Ser) to introduce a SpeI restriction enzyme site (positions 7 to 8 of SEQ ID NO:33); 3) the amino acid sequence of a HDV genotype 1 large (L) antigen (HDAg-L) corresponding to SEQ ID NO:2 except for the substitution of an alanine in place of the glutamine at position 66 of SEQ ID NO:2 (positions 9 to 222 of SEQ ID NO:33, also represented herein by SEQ ID NO:31); and 4) a hexahistidine tag (positions 223 to 228 of SEQ ID NO:33). A nucleic acid sequence encoding the fusion protein of SEQ ID NO:33 (codon optimized for yeast expression) is represented herein by SEQ ID NO:32. SEQ ID NO:33 (and SEQ ID NO:31) contains multiple epitopes or domains that are believed to enhance the immunogenicity of the HDV antigen. For example, positions 34 to 42 and positions 51 to 59 of SEQ ID NO:33, comprise known MHC Class I T cell epitopes, and positions 34 to 49, positions 58 to 73, positions 74 to 89, positions 82 to 97, positions 114 to 129 and positions 130 to 161 comprise known MHC Class II T cell epitopes. A yeast immunotherapy composition expressing SEQ ID NO:33 is also referred to herein as HDV2.

Figure 4:
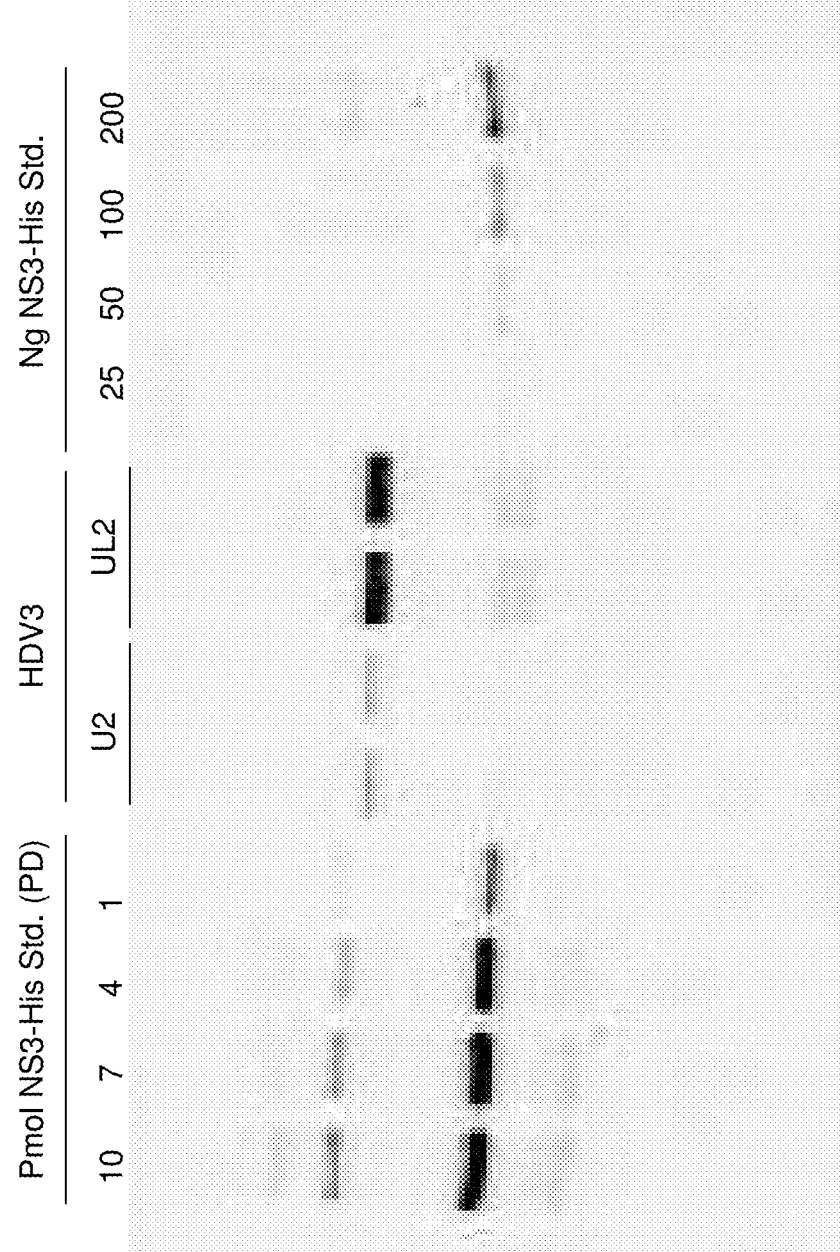
FIG. 4 is a digitized image showing expression of the yeast-based immunotherapeutic known as HDV3 (expressing SEQ ID NO:36) grown in U2 and UL2 medium.

To produce the HDV1 and HDV2 yeast immunotherapy compositions, briefly, DNA encoding the HDV antigens described above was codon optimized for expression in yeast, and then digested with EcoRI and NotI and inserted behind the CUP1 promoter (pGI-100) in yeast 2 µm expression vectors. The nucleotide sequence of SEQ ID NO:29 encodes the fusion protein represented by SEQ ID NO:30, and the nucleotide sequence of SEQ ID NO:32 encodes the fusion protein represented by SEQ ID NO:33. The resulting plasmids were introduced into *Saccharomyces cerevisiae* W303α yeast by Lithium acetate/polyethylene glycol transfection, and primary transfectants were selected on solid minimal plates lacking uracil (UDM; uridine dropout medium). Colonies were re-streaked onto UDM or ULDM (uridine and leucine dropout medium) and allowed to grow for 3 days at 30° C. Liquid cultures lacking uridine (U2 medium: 20 g/L glucose; 6.7 g/L of yeast nitrogen base containing ammonium sulfate; 0.04 mg/mL each of histidine, leucine, tryptophan, and adenine) or lacking uridine and leucine (UL2 medium: 20 g/L glucose; 6.7 g/L of yeast nitrogen base containing ammonium sulfate; and 0.04 mg/mL each of histidine, tryptophan, and adenine) were inoculated from plates and starter cultures were grown for 20 h at 30° C., 250 rpm. Primary cultures were used to inoculate final cultures of the same formulation and growth was continued until a density or 1.1 to 4.0 YU/mL was reached. Cultures were induced with 400 μM copper sulfate at this starting density of 1-4 YU/ml for 3 hours at 30° C. The cells from each culture were then harvested, PBS-washed and heat-killed at 56° C. for 1 hour in PBS.

After heat-kill of the cultures, the cells were thrice washed in PBS and total protein was isolated by glass bead rupture followed by boiling in SDS lysis buffer. Quantification of total protein was done by amidoschwarz/nitrocellulose binding assay, and HDV antigen content was measured by Western blot using an anti-His tag monoclonal antibody probe followed by interpolation to a His-tagged HCV NS3 protein standard curve.

Results are shown in FIGS. 2 and 3. FIG. 2 shows copper inducible expression of HDV1 and HDV2: U2 vs. UL2 using one set of internal standards (HDV1 and HDV2 loaded at 4 μg protein/lane), and FIG. 3 shows copper inducible expression of HDV1 and HDV2: U2 vs. UL2 using a second set of internal standards (HDV1 and HDV2 loaded at 4 μg protein/lane). These figures show that each of the HDV yeast-based immunotherapy compositions of the invention described above expresses the HDV protein, and can be identified by Western blot. Antigen expression was best using UL2 medium. The calculated antigen expression was ~7171 ng protein per Y.U. for the yeast expressing SEQ ID NO:30 (HDV1) and ~6600 ng protein per Y.U. for the yeast expressing SEQ ID NO:33 (HDV2) (Yeast Unit; One Yeast Unit (Y.U.) is $1\times10^7$ yeast cells or yeast cell equivalents) or 76 pmol protein per Y.U.). However, it was observed that HDV2 clumps and has a much longer doubling time than HDV1. Cell clumping and extremely slow growth are undesirable features for yeast-based immunotherapy candidates and, accordingly, HDV1 was selected for additional experiments.

Example 2

The following example describes the production of another yeast-based immunotherapeutic composition for the treatment or prevention of hepatitis D virus (HDV) infection.

In this experiment, yeast (e.g., *Saccharomyces cerevisiae*) were engineered to express an HDV antigen under the control of the copper-inducible promoter, CUP1. The HDV antigen was a single polypeptide of approximately 422 amino acids, with the following sequence elements fused in frame from N- to C-terminus, represented by SEQ ID NO:36: (1) an N-terminal peptide to impart resistance to proteasomal degradation and stabilize expression (positions 1 to 6 of SEQ ID NO:36); 2) a two amino acid spacer (Thr-Ser) to introduce a SpeI restriction enzyme site (positions 7 to 8 of SEQ ID NO:36); 3) the amino acid sequence of a HDV genotype 1 large (L) antigen (HDAg-L) that was modified to delete the nuclear localization sequence (positions 9 to 212 of SEQ ID NO:36); 4) the amino acid sequence of a HDV genotype 2 large (L) antigen (HDAg-L) that was modified to delete the nuclear localization sequence (positions 213 to 416 of SEQ ID NO:36); and 5) a hexahistidine tag (positions 417 to 422 of SEQ ID NO:36). An amino acid sequence representing only the HDV sequences in this fusion protein is SEQ ID NO:34. A nucleic acid sequence encoding the fusion protein of SEQ ID NO:36 (codon optimized for yeast expression) is represented herein by SEQ ID NO:35. SEQ ID NO:36 (and SEQ ID NO:34) contains multiple epitopes or domains that are believed to enhance the immunogenicity of the HDV antigen. For example, within the sequence from the HDV genotype 1 antigen positions 34 to 42 and positions 51 to 59 of SEQ ID NO:36, comprise known MHC Class I T cell epitopes, and positions 34 to 49, positions 58 to 73, positions 74 to 89, positions 82 to 97, positions 114 to 129 and positions 130 to 161 comprise known MHC Class II T cell epitopes. Corresponding sequences can be identified in the sequence from the HDV genotype 2 antigen. A yeast immunotherapy composition expressing SEQ ID NO:36 is also referred to herein as HDV3.

To produce the HDV3 yeast immunotherapeutic composition, briefly, DNA encoding the HDV antigen described above was codon optimized for expression in yeast, and then digested with EcoRI and NotI and inserted behind the CUP1 promoter (pGI-100) in yeast 2 μm expression vectors. The nucleotide sequence of SEQ ID NO:35 encodes the fusion protein represented by SEQ ID NO:36. The resulting plasmids were introduced into *Saccharomyces cerevisiae* W303α yeast by Lithium acetate/polyethylene glycol transfection, and primary transfectants were selected on solid minimal plates lacking uracil (UDM; uridine dropout medium). Colonies were re-streaked onto UDM or ULDM (uridine and leucine dropout medium) and allowed to grow for 3 days at 30° C. Liquid cultures lacking uridine (U2 medium: 20 g/L glucose; 6.7 g/L of yeast nitrogen base containing ammonium sulfate; 0.04 mg/mL each of histidine, leucine, tryptophan, and adenine) or lacking uridine and leucine (UL2 medium: 20 g/L glucose; 6.7 g/L of yeast nitrogen base containing ammonium sulfate; and 0.04 mg/mL each of histidine, tryptophan, and adenine) were inoculated from plates and starter cultures were grown for 20 h at 30° C., 250 rpm. Primary cultures were used to inoculate final cultures of the same formulation and growth was continued until a density or 1.1 to 4.0 YU/mL was reached. Cultures were induced with 400 μM copper sulfate at this starting density of 1-4 YU/ml for 3 hours at 30° C. The cells from each culture were then harvested, PBS-washed and heat-killed at 56° C. for 1 hour in PBS.

After heat-kill of the cultures, the cells were thrice washed in PBS and total protein was isolated by glass bead rupture followed by boiling in SDS lysis buffer. Quantification of total protein was done by amidoschwarz/nitrocellulose binding assay, and HDV antigen content was measured by Western blot using an anti-His tag monoclonal antibody probe followed by interpolation to a His-tagged HCV NS3 protein standard curve. Results are shown in FIG. 4. FIG. 4 shows copper inducible expression of HDV3 in each of U2 vs. UL2 medium using two different sets of internal standards. The results show that HDV3 expresses high levels of the HDV antigen, and can be identified by Western blot. Antigen expression was best using UL2 medium. The calculated antigen expression was ~23861 ng protein per Y.U. for the yeast expressing SEQ ID NO:36 (HDV3). HDV3 was selected for additional experimentation.

Example 3

The following example describes preclinical experiments in mice to demonstrate the immunogenicity of yeast-based HDV immunotherapy compositions of the invention when administered in vivo.

In these experiments, three groups of C57BL/6 mice were subcutaneously immunized as in Table 1. Mice were immunized with HDV1 (SEQ ID NO:30, see Example 1) and HDV3 (SEQ ID NO:36, see Example 2), and with a control yeast composition known as OVAX2010 (this yeast expresses chicken ovalbumin comprising an N-terminal alpha factor leader peptide, expression driven by the CUP1 promoter).

TABLE 2

Immunization Groups: C57BL/6 Mice

| Group | Mice | Vaccine | Regimen (once per week for 3 weeks) |
|---|---|---|---|
| A | C57BL/6 n = 5 | OVAX2010 | 2.5 YU scruff, 2.5 YU flank |
| B | C57BL/6 n = 5 | HDV1 | 2.5 YU scruff, 2.5 YU flank |
| C | C57BL/6 n = 5 | HDV3 | 2.5 YU scruff, 2.5 YU flank |

Mice were immunized with a total of 5 Y.U. (in two locations at 2.5 Y.U. per injection site) of the indicated yeast-based immunotherapy composition once per week for 3 weeks total. Eight days after the third immunization, mice were euthanized and spleen and lymph nodes were removed, macerated to single cell suspensions, and counted. Cells were placed into U-bottom 96-well plates at 200,000 cells/well ($10^6$ cells/mL), and HDV-specific peptide antigens were added at 30 μg/mL. After a 4 day incubation in a 37° C./5% $CO_2$ humidified incubator, 150 μl (150,000 cells) was transferred to dual interleukin-2/interferon-γ (IL-2/IFNγ) ELISpot plates (R&D Systems) for 24 hours. Plates were developed per the manufacturer's instructions and spots were counted using validated spot counting instrumentation and software (CTL, Inc.). The HDV peptides used in this assay were:

HDV 26-34 (HLA-A2 binder): KLEDLERDL; SEQ ID NO:20

HDV 43-51 (HLA-A2 binder): KLEDENPWL; SEQ ID NO:19

Figure 5A:
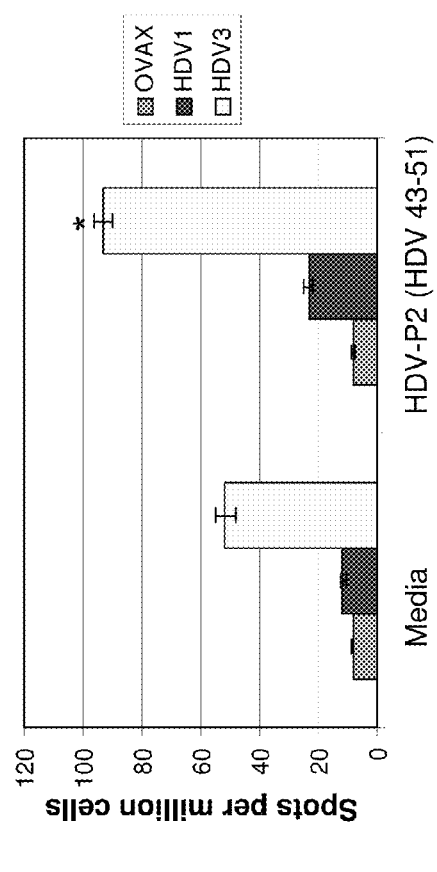
FIG. 5A is a graph showing an interferon-γ (IFNγ) ELISpot of yeast-based HDV immunotherapeutic compositions HDV1- and HDV3-vaccinated C57BL/6 mice using HDV-P2 peptide (OVAX=control yeast expressing irrelevant antigen).
Figure 5B:
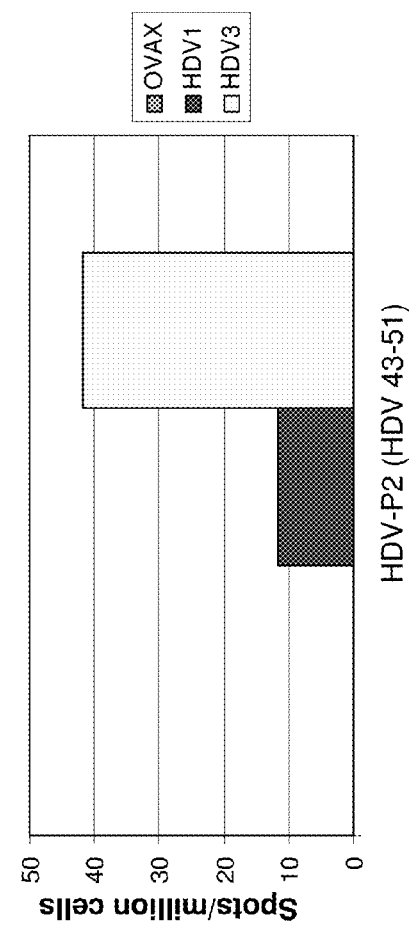
FIG. 5B is a graph showing the same ELISpot results as in FIG. 5A, with the medium background subtracted.

The results of this experiment are shown in FIGS. 5A, 5B, 6A and 6B. FIG. 5A shows that vaccination with HDV1 or HDV3 elicits an HDV-specific IFNγ ELISpot response that is specifically developed by the ex vivo addition of a known HDV T cell epitope peptide (P2: HDV 43-51 or SEQ ID NO:19; p=0.0008 HDV3 vs. OVAX). This result is meaningful because IFNγ is a key component of a functional adaptive immune response; it is produced by $CD4^+$ Th1 and $CD8^+$ cytotoxic T lymphocyte (CTL) effector T cells in the development of functional immunity. Although there was a notable level of background ELISpots in wells containing only growth medium, the antigen specificity of the immune response is clear even after subtraction of this background from the peptide-treated ELISpot counts (FIG. 5B). Notably, HDV3 elicited a 3.5-fold higher ELISpot response than HDV1 (FIG. 5B; 42 spots for HDV3 vs. 12 spots for HDV1) and contains a ~3.3-fold higher HDV antigen content than HDV1 (23861 Ng/YU for HDV3 vs. 7171 Ng/YU for HDV1). This finding illustrates that higher antigen content per yeast cell correlates with a greater frequency of antigen-specific T cells elicited by the yeast immunotherapy.

The results of the IL-2 ELISpot assay also revealed the induction of an antigen-specific immune response to HDV-1 vaccination. FIG. 6A shows that vaccination with HDV1 elicits an IL-2 ELISpot response that is specifically developed by ex vivo addition of a different HDV peptide (P1: HDV-26-34 or SEQ ID NO:20; p=0.02 HDV1 vs. OVAX). This result attests to the quality of the immune response induced by the yeast-HDV immunotherapeutic vaccination because IL-2 stimulates the growth, differentiation and survival of antigen-specific cytotoxic T cells. Although there is a notable level of background IL-2 ELISpots for samples incubated with growth medium only ("No stim" in FIG. 6A), the antigen specificity of the immune response is clear even after subtraction of this background from the peptide treated ELISpot counts (FIG. 6B). The number of background-corrected IL-2 ELISpots for HDV1-vaccinated mice is double that of OVAX-vaccinated mice.

Taken together, the IFNγ and IL-2 ELISpot data show that the HDV yeast-based immunotherapeutic compositions of the invention elicit antigen-specific T cells as a result of in vivo administration, producing cytokines that are known markers of CTL induction, and illustrating the utility of these compositions for the induction of functional anti-HDV responses.

Example 4

The following example describes a phase 1 clinical trial in healthy volunteers.

A 12-week, open-label dose escalation phase 1 clinical study is performed using a yeast-based HDV immunotherapy composition described herein (e.g., the HDV immunotherapy composition described in Examples 1 or 2). Subjects are immune active and healthy volunteers with no prior or current indication or record of HDV infection or HBV infection.

Approximately 48 subjects (6 arms, 8 subjects per arm) meeting these criteria are administered the yeast-based HDV immunotherapy composition in a sequential dose cohort escalation protocol utilizing one of two different dosing protocols as follows:

Protocol A: Prime-Boost Dosing (4 Weekly Doses Starting at Day 1, Followed by 2 Monthly Doses at Week 4 & Week 8)

Arm 1A: 20 Yeast Units (Y.U.) (administered in 10 Y.U. doses to 2 different sites);

Arm 2A: 40 Y.U. (administered in 10 Y.U. doses to 4 different sites);

Arm 3A: 80 Y.U. (administered in 20 Y.U. doses to 4 different sites)

4-Weekly Dosing (Three Total Doses Administered at Day 1, Week 4 and Week 8)

Arm 1B: 20 Y.U. (administered in 10 Y.U. doses to 2 different sites);
Arm 2B: 40 Y.U. (administered in 10 Y.U. doses to 4 different sites);
Arm 3B: 80 Y.U. (administered in 20 Y.U. doses to 4 different sites)

All doses are administered subcutaneously and the dose is divided among two or four sites on the body (every visit) as indicated above. Safety and immunogenicity (e.g., antigen-specific T cell responses measured by ELISpot and T cell proliferation) are assessed. Specifically, an ELISpot-based algorithm is developed for categorical responders. ELISpot assays measuring regulatory T cells (Treg) are also assessed and CD4$^+$ T cell proliferation in response to HDV antigens is assessed and correlated with the development of anti-*Saccharomyces cerevisiae* antibodies (ASCA).

It is expected that the yeast-based HDV immunotherapeutic will be well-tolerated and show immunogenicity as measured by one or more of ELISpot assay, lymphocyte proliferation assay (LPA), ex vivo T cell stimulation by HBV antigens, and/or ASCA.

Example 5

The following example describes a phase 1b/2a clinical trial in subjects chronically infected with both hepatitis D virus and hepatitis B virus (therapeutic arm), or mono-infected with hepatitis B virus (prophylactic arm).

An open-label dose escalation phase 1b/2a clinical trial is run using a yeast-based HDV immunotherapy composition described herein (e.g., the HDV immunotherapy composition described in Examples 1 or 2). In Arm 1 (HDV therapeutic treatment arm), subjects are immune active and chronically infected with both hepatitis B virus (HBV) and hepatitis D virus (HDV). In Arm 2 (HDV prophylaxis arm), subjects are immune active and chronically infected with HBV with no evidence of co-infection with HDV (i.e., HBV mono-infection). In each arm, the chronic HBV infection is well controlled by conventional HBV anti-viral therapy (e.g., tenofovir disoproxil fumarate, or TDF (VIREAD®)) as measured by HBV DNA levels.

In stage one of this study, subjects in both arms meeting the relevant criteria are administered the yeast-based HDV immunotherapy composition in a sequential dose cohort escalation protocol utilizing dose ranges from 0.05 Y.U. to 80 Y.U. Optionally, a single patient cohort will receive subcutaneous injections of placebo (PBS) on the same schedule as the immunotherapy plus continued anti-viral therapy. Conservative stopping rules are in place for ALT flares and signs of decompression.

In the second stage of each arm of this trial, subjects are randomized into equal numbered cohorts to continue on anti-viral alone or anti-viral plus the yeast-based HDV immunotherapeutic protocol (dose 1 and dose 2) for up to 48 weeks. Patients in Arm 2 may be optionally followed for a longer term (beyond 48 weeks) to monitor HDV infection rates. In Arm 2, a single patient cohort will receive subcutaneous injections of placebo (PBS) on the same schedule as the HDV immunotherapy, plus continued anti-viral therapy for HBV.

In Arm 1, safety, HDV viral kinetics, HDAg seroconversion, and HDV-specific immunogenicity (e.g., antigen-specific T cell responses measured by ELISpot) are assessed, as well as HBsAg seroconversion to measure effects of HBV treatment concurrently. In addition, dose-dependent biochemical (ALT) is monitored.

In Arm 2, safety and HDV-specific immunogenicity (e.g., antigen-specific T cell responses measured by ELISpot) are assessed, as well as HBsAg seroconversion concurrently, and subjects are routinely monitored for indicators of HDV infection, including by detection of HDV RNA, detection of the HDV antigen (HDAg), and/or detection of anti-HDV (antibodies against HDV).

In Arm 1 (therapeutic), the yeast-based HDV immunotherapy composition is expected to provide a therapeutic benefit to chronically infected HDV patients. The immunotherapy is expected to be safe and well-tolerated at all doses delivered. Patients receiving at least the highest dose of yeast-based HDV immunotherapy are expected to show treatment-emergent, HDV-specific T cell responses as determined by ELISPOT, and patients with prior baseline HDV-specific T cell responses are expected to show improved HDV-specific T cell responses while on treatment. Patients receiving yeast-based HDV immunotherapy are expected to show reductions in HDV RNA and/or improvement in HDV seroconversion rates as compared to the anti-viral group and/or as compared to the placebo controlled group, if utilized. Improvements in ALT normalization are expected in patients receiving yeast-based HDV immunotherapy.

In Arm 2 (prophylaxis), the yeast-based HDV immunotherapy composition is expected to provide protection against co-infection of the HBV monoinfected patients with HDV, including evidence of decreased rates of co-infection with HDV, reduced severity of symptoms and sequela associated with HDV infection, increased overall survival, and/or increased clearance of HDV infection as an acute disease, as compared to the control (placebo group). In addition, patients receiving at least the highest dose of yeast-based HDV immunotherapy are expected to show treatment-emergent, HDV-specific T cell responses as determined by ELISPOT.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims.

What is claimed is:

1. A method of inducing a hepatitis D Virus (HDV)-specific immune response in a subject who is infected with HDV, comprising administering to a subject that has been infected with HDV at least one immunotherapeutic composition comprising:
   a) a yeast vehicle; and
   b) a fusion protein having an amino acid sequence selected from SEQ ID NO: 36 or SEQ ID NO:30 or an amino acid sequence that is at least 99% identical to SEQ ID ID:36 or SEQ ID NO:30, respectively;
   wherein the composition elicits an HDV-specific immune response when administered to the subject.

2. The method of claim 1, further comprising administering to the subject one or more additional agents useful for treating or ameliorating a symptom of HDV infection.

3. The method of claim 2, wherein the compound is an interferon.

4. The method of claim 3, wherein the interferon is interferon-α.

5. The method of claim 3, wherein the interferon is pegylated interferon-α2α.

6. The method of claim 3, wherein the interferon is interferon-λ.

7. The method of claim 1, wherein the subject is chronically infected with hepatitis B virus (HBV).

8. The method of claim 7, further comprising administering to the subject an anti-viral compound to treat the HBV infection.

9. The method of claim 8, wherein the anti-viral compound is selected from the group consisting of: tenofovir, lamivudine, adefovir, telbivudine, entecavir, and combinations thereof.

10. A method to elicit an antigen-specific, cell-mediated immune response against an HDV antigen, comprising administering to a subject at least one composition comprising:
a) a yeast vehicle; and
b) a fusion protein having an amino acid sequence selected from SEQ ID NO: 36 or SEQ ID NO:30 or an amino acid sequence that is at least 99% identical to SEQ ID NO:36 or SEQ ID NO:30, respectively;
wherein the composition elicits an HDV-specific immune response when administered to the subject.

11. The method of claim 1, wherein the fusion protein has an amino acid sequence of SEQ ID NO:36 or SEQ ID NO:30.

12. The method of claim 1, wherein the fusion protein is expressed by the yeast vehicle.

13. The method of claim 1 wherein the yeast vehicle is a whole, heat-inactivated yeast.

14. The method of claim 1, wherein the yeast vehicle is from *Saccharomyces cerevisiae*.

15. The method of claim 10, wherein the fusion protein is expressed by the yeast vehicle.

16. The method of claim 10, wherein the yeast vehicle is a whole, heat-inactivated yeast.

17. The method of claim 10, wherein the yeast vehicle is from *Saccharomyces cerevisiae*.

18. The method of claim 10, wherein the fusion protein has an amino acid sequence of SEQ ID NO:36 or SEQ ID NO:30.

19. The method of claim 10, wherein the subject is chronically infected with hepatitis B virus (HBV).

20. The method of claim 19, further comprising administering to the subject an anti-viral compound to treat the HBV infection.

* * * * *